United States Patent
Nikolskiy et al.

(10) Patent No.: US 11,540,906 B2
(45) Date of Patent: Jan. 3, 2023

(54) PROCESSING DIGITAL DENTAL IMPRESSION

(71) Applicant: James R. Glidewell Dental Ceramics, Inc., Newport Beach, CA (US)

(72) Inventors: Sergey Nikolskiy, Coto de Caza, CA (US); Fedor Chelnokov, Khimki (RU)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 473 days.

(21) Appl. No.: 16/451,991

(22) Filed: Jun. 25, 2019

(65) Prior Publication Data

US 2020/0405456 A1  Dec. 31, 2020

(51) Int. Cl.
*A61C 9/00* (2006.01)
*A61C 13/00* (2006.01)
*A61B 6/14* (2006.01)

(52) U.S. Cl.
CPC .......... *A61C 9/0053* (2013.01); *A61C 9/0006* (2013.01); *A61C 13/0004* (2013.01); *A61B 6/14* (2013.01)

(58) Field of Classification Search
CPC .............. A61C 9/0053; A61C 9/0006; A61C 13/0004; A61B 6/14
See application file for complete search history.

(56) References Cited

U.S. PATENT DOCUMENTS

| | | |
|---|---|---|
| 4,710,876 A | 12/1987 | Cline et al. |
| D302,683 S | 8/1989 | Iwasaki et al. |
| 5,023,895 A | 6/1991 | McCroskey et al. |
| 5,270,827 A | 12/1993 | Kobyayashi et al. |
| 5,368,478 A | 11/1994 | Andreiko et al. |
| 5,431,562 A | 7/1995 | Andreiko et al. |
| 5,447,432 A | 9/1995 | Andreiko et al. |
| 5,454,717 A | 10/1995 | Andreiko et al. |
| 5,605,459 A | 2/1997 | Kuroda et al. |
| D394,316 S | 5/1998 | Kodama et al. |
| 5,879,158 A | 3/1999 | Doyle et al. |
| 6,068,482 A | 5/2000 | Snow |
| 6,081,739 A | 6/2000 | Lemchen |
| 6,091,412 A | 7/2000 | Simonoff |
| 6,152,731 A | 11/2000 | Jordan et al. |

(Continued)

FOREIGN PATENT DOCUMENTS

| | | |
|---|---|---|
| CN | 108024841 A | 5/2018 |
| CN | 108665533 A | 10/2018 |

(Continued)

OTHER PUBLICATIONS

PCT application No. PCT/US20/39324, International Search Report and Written Opinion, dated Oct. 19, 2020.

(Continued)

*Primary Examiner* — Nicholas D Lucchesi
(74) *Attorney, Agent, or Firm* — Charles Fowler

(57) ABSTRACT

A computer-implemented method and system of automatically detecting and removing extraneous material from a digital dental impression includes detecting one or more dental features in a digital dental impression, filtering the one or more dental features, digitally joining the one or more dental features, and determining one or more regions of interest from the joined one or more digital dental features.

31 Claims, 65 Drawing Sheets

(56) References Cited

U.S. PATENT DOCUMENTS

| | | |
|---|---|---|
| 6,198,552 B1 | 3/2001 | Nagae |
| 6,217,334 B1 | 4/2001 | Hultgren |
| 6,227,850 B1 | 5/2001 | Chishti et al. |
| 6,244,861 B1 | 6/2001 | Andreiko et al. |
| 6,318,994 B1 | 11/2001 | Chishti et al. |
| 6,322,359 B1 | 11/2001 | Jordan et al. |
| 6,350,120 B1 | 2/2002 | Sachdeva et al. |
| 6,371,761 B1 | 4/2002 | Cheang et al. |
| 6,386,867 B1 | 5/2002 | Durbin et al. |
| 6,386,878 B1 | 5/2002 | Pavlovskaia et al. |
| 6,406,292 B1 | 6/2002 | Chishti et al. |
| 6,409,504 B1 | 6/2002 | Jones et al. |
| 6,450,807 B1 | 9/2002 | Chishti et al. |
| 6,463,344 B1 | 10/2002 | Pavloskaia et al. |
| 6,512,994 B1 | 1/2003 | Sachdeva |
| 6,554,611 B2 | 4/2003 | Chishti et al. |
| 6,582,225 B1 | 6/2003 | Bergersen |
| D476,658 S | 7/2003 | Adachi et al. |
| 6,602,070 B2 | 8/2003 | Miller et al. |
| 6,621,491 B1 | 9/2003 | Baumrind et al. |
| 6,632,089 B2 | 10/2003 | Rubbert et al. |
| 6,633,789 B1 | 10/2003 | Nikolskiy et al. |
| 6,648,640 B2 | 11/2003 | Rubbert et al. |
| 6,688,886 B2 | 2/2004 | Hughes et al. |
| 6,726,478 B1 | 4/2004 | Isiderio et al. |
| 6,767,208 B2 | 7/2004 | Kaza |
| 6,783,360 B2 | 8/2004 | Chishti |
| 7,013,191 B2 | 3/2006 | Rubbert et al. |
| 7,027,642 B2 | 4/2006 | Rubbert et al. |
| 7,029,275 B2 | 4/2006 | Rubbert et al. |
| 7,040,896 B2 | 5/2006 | Pavlovskaia et al. |
| 7,068,825 B2 | 6/2006 | Rubbert et al. |
| 7,080,979 B2 | 7/2006 | Rubbert et al. |
| 7,110,594 B2 | 9/2006 | Jones et al. |
| 7,134,874 B2 | 11/2006 | Chishti et al. |
| 7,140,877 B2 | 11/2006 | Kaza |
| D533,555 S | 12/2006 | Odhe et al. |
| 7,156,655 B2 | 1/2007 | Sachdeva et al. |
| 7,234,937 B2 | 6/2007 | Sachdeva et al. |
| 7,292,716 B2 | 11/2007 | Kim |
| 7,361,018 B2 | 4/2008 | Imgrund et al. |
| 7,361,020 B2 | 4/2008 | Abolfathi et al. |
| 7,373,286 B2 | 5/2008 | Nikolskiy et al. |
| D573,146 S | 7/2008 | Sukenari et al. |
| D580,962 S | 11/2008 | Sukenari et al. |
| 7,476,100 B2 | 1/2009 | Kuo |
| 7,545,372 B2 | 6/2009 | Kopelman et al. |
| 7,609,875 B2 | 10/2009 | Liu |
| D612,851 S | 3/2010 | Maruyama et al. |
| 7,717,708 B2 | 5/2010 | Sachdeva et al. |
| 7,740,476 B2 | 6/2010 | Rubbert et al. |
| 7,805,003 B1 | 9/2010 | Cohen et al. |
| 8,013,853 B1 | 9/2011 | Douglas et al. |
| 8,045,180 B2 | 10/2011 | Friemel |
| 8,075,306 B2 | 12/2011 | Kitching et al. |
| 8,229,180 B2 | 7/2012 | Baloch et al. |
| 8,308,481 B2 | 11/2012 | DiAngelo et al. |
| 8,332,061 B2 | 12/2012 | Baloch et al. |
| 8,342,843 B2 | 1/2013 | Perot et al. |
| 8,380,644 B2 | 2/2013 | Zouhar et al. |
| D678,383 S | 3/2013 | Park et al. |
| D714,940 S | 10/2014 | Kim |
| 8,855,375 B2 | 10/2014 | Macciola |
| 8,995,732 B2 | 3/2015 | Kaza et al. |
| 9,055,988 B2 | 6/2015 | Galgut et al. |
| 9,135,498 B2 | 9/2015 | Andreiko et al. |
| D742,010 S | 10/2015 | Metcalf |
| 9,421,074 B2 | 8/2016 | Sachdeva et al. |
| D776,818 S | 1/2017 | Metcalf |
| 9,626,462 B2 | 4/2017 | Somasundaram et al. |
| 9,629,698 B2 | 4/2017 | Lior et al. |
| 9,737,381 B2 | 8/2017 | Lee |
| 9,888,983 B2 | 2/2018 | Sachdeva et al. |
| 10,149,744 B2 | 12/2018 | Lior et al. |
| 10,624,717 B2 | 4/2020 | Wen |
| 10,945,812 B1 * | 3/2021 | Raslambekov ......... G06T 17/20 |
| 2001/0002310 A1 * | 5/2001 | Chishti ................ A61C 9/004 433/24 |
| 2002/0006217 A1 | 1/2002 | Rubbert et al. |
| 2002/0028418 A1 | 3/2002 | Farag et al. |
| 2002/0141626 A1 | 10/2002 | Caspi |
| 2002/0150859 A1 | 10/2002 | Imgrund et al. |
| 2002/0180760 A1 * | 12/2002 | Rubbert ................ G16H 50/50 345/630 |
| 2003/0198377 A1 | 10/2003 | Ng |
| 2003/0198378 A1 | 10/2003 | Ng |
| 2003/0207227 A1 | 11/2003 | Abolfathi |
| 2003/0207235 A1 | 11/2003 | Van der Zel |
| 2003/0224314 A1 | 12/2003 | Bergersen |
| 2004/0072120 A1 | 4/2004 | Lauren |
| 2004/0146198 A1 | 7/2004 | Herley |
| 2004/0152036 A1 | 8/2004 | Abolfathi |
| 2004/0175671 A1 | 9/2004 | Jones et al. |
| 2004/0197728 A1 | 10/2004 | Abolfathi et al. |
| 2004/0214128 A1 | 10/2004 | Sachdeva et al. |
| 2005/0018901 A1 | 1/2005 | Kaufmann et al. |
| 2005/0019732 A1 | 1/2005 | Kaufmann et al. |
| 2005/0030368 A1 | 2/2005 | Morrison |
| 2005/0043837 A1 | 2/2005 | Rubbert et al. |
| 2005/0055118 A1 | 3/2005 | Nikolskiy et al. |
| 2005/0089213 A1 | 4/2005 | Geng |
| 2005/0089822 A1 | 4/2005 | Geng |
| 2005/0191593 A1 | 9/2005 | Knopp |
| 2005/0192835 A1 | 9/2005 | Kuo et al. |
| 2005/0208449 A1 | 9/2005 | Abolfathi et al. |
| 2005/0271996 A1 | 12/2005 | Sporbert et al. |
| 2006/0127859 A1 | 6/2006 | Wen |
| 2006/0147872 A1 | 7/2006 | Andreiko |
| 2006/0154198 A1 | 7/2006 | Durbin et al. |
| 2006/0173541 A1 | 8/2006 | Friel |
| 2006/0263739 A1 | 11/2006 | Sporbert et al. |
| 2006/0263741 A1 | 11/2006 | Imgrund et al. |
| 2006/0275736 A1 | 12/2006 | Wen et al. |
| 2007/0003900 A1 | 1/2007 | Miller |
| 2007/0031790 A1 | 2/2007 | Raby et al. |
| 2007/0031791 A1 | 2/2007 | Cinader et al. |
| 2007/0065768 A1 | 3/2007 | Nadav |
| 2007/0128573 A1 | 6/2007 | Kuo |
| 2007/0128574 A1 | 6/2007 | Kuo et al. |
| 2007/0129991 A1 | 6/2007 | Kuo |
| 2007/0134613 A1 | 6/2007 | Kuo et al. |
| 2007/0141527 A1 | 6/2007 | Kuo et al. |
| 2007/0167784 A1 | 7/2007 | Shekhar et al. |
| 2007/0168152 A1 | 7/2007 | Matov et al. |
| 2007/0190481 A1 | 8/2007 | Schmitt |
| 2007/0207441 A1 | 9/2007 | Lauren |
| 2007/0238065 A1 | 10/2007 | Sherwood et al. |
| 2008/0020350 A1 | 1/2008 | Matov et al. |
| 2008/0048979 A1 | 2/2008 | Ruttenberg |
| 2008/0057466 A1 | 3/2008 | Jordan et al. |
| 2008/0064008 A1 | 3/2008 | Schmitt |
| 2008/0176182 A1 | 7/2008 | Hultgren et al. |
| 2008/0182220 A1 * | 7/2008 | Chishti ................... A61C 7/08 433/24 |
| 2008/0248443 A1 * | 10/2008 | Chishti ................... A61C 7/08 433/24 |
| 2008/0261165 A1 | 10/2008 | Steingart et al. |
| 2008/0305458 A1 | 12/2008 | Lemchen |
| 2009/0080746 A1 | 3/2009 | Xu et al. |
| 2009/0087817 A1 | 4/2009 | Jansen et al. |
| 2009/0162813 A1 | 6/2009 | Glor et al. |
| 2009/0191503 A1 | 7/2009 | Matov et al. |
| 2009/0220916 A1 | 9/2009 | Fisker et al. |
| 2009/0246726 A1 | 10/2009 | Chelnokov et al. |
| 2009/0248184 A1 | 10/2009 | Steingart et al. |
| 2009/0298017 A1 | 12/2009 | Boerjes et al. |
| 2009/0311647 A1 | 12/2009 | Fang et al. |
| 2009/0316966 A1 | 12/2009 | Marshall et al. |
| 2010/0009308 A1 | 1/2010 | Wen et al. |
| 2010/0100362 A1 | 4/2010 | Zouhar et al. |
| 2010/0105009 A1 | 4/2010 | Karkar et al. |
| 2010/0111386 A1 | 5/2010 | El-Baz |
| 2010/0138025 A1 | 6/2010 | Morton et al. |
| 2010/0145898 A1 | 6/2010 | Malfliet et al. |

(56) References Cited

U.S. PATENT DOCUMENTS

| | | |
|---|---|---|
| 2010/0217567 A1 | 8/2010 | Marshall |
| 2010/0260405 A1 | 10/2010 | Cinader, Jr. |
| 2010/0297572 A1 | 11/2010 | Kim |
| 2011/0004331 A1 | 1/2011 | Cinader, Jr. et al. |
| 2011/0045428 A1 | 2/2011 | Boltunov et al. |
| 2011/0059413 A1 | 3/2011 | Schutyser et al. |
| 2011/0060438 A1 | 3/2011 | Stoddard et al. |
| 2011/0090513 A1 | 4/2011 | Seidl et al. |
| 2011/0184762 A1 | 7/2011 | Chishti et al. |
| 2011/0206247 A1 | 8/2011 | Dachille et al. |
| 2011/0207072 A1 | 8/2011 | Schiemann |
| 2011/0244415 A1 | 10/2011 | Batesole |
| 2011/0268326 A1 | 11/2011 | Kuo et al. |
| 2011/0292047 A1 | 12/2011 | Chang et al. |
| 2012/0015316 A1 | 1/2012 | Sachdeva |
| 2012/0065756 A1 | 3/2012 | Rubber et al. |
| 2012/0088208 A1 | 4/2012 | Schulter et al. |
| 2012/0139142 A1 | 6/2012 | Van der Zel |
| 2012/0214121 A1 | 8/2012 | Greenberg |
| 2013/0172731 A1 | 7/2013 | Gole |
| 2013/0218531 A1 | 8/2013 | Deichmann et al. |
| 2013/0226534 A1 | 8/2013 | Fisker et al. |
| 2013/0275107 A1 | 10/2013 | Alpern et al. |
| 2013/0325431 A1 | 12/2013 | See et al. |
| 2013/0329020 A1 | 12/2013 | Kriveshko et al. |
| 2013/0335417 A1 | 12/2013 | McQueston et al. |
| 2014/0003695 A1 | 1/2014 | Dean et al. |
| 2014/0055135 A1 | 2/2014 | Nielsen et al. |
| 2014/0067334 A1 | 3/2014 | Kuo |
| 2014/0067337 A1 | 3/2014 | Kopleman |
| 2014/0185742 A1 | 7/2014 | Chen et al. |
| 2014/0272772 A1 | 9/2014 | Andreiko et al. |
| 2014/0278278 A1 | 9/2014 | Nikolskiy et al. |
| 2014/0278279 A1 | 9/2014 | Azernikov et al. |
| 2014/0308624 A1 | 10/2014 | Lee et al. |
| 2014/0329194 A1 | 11/2014 | Sachdeva et al. |
| 2014/0379356 A1 | 12/2014 | Sachdeva et al. |
| 2015/0049081 A1 | 2/2015 | Coffey et al. |
| 2015/0056576 A1 | 2/2015 | Nikolskiy et al. |
| 2015/0111168 A1 | 4/2015 | Vogel |
| 2015/0154678 A1 | 6/2015 | Fonte et al. |
| 2015/0182316 A1 | 7/2015 | Morales et al. |
| 2015/0320320 A1 | 11/2015 | Kopelman et al. |
| 2015/0347682 A1 | 12/2015 | Chen et al. |
| 2016/0135924 A1 | 5/2016 | Choi et al. |
| 2016/0148370 A1 | 5/2016 | Maury et al. |
| 2016/0239631 A1 | 8/2016 | Wu et al. |
| 2016/0256035 A1 | 8/2016 | Kopelman et al. |
| 2016/0256246 A1 | 9/2016 | Stapleton et al. |
| 2016/0367336 A1 | 12/2016 | Lv et al. |
| 2017/0100214 A1 | 4/2017 | Wen |
| 2017/0135655 A1 | 5/2017 | Wang et al. |
| 2017/0231721 A1 | 8/2017 | Akeel et al. |
| 2017/0340418 A1 | 11/2017 | Raanan |
| 2018/0028063 A1 | 2/2018 | Elbaz et al. |
| 2018/0028064 A1 | 2/2018 | Elbaz et al. |
| 2018/0028065 A1 | 2/2018 | Elbaz et al. |
| 2018/0055600 A1 | 3/2018 | Matov et al. |
| 2018/0132982 A1 | 5/2018 | Nikolskiy et al. |
| 2018/0146934 A1 | 5/2018 | Ripoche et al. |
| 2018/0165818 A1 | 6/2018 | Tsai et al. |
| 2018/0189420 A1 | 7/2018 | Fisker |
| 2018/0303581 A1 | 10/2018 | Martz et al. |
| 2019/0374318 A1 | 12/2019 | Jesenko |
| 2020/0121429 A1 | 4/2020 | Pesach et al. |

FOREIGN PATENT DOCUMENTS

| | | |
|---|---|---|
| EP | 2345387 A2 | 7/2011 |
| EP | 2886077 A1 | 6/2015 |
| WO | 0180761 A2 | 11/2001 |
| WO | 2001080763 A2 | 11/2001 |
| WO | 2003053274 | 7/2003 |
| WO | 2013180423 A1 | 5/2013 |
| WO | 2016097033 A1 | 6/2016 |
| WO | 2017178908 A1 | 10/2017 |
| WO | 2018022054 A1 | 2/2018 |
| WO | 2018038748 A1 | 3/2018 |
| WO | 2018101923 A1 | 6/2018 |

OTHER PUBLICATIONS

International Search Report and Written Opinion in International PCT Application No. PCT/US2020/039383 dated Sep. 25, 2020 (20 pages).

Andrew W. Fitzgibbon et al., Direct Least Squares Fitting of Ellipses, The University of Edinburgh, Department of Artificial Intelligence, Jan. 4, 1996, in 15 pages.

Oscar Sebio Cajaraville, Four Ways to Create a Mesh for a Sphere, Medium.com, Dec. 7, 2015, in 9 pages.

Shuai Yang, Interactive Tooth Segmentation Method of Dental Model based on Geodesic, Research Gate, Jan. 2017, in 6 pages.

Emiliano Perez et al., A Comparison of Hole-Filing Methods in 3D, Int. J. Appl. Math. Comput. Sci., 2016, vol. 26, No. 4, 885-903, in 19 pages.

Yokesh Kumar et al., Automatic Feature Identification in Dental Meshes, ResearchGate, Article in Computer-Aided Design and Applications, Aug. 2013, in 24 pages.

Andrew W. Fitzgibbon et al., Direct Least Squares Fitting of Ellipses, Department of Artificial Intelligence, The University of Edinburgh, dated Jan. 4, 1996, in 15 pages.

Oscar Sebio Cajaraville, Four Ways to Create a Mesh for a Sphere, Dec. 7, 2015, in 9 pages.

Shuai Yang et al., Interactive Tooth Segmentation Method of Dental Model based on Geodesic, ResearchGate, Conference paper, Jan. 2017, in 6 pages.

Changhwan Kim et al., Efficient digitalization method for dental restorations using micro-CT data, nature.com/scientificreports, published Mar. 15, 2017, in 8 pages.

Dexter C. Kozen, The Design and Analysis of Algorithms, Texts and Monographs in Computer Science, (c) 1992, See Whole book.

Bob Sedgewick et al., Algorithms and Data Structures Fall 2007, Department of Computer Science, Princeton University, https://www.cs.princeton.edu/~rs/AlgsDS07/, downloaded Oct. 28, 2021, in 41 pages.

Alban Pages et al., Generation of Computational Meshes from MRI and CT-Scan data, ResearchGate, ESAIM Proceedings, Sep. 2005, vol. 14, 213-223 in 12 pages.

William E. Lorensen et al., Marching Cubes: A High Resolution 3D Surface Construction Algorithm, Computer Graphics, vol. 21, No. 4, Jul. 1987 in 7 pages.

Alfred V. Aho et al., The Design and Analysis of Computer Algorithms, Addison-Wesley Publishing Company, Jun. 1974, pp. 124-155.

Sheng-hui Liao et al., Automatic Tooth Segmentation of Dental Mesh Based on Harmonic Fields, Hindawi Publishing Corporation, BioMed Research International, vol. 2015, Article ID 187173, in 11 pages.

Changhwan Kim, Scientific Reports, "Efficient digitalization method for dental restorations using micro-CT data", www.nature.com/scientificreports, 7:44577|DOI:10.1038/srep44577 (dated Mar. 15, 2017).

Höllt et al, GPU-Based Direct Volume Rendering of Industrial CT Data, 2007, VRVis Research Center, in 84 pages.

Kilic et al, GPU Supported Haptic Device Integrated Dental Simulation Environment, in 6 pages.

Zheng et al, Finite Difference Error Analysis of Geometry Properties of Implicit Surfaces, 2011, IEEE Symposium on Computers & Informatics, in 6 pages.

Ibraheem, Reduction of artifacts in dental cone beam CT images to improve the three dimensional image reconstruction, Research Gate, Article in Journal of Biomedical Science and Engineering, January 20212, in 8 pages.

Fan et al. "Virtual adjustment of the occlusal surface for complete denture tooth arrangement" 2015 International Symposium on Bioelectronics and Bioinformatics (ISBB). IEEE, 2015. (Year: 2015).

(56) References Cited

OTHER PUBLICATIONS

Kumar et al. "Improved segmentation of teeth in dental models." Computer-Aided Design and Applications 8.2 (2011): 211-224. (Year: 2011).

Kumar et al. "Automatic feature identification in dental meshes" Computer-Aided Design and Applications 9.6 (2012): 747-769. (Year: 2012).

Murat Arikan et al., O-Snap: Optimization-Based Snapping for Modeling Architecture, ACM Transactions on Grphics, vol. 32, No. 1, Article 6, Publication date: Jan. 2013, in 15 pages.

Brian Amberg et al., Optimal Step Nonrigid ICP Algorithms for Surface Registration, downloaded on Apr. 2, 2022 from IEEE Xplore, in 8 pages.

T. Rabbani et al., Segmentation of Point Clouds Using Smoothness Constraint, ISPRS Commission V Symposium Image Engineering and Vision Metrology, in 6 pages.

Bribiesca, E. "3D-Curve Representation by Means of a Binary Chain Code", Mathematical and computer modelling 40.3(2004):285-295; p. 292, paragraph 2; p. 293, paragraph 1.

Kiattisin, S. et al. "A Match of X-Ray Teeth Films Using Image Processing Based on Special Features of Teeth", SICE Annual Conference, 2008. IEEE: Aug. 22, 2008; p. 97; col. 2, paragraph 2; a 98, col. 1-2.

Cui, M, Femiani, J., Hu, J., Wondka, Razada A. "Curve Matching for Open 2D Curves", Pattern Recognition Letters 30 (2009): pp. 1-10.

Gumhold, S., Wang, X., MacLeod R. "Feature Extraction From Point Clouds", Scientific Computing and Imaging Institute: pp. 1-13 Proceedings, 10th International Meshing Roundtable, Sandia National Laboratores, pp. 293-305, Oct. 7-10, 2001.

Wolfson, H. "On Curve Matching", Robotics Research Technical Report, Technical Report No. 256, Robotic Report No. 86 (Nov. 1986) New York University, Dept. of Computer Science, New York, New York 10012.

Rietzel et al, "Moving targets: detection and tracking of internal organ motion for treatment planning and patient set up", Radiotherapy and Oncology, vol. 73, supplement 2, Dec. 2004, pages S68-S72.

Brian Amberg et al., Optimal Step Nonrigid ICP Algorithms for Surface Registration, Proceedings/CVPR, IEEE Computer Society Conference on Computer Vision and Pattern Recognition, IEEE Computer Society Conference on Computer Vision and Pattern Recognition, Jun. 2007, in 9 pages.

T. Rabbani et al., Segmentation of Point Clouds Using Smoothness Constraint, ISPRS vol. XXXVI, Part 5, Dresden Sep. 25-37, 2006, in 6 pages.

* cited by examiner

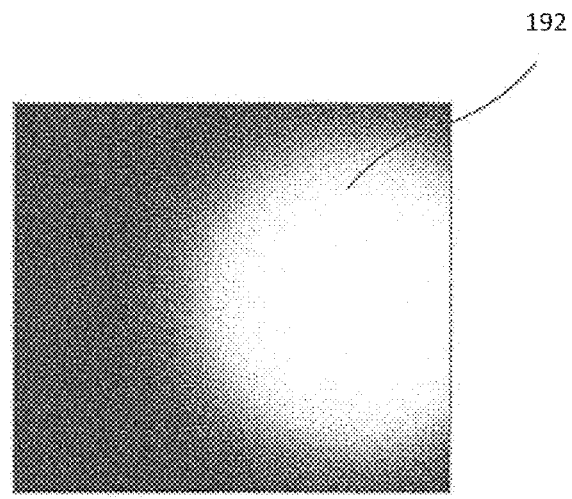
FIG. 8A
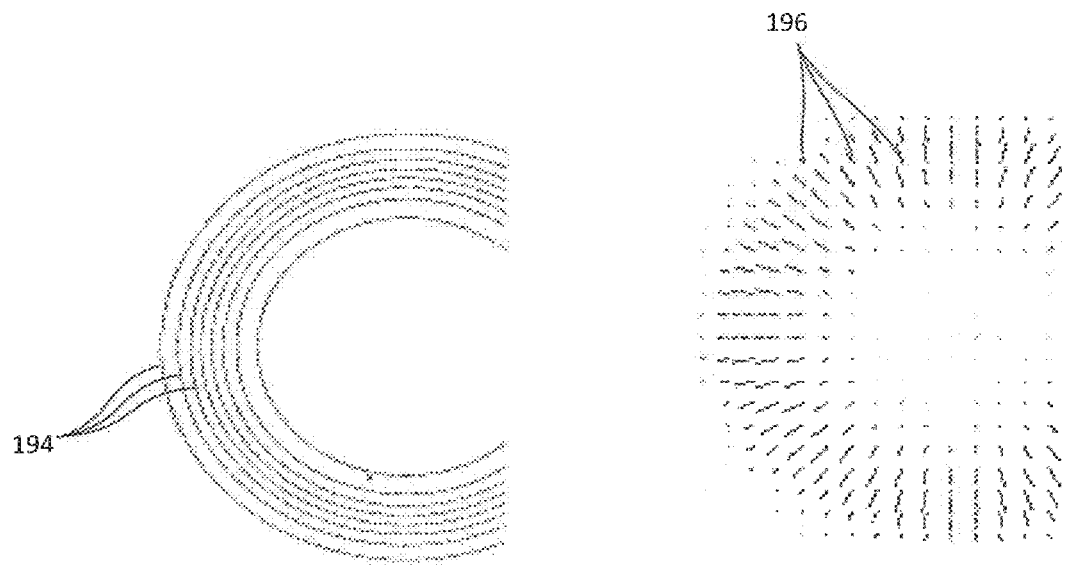
FIG. 8B
FIG. 8C

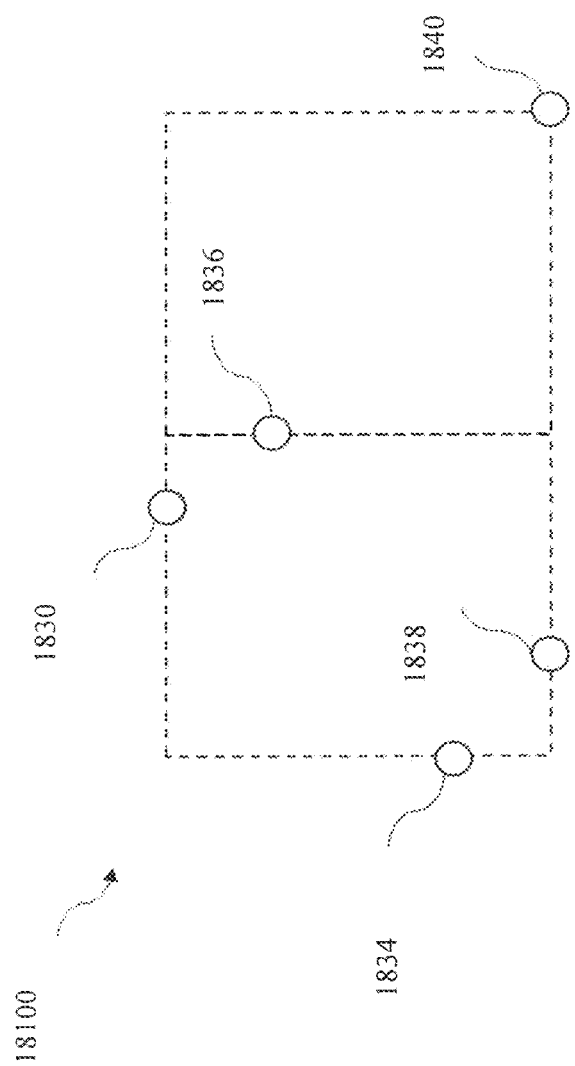

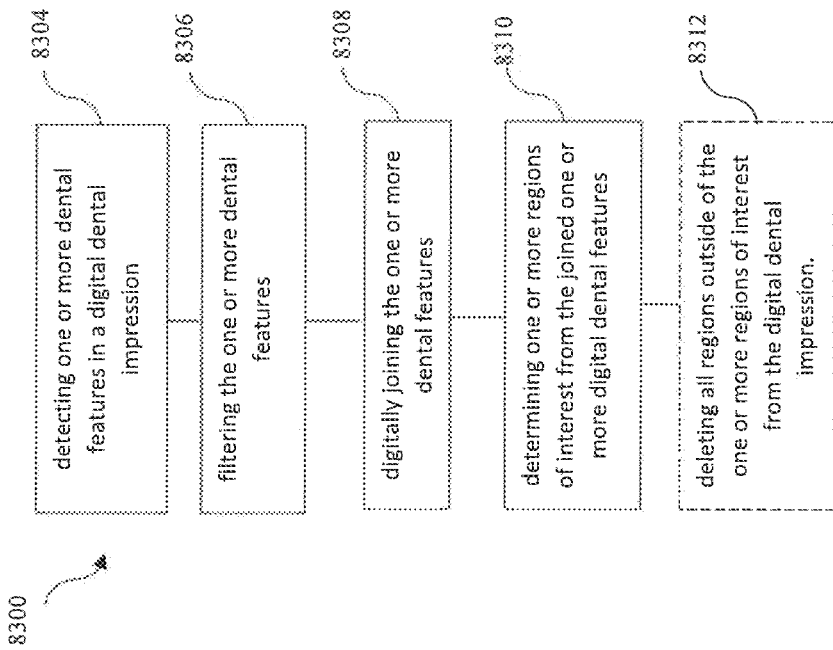

PROCESSING DIGITAL DENTAL IMPRESSION

BACKGROUND

Specialized dental laboratories typically use computer-aided design (CAD) and computer-aided manufacturing (CAM) milling systems to manufacture dental prostheses based on patient-specific instructions provided by dentists. In a typical work flow, the dental laboratories receive information about a patient's oral situation from a dentist. Using this information, the dental laboratory designs a dental prosthesis on the CAD system and manufactures the prosthesis on the CAM system with a mill or other fabrication system. To use the CAD/CAM system, a digital model of the patient's dentition is required as an input to the process. Several techniques may be used to produce a digital dental model. Traditional dental laboratories use a stone and plaster process to scan and digitize a physical dental impression into a digital dental model.

Although digitizing a physical dental impression can provide a digital dental model for a CAD/CAM system, digital dental impressions can contain extraneous data that is not useful for dental processing and can interfere with viewing useful information. This extraneous data can represent walls and other extra material, for example. The presence of walls and extra material in the digital dental impression can be problematic, for example, since it can obscure views of teeth and gums in the model from certain views/angles. This can limit the ability of a dental professional to view, diagnose, and/or manipulate the digital dental model. The presence of extraneous data can thus reduce the use of the digital dental model. Detection of and removal of the extraneous data from the digital dental impressions while preserving teeth and gum regions would be desirable. However, empirically detecting the boundary between teeth and gum regions and the extraneous material and removing the extraneous material from the digital dental model can be problematic.

SUMMARY

A computer-implemented method of automatically detecting and removing extraneous material from a digital dental impression, including: detecting one or more dental features in a digital dental impression, filtering the one or more dental features, digitally joining the one or more dental features, and determining one or more regions of interest from the joined one or more digital dental features.

Also disclosed is a non-transitory computer readable medium storing executable computer program instructions for digitally processing a digital dental impression the computer program instructions that includes instructions for detecting one or more anatomical dental features in a digital dental impression, filtering the one or more anatomical dental features, digitally joining the one or more anatomical dental features, and determining one or more regions of interest from the joined anatomical dental features.

Also disclosed is a digital impression processing system for creating a digital model from a CT scan, which includes: a processor, a computer-readable storage medium includes instructions executable by the processor to perform steps including: detecting one or more anatomical dental features in a digital dental impression, filtering the one or more anatomical dental features, digitally joining the one or more anatomical dental features, and determining one or more regions of interest from the joined anatomical dental features.

BRIEF DESCRIPTION OF THE DRAWINGS

FIG. 8A is an illustration of a cross-section of the cylinder of FIG. 7.

FIG. 8B is an illustration of iso-surfaces derived from the 3D image of the cylinder of FIG. 7.

FIG. 8C is an illustration of gradient vectors derived from the iso-surfaces shown in FIG. 8B.

FIG. 11(c) is a perspective view of an example of a portion of a 3 dimensional point cloud depicted for simplicity in 2 dimensions.

FIG. 49 is a flow chart illustrating an example of determining one or more regions of interest.

DETAILED DESCRIPTION

Figure 1:
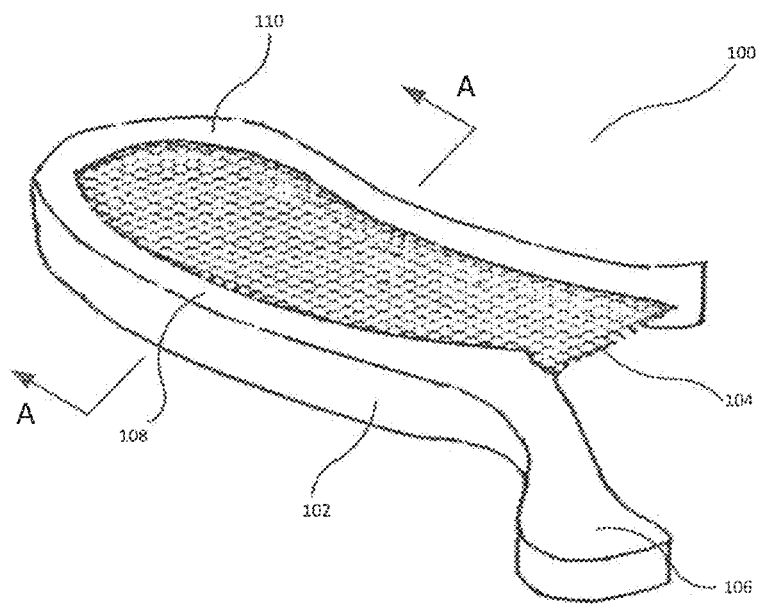
FIG. 1 is a perspective view of a three-way dental impression tray.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In some examples, values, procedures, or apparatus may be referred to as "lowest," "best," "minimum," or the like. It will be appreciated that such descriptions are intended to indicate that a selection among many alternatives can be made, and such selections need not be better, smaller, or otherwise preferable to other selections.

In the following description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object.

A digital dental impression can be generated by scanning any type of physical dental impression into a single digital dental impression image using any type of scanner. For example, the physical impression can be scanned with a CT scanner, an optical scanner, etc. to generate the single digital dental impression.

In some embodiments, a computer-implemented method of digitally processing a digital dental impression includes determining one or more first and second digital surface regions visible from directions on a first and second side of the digital dental impression, around an occlusion axis, segmenting the digital dental impression, and digitally splitting the one or more first digital segments from the one or more second digital segments.

Digital Dental Impression

As noted above, in a typical work flow, information about the oral situation of a patient is received from a dentist, the dental laboratory designs the dental prosthesis, and the prosthesis is manufactured using a mill or other fabrication system. When making use of CAD design and CAM manufacturing in dentistry, a digital model of the patient's dentition is required as an input to the process. Despite the rise of intraoral scanning technology, the prevalent method of acquisition of digital model data is still scanning a stone model cast from a physical negative impression of the patient's dentition.

A physical negative impression of the patient's dentition is typically obtained by the use of a dental impression tray containing impression material. One example is described in U.S. Patent Application Pub. No. US20180132982A1 to Nikolskiy et al., which is hereby incorporated by reference in its entirety.

An example of an impression tray is shown in FIG. 1 in the form of a three-way impression tray or "triple tray" 100. The triple tray 100 includes a generally rigid frame 102 within which a mesh 104 is retained. The rigid frame defines a handle 106 configured to be gripped by the user, a buccal side wall 108, and a lingual side wall 110. In use, impression material is loaded onto the upper and lower surfaces of the mesh 104 by the clinician. The triple tray 100 is then inserted into the mouth of a patient and the patient is instructed to bite down onto the triple tray 100 and impression material, causing the impression material to conform to the patient's dentition as the impression material cures. Because the triple tray 100 is situated between the upper and lower jaws of the patient, the impression obtained via the triple tray 100 includes information about the dental situation of the patient's upper jaw, lower jaw, and bite registration in the area of the patient's dentition covered by the triple tray.

Figure 2:
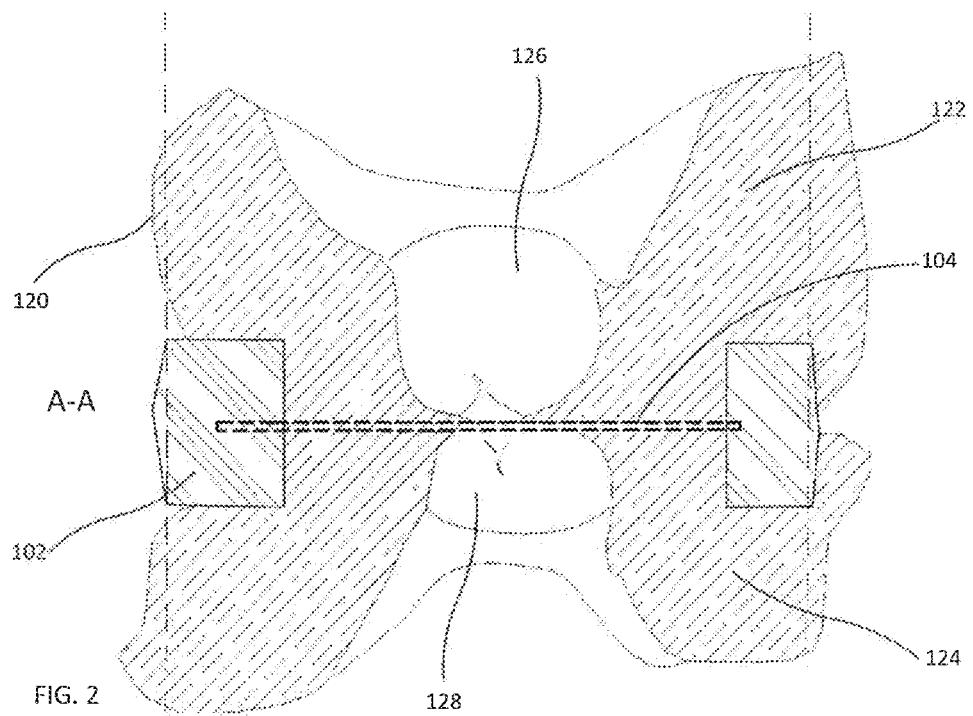
FIG. 2 is a cross-sectional view of a three-way dental impression tray containing impression material.

For example, in FIG. 2, there is shown a sectional view of the triple tray 100 containing impression material 120 after the taking of a physical impression of a patient. An upper impression 122 is formed on the upper side of the mesh 104, and a lower impression 124 is formed on the lower side of the mesh 104. As noted above, after deformation, the impression material 122 defines a physical negative impression of the patient's dentition. Accordingly, the upper void space 126 defined by the upper impression 122 defines the space occupied by the patient's teeth and gingiva in the patient's upper jaw, and the lower void space 128 defined by the lower impression 124 defines the space occupied by the patient's teeth and gingiva in the patient's lower jaw. Moreover, the position and orientation of the upper void space 126 relative to the lower void space 128 defines the bite registration of the patient's dentition in the subject area, including the occlusal spacing and registration.

As noted above, in a conventional workflow, a physical dental impression formed in the manner described above would be used to cast a model of the patient's dentition formed of stone, polymeric, or other suitable material. The cast model would then be scanned using an optical scanner in order to obtain a digital model. The digital model would then be used to design one or more restorations, or for other purposes. This conventional workflow creates potential sources of error or inaccuracy that would be avoided by alternative methods or alternative workflows that avoided the step of forming the cast model and, instead, proceeded directly from the physical impression to a digital model.

Figure 3:
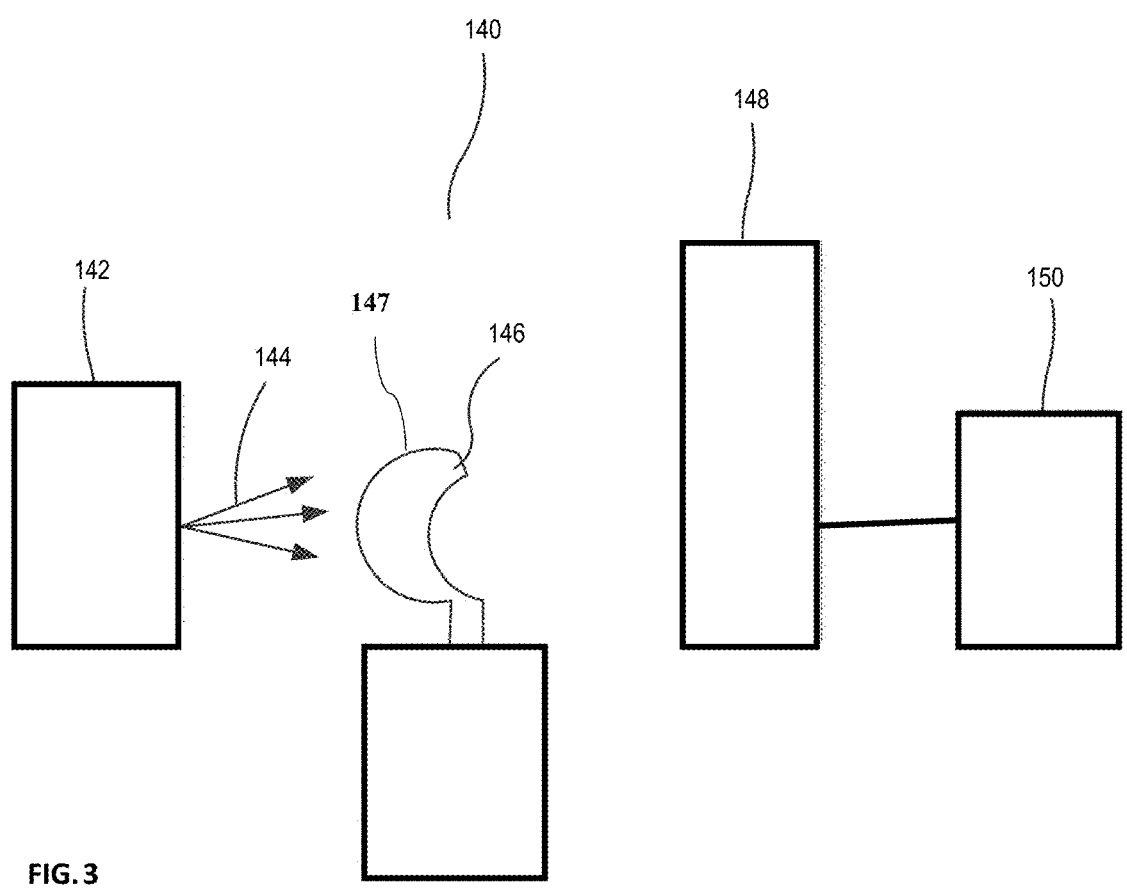
FIG. 3 is a schematic diagram of a computed tomography (CT) scanning system.

In one embodiment of the present method, a computed tomography (CT) scanner uses x-rays to make a detailed image of a physical impression. A plurality of such images are then combined to form a 3D model of the patient's dentition. A schematic diagram of an example of a CT scanning system 140 is shown in FIG. 3. The CT scanning system 140 includes a source of x-ray radiation 142 that emits an x-ray beam 144. An object being scanned—in the present case, a triple tray containing a physical impression 146—is placed between the source 142 and an x-ray detector 148. The x-ray detector 148, in turn, is connected to a processor 150 that is configured to receive the information from the detector 148 and to convert the information into a digital image file. Those skilled in the art will recognize that the processor 150 may comprise one or more computers that may be directly connected to the detector, wirelessly connected, connected via a network, or otherwise in direct or indirect communication with the detector 148.

An example of a suitable scanning system 140 includes a Nikon Model XTH 255 CT (Metrology) Scanner which is commercially available from Nikon Corporation. The example scanning system includes a 225 kV microfocus x-ray source with a 3 µm focal spot size to provide high performance image acquisition and volume processing. The processor 150 may include a storage medium that is configured with instructions to manage the data collected by the scanning system.

Figure 4:
FIG. 4 is a 2-dimensional (2D) radiographic image of a dental impression tray containing a dental impression.

As noted above, during operation of the scanning system 140, the impression 146 is located between the x-ray source 142 and the x-ray detector 148. A series of images of the impression 146 are collected by the processor 150 as the impression 146 is rotated in place between the source 142 and the detector 146. An example of a single image 160 is shown in FIG. 4. The image 160 may be a radiograph, a projection, or other data in the form of a digital image. In one embodiment, a series of 720 images are collected as the impression 146 is rotated in place between the source 142 and the detector 148. In other embodiments, more images or fewer images may be collected as will be understood by those skilled in the art.

Figure 5:
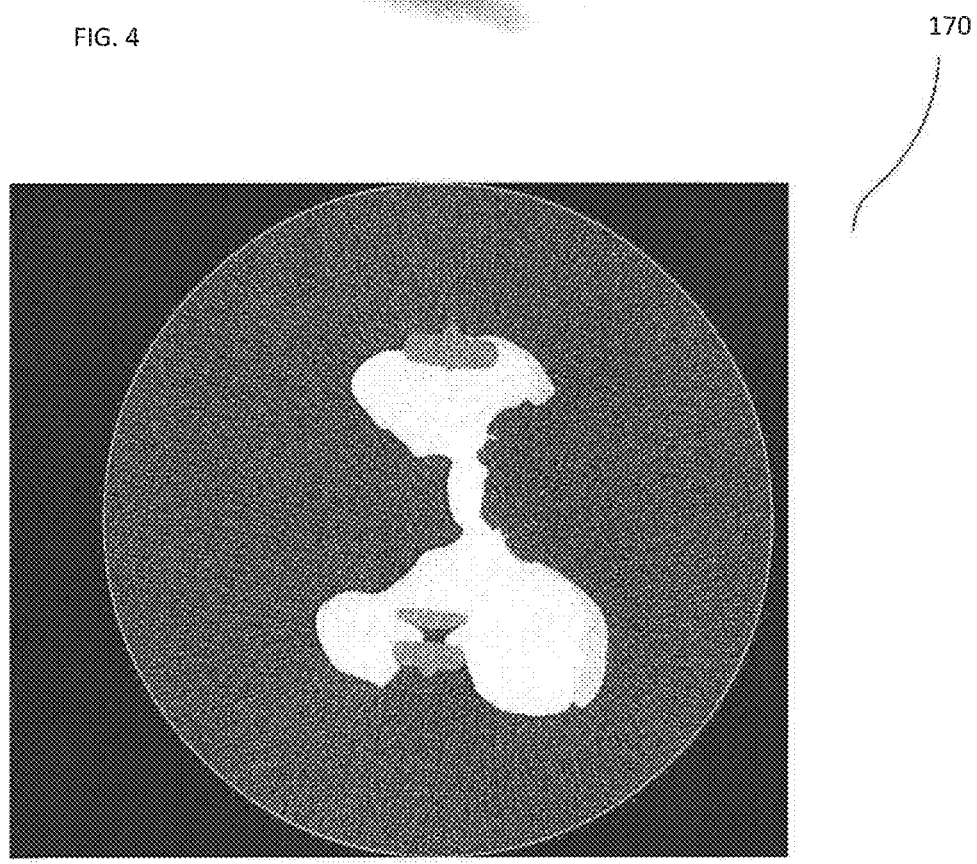
FIG. 5 is a cross-section of a 3-dimensional (3D) volumetric image.

The plurality of images 160 of the impression 146 are generated by and stored within a storage medium contained within the processor 150 of the scanning system 140, where they may be used by software contained within the processor to perform additional operations. For example, in an embodiment, the plurality of images 160 undergo tomographic reconstruction in order to generate a 3D virtual image 170 (see FIG. 5) from the plurality of 2D images 160 generated by the scanning system 140. In the embodiment shown in FIG. 5, the 3D virtual image 170 is in the form of a volumetric image or volumetric density file (shown in cross-section in FIG. 5) that is generated from the plurality of radiographs 160 by way of a reconstruction algorithm associated with the scanning system 140.

Figure 6:
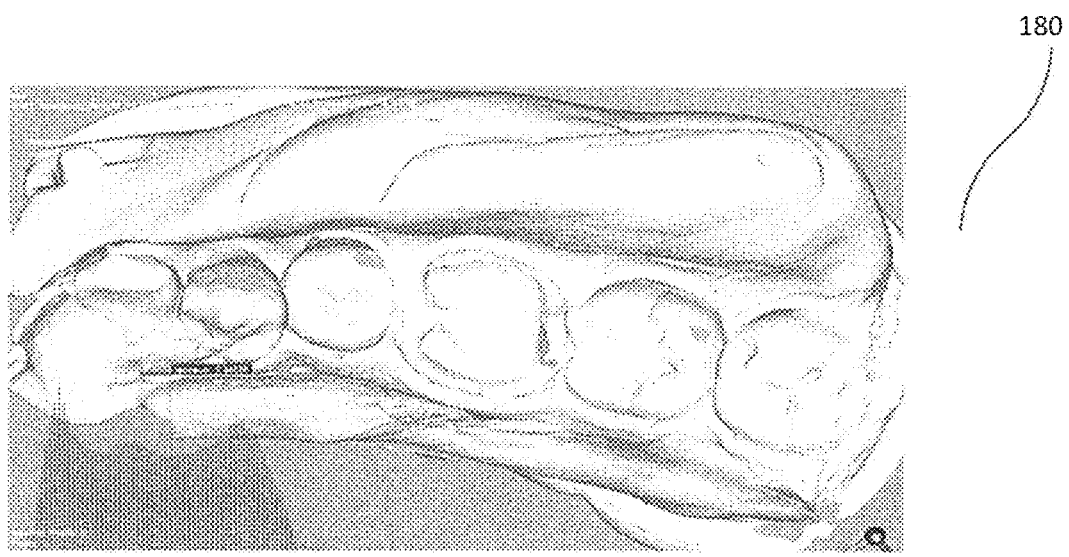
FIG. 6 is a 3-dimensional (3D) surface image representation of a portion of a patient's dentition.

In one embodiment, the volumetric image 170 is converted into a surface image 180 (see, e.g., FIG. 6) using a surface imaging algorithm. In the embodiment shown, the volumetric image 170 is converted into a surface image 180 having a format (e.g., an .STL file format) that is suitable for use with a dental restoration design software, such as the FastDesign™ dental design software provided by Glidewell Laboratories of Newport Beach, Calif.

Figure 7:
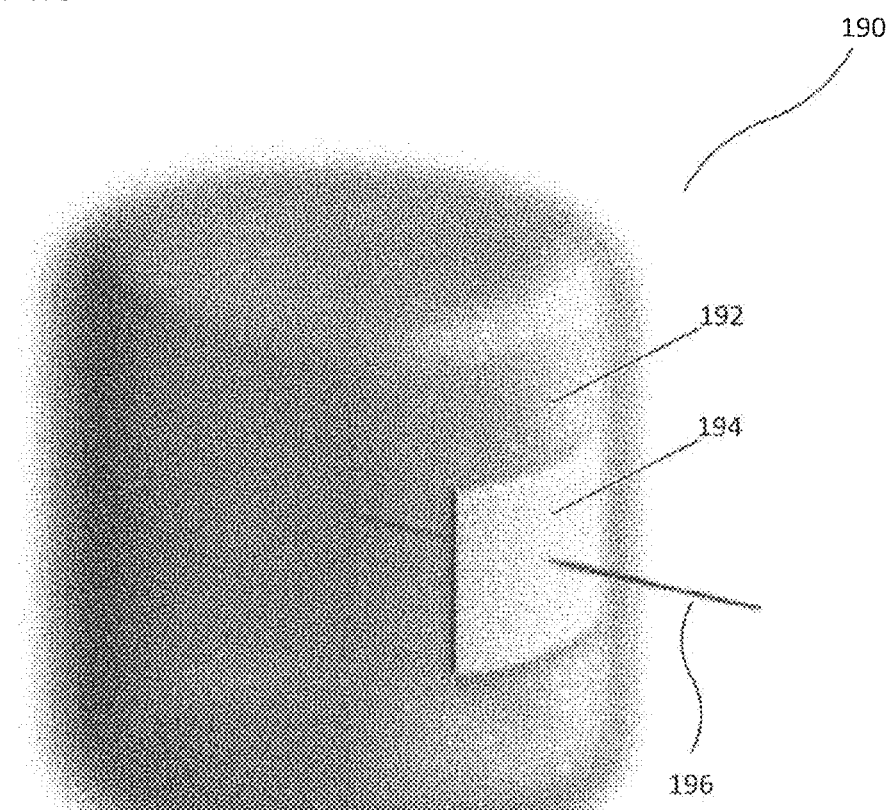
FIG. 7 is an illustration of a 3-dimensional (3D) object in the form of a cylinder.
Figure 8D:
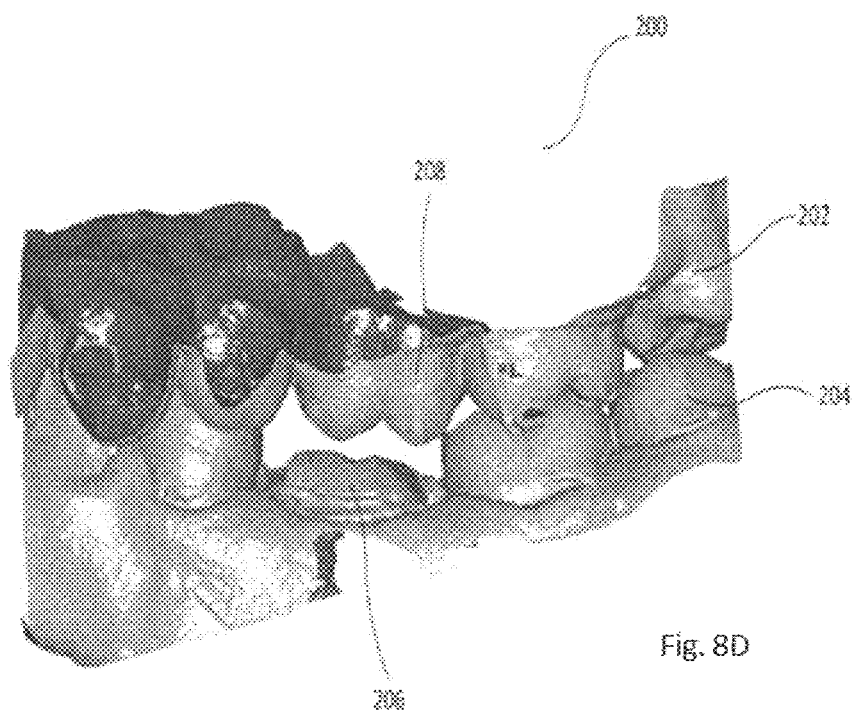
FIG. 8D is a perspective view of a surface image representation of a portion of a patient's dentition including portions of the dentition of an upper jaw and portions of the dentition of a lower jaw.

In one embodiment, the surface imaging algorithm used to convert the volumetric image 170 into a surface image 180 is configured to construct the surface image of the dentition 180 directly from the volumetric image 170 without including an intermediate step of constructing a surface image of the impression. For example, FIGS. 7 and 8A-C do not show images of a dental impression or of a patient's dentition, but are instead presented to illustrate by way of example the direct surface imaging method employed in the illustrated embodiment. In FIG. 7, a volumetric image 190 of an object having a boundary 192 that is not precisely defined. A small patch of an iso-surface 194 is illustrated within the boundary 192, with the iso-surface 194 representing a collection of points within the volumetric image 190 that have the same volumetric density value. It is a mathematical property that a gradient vector 196 at a given position will always point perpendicular to an iso-surface 194 at position. Accordingly, the gradient vector 196 is used to determine the direction which passes perpendicularly through the object boundary 192. These properties are further illustrated in FIGS. 8A-C, which show the non-precisely defined boundary 192 of the object (FIG. 8A), a plurality of iso-surfaces 194 of the object (FIG. 8B), and a plurality of gradient vectors 196 that are perpendicular to the iso-surfaces at given positions with in the object (FIG. 8C).

In the embodiment shown, as described above, a dental impression is collected using a triple tray 100 dental impression tray, thereby collecting an upper impression 122, a lower impression 124, and a bite registration in a single step. As a result, after scanning, reconstruction, and generation of a volumetric image of the triple tray and impression 146 (see FIG. 3), the resulting surface image 200 (see FIG. 8D) includes a surface image of the upper dentition 202, a surface image of the lower dentition 204, and their relative positions and orientation providing information about the bite registration between the upper and lower dentition. These surface images 202, 204 and bite registration information are obtained using a single scan of a single object (the triple tray and impression 146).

One or more methods and systems of digitally processing a digital model from a CT or optical scan of a physical dental impression are described herein. In some embodiments, computer-implemented executable methods of processing a digital dental impression as described herein can, for example, use the digital model generated by surface imaging algorithms applied to a CT or optically scanned dental impression.

Figure 9:
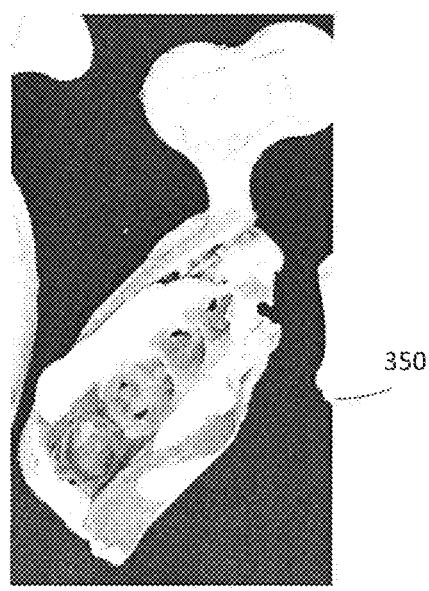
FIG. 9 is a perspective view of a physical dental impression.
Figure 16:
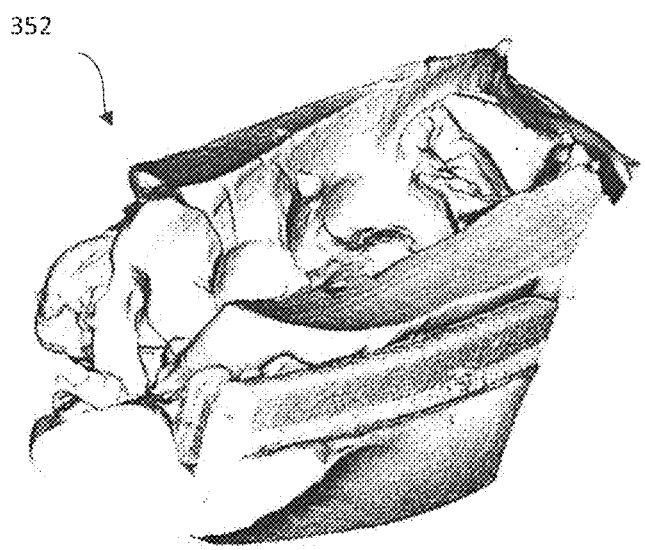
FIG. 16 is a 3-dimensional (3D) view of a digital dental impression.

FIG. 9 illustrates one example of a physical dental impression 350 bitten from two sides by a patient, thereby creating a physical impression of an upper jaw and a physical impression of a lower jaw. Scanning of the physical dental impression 350 can generate a digital model or digital dental impression 352 as shown in FIG. 16. Scanning can include CT scanning (including CBCT scanning), or optical scanning. In some embodiments, the CT or optical scanner can scan a physical impression of any type. In some embodiments, the CT or optical scanner can scan a stone model of a the physical impression of any type. In some embodiments, the digital model includes interconnected digital surface triangles (also referred to as "triangles") that together comprise a digital surface mesh.

Figure 10:
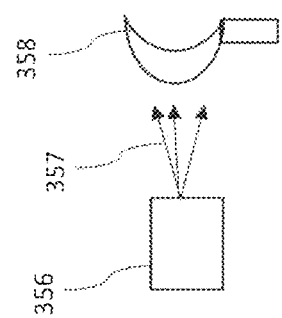
FIG. 10 is an illustration of an optical scanner.

In the case of optical scanning as shown in FIG. 10, an optical scanner 356 can emit light beams 357 to scan and digitize a physical dental impression 358, such as a triple tray dental impression, for example. Data obtained from scanning the surface of the physical dental impression 358 may be in the form of sets of points, or point clouds, triangles, or digital surface meshes. A 3D model may digitally represent a physical dental impression, for example, by using a collection of points in 3D space connected by various geometric entities such as triangles. The scan may be stored locally, or remotely, for example, for use in the methods described herein. The scan may be saved as a 3D scan, as point clouds or digital surface meshes for use in the methods described herein as a digital dental impression.

In the case of CT scanning, the digital surface mesh and digital dental impression can be created/determined using the methods described in the application PROCESSING CT SCAN OF DENTAL IMPRESSION, Ser. No. 16/451,315, assigned to the assignee of this application and filed concurrently with this application, and which is hereby incorporated by reference in its entirety, by Marching Cubes, or by other digital model generation methods and techniques known in the art.

For example, a point cloud can be generated by the computer-implemented method using the methods disclosed in Processing CT Scan of Dental Impression in some embodiments. In some embodiments, the point cloud can be generated and/or adjusted (reduced) by the computer-implemented method automatically. The computer-implemented method receives as input a volumetric density file generated by a CT scanner. The computer-implemented method compares a selected iso-value of density to densities of one or more voxels in a volumetric density file and generates digital surface points at the selected iso-value of density in a point cloud. The iso-value of density can be a selectable value that can be chosen by a user and/or can be automatically determined in some embodiments. In some embodiments, if the selected iso-value of density corresponds to the density of one or more voxels in the volumetric density file, then zero or more digital surface points can be generated and arranged in virtual 3D space at position(s) in the point cloud corresponding to position(s) of one or more voxels in the volumetric density file by the computer-implemented method. In some embodiments, as discussed below, if the selected iso-value of density is between two voxel density values, then zero or more digital surface points can be generated and arranged in virtual 3D space in position(s) corresponding to position(s) between two voxel positions along a voxel edge by the computer-implemented method. The computer-implemented method can optionally adjust the point cloud. The computer-implemented method can generate a digital surface mesh for either the point cloud or the adjusted point cloud.

Figure 11A:
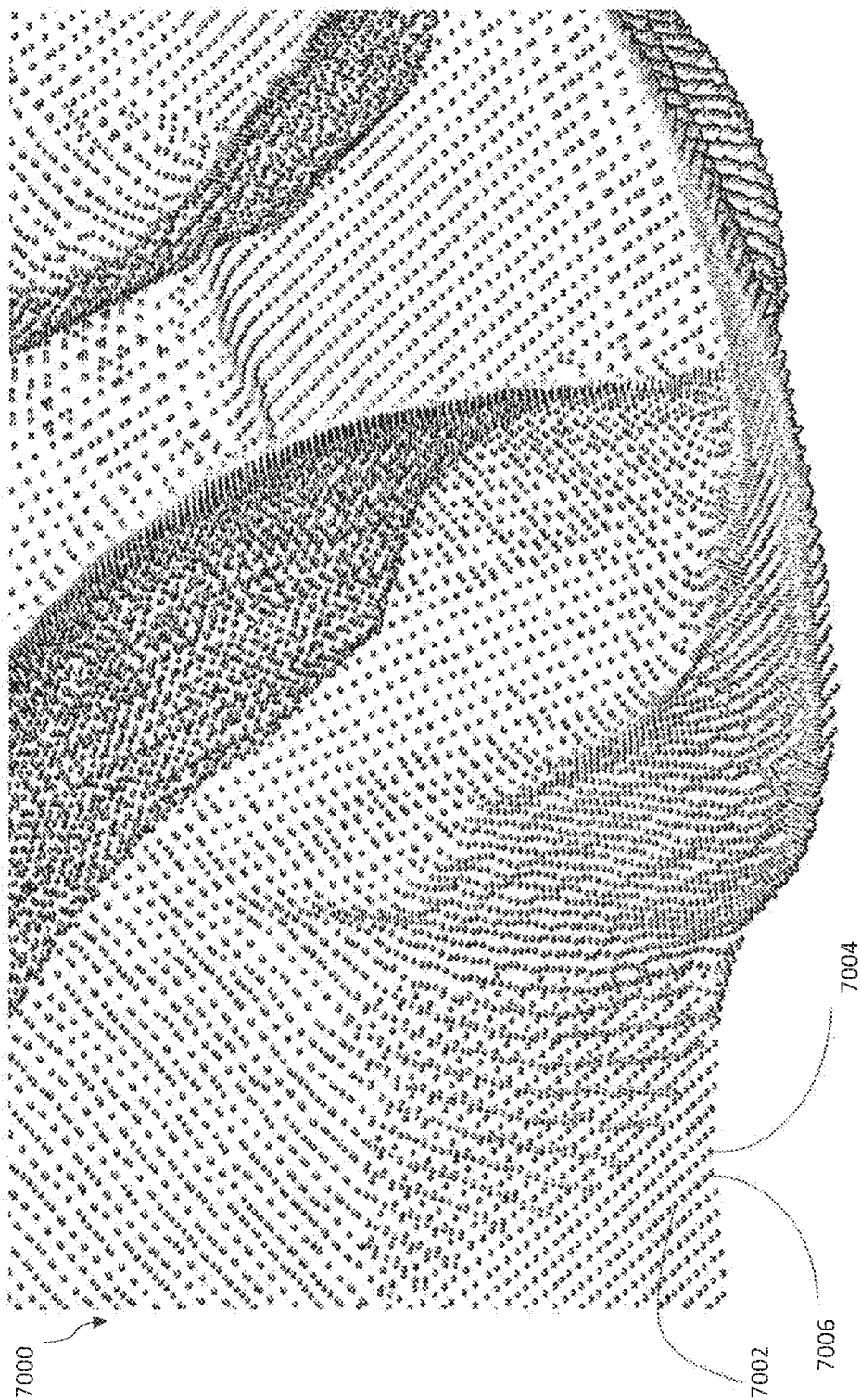
FIG. 11(a) is a perspective view of a point cloud.

FIG. 11(a) shows an example of a generated point cloud viewable on a display in some embodiments. Point cloud 7000 includes generated digital surface points such as digital surface point 7002 at every position of the selected iso-value of density in virtual 3D space.

Figure 11B:
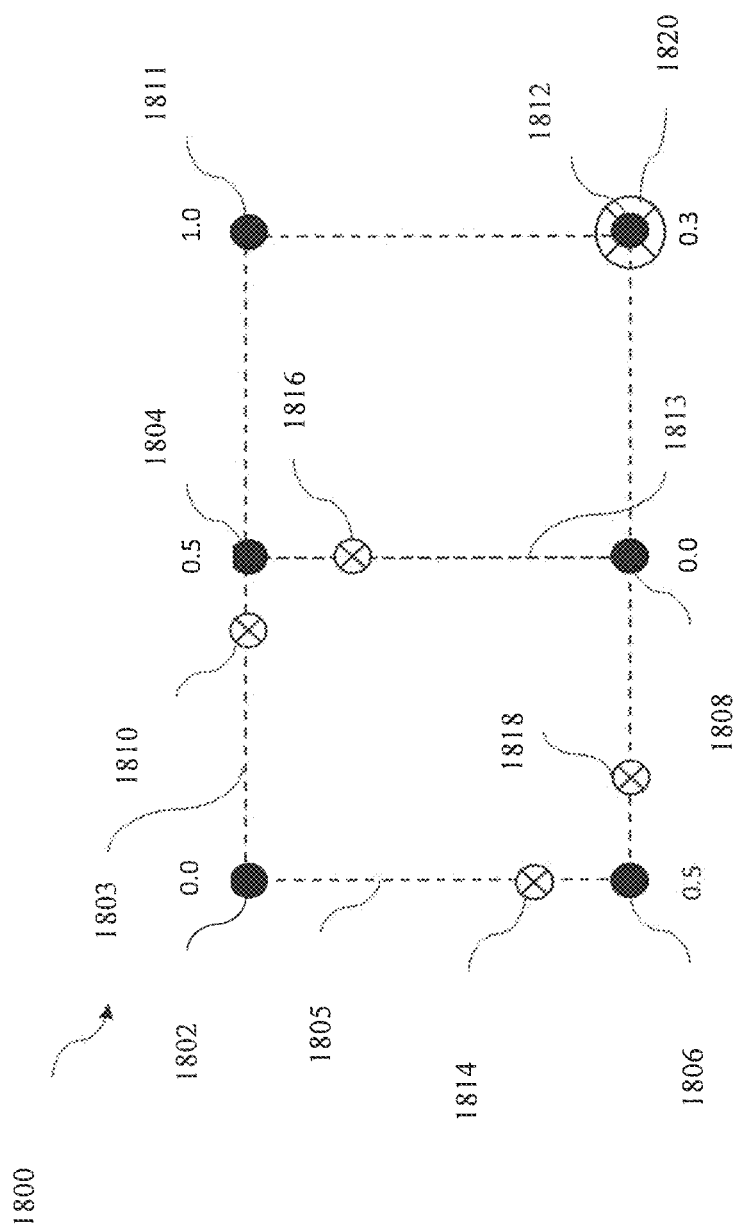
FIG. 11(b) is a perspective view of an example of a portion of a 3 dimensional volumetric density file depicted for simplicity in 2 dimensions.

FIG. 11(b) illustrates an example of generating digital surface points at particular positions in virtual 3D pace to generate a point cloud in some embodiments based on voxel positions in the volumetric density file. The figure illustrates a portion of a 3D volumetric density file depicted for simplicity in 2 dimensions. In the example, voxels 1802,

1804, 1806, 1808, 1811, and 1812 from the volumetric density file represent different density values of the CT scanned material in the volumetric density file. For example, voxels 1802 and 1808 indicate materials at their positions have a density of 0. This can, for example, represent air. In the example, voxels 1804 and 1806 indicate the material at their respective positions has a density of 0.5, voxel 1811, indicates material density at its position is 1.0, and voxel 1812 indicates a material density of 0.3 at its position.

In some embodiments of a computer-implemented method, the volumetric density file containing voxels is loaded, and each voxel is evaluated against a selectable iso-value of density. If the selected iso-value of density matches the density value at a voxel, then the computer-implemented method can generate one or more digital surface points and arrange the one or more digital surface points in the point cloud at a position that corresponds to or is in the neighborhood of the position of the voxel in the volumetric density file. In some embodiments of the computer-implemented method, if the selected iso-value of density falls between the density value of voxels, then the computer-implemented method can generate one or more digital surface points in the point cloud at position(s) corresponding to position(s) between the voxels along an edge connecting the voxels as further discussed below.

In the example figure, a selected iso-value of density of 0.3, for example, would fall between voxel 1802, which has a density of 0, and voxel 1804, which has a density of 0.5. One or more digital surface points can be generated at a position in the point cloud corresponding to a position 1810 in the volumetric density file between voxel 1802 and voxel 1804 along a voxel edge 1803. One or more digital surface points can also be generated and placed at a position in the point cloud corresponding to a position 1814 in the volumetric density file between voxel 1802 and voxel 1806 along their voxel edge 1805 since the selected iso-value of density (0.3) in the example also falls between the densities at voxels 1802 and 1806. In the example, no digital surface points are generated and placed at a position in the point cloud corresponding to the position in the volumetric density file between voxels 1804 and 1811 because the selected iso-value of density 0.3 does not fall between the values of voxel 1804 (0.5) and 1811 (1.0). One or more digital surface points can also be generated and placed at a position in the point cloud corresponding to a position 1816 in the volumetric density file between voxel 1804 and voxel 1808 along their voxel edge 1813 since the selected iso-value of density (0.3) in the example also falls between the densities at voxels 1804 and 1808. Since voxel 1812 has a density value matching the selected iso-value of density of 0.3, a digital surface point can be generated in the point cloud at the same corresponding position 1820 of the voxel 1812.

In some embodiments of the computer-implemented method, digital surface points that are generated for an iso-density value falling between voxels can be proportionately spaced in the point cloud between corresponding positions of voxels for which they are generated. For example, a selected iso-value of density of 0.3 is closer to density 0.5 of voxel 1806 than to density 0 of voxel 1802. The computer-implemented system can, for example, generate a digital surface point at position 1814 in the point cloud since position 1814 is proportionately closer to the corresponding position of voxel 1806 than to the position of voxel 1802 in the volumetric density file. A digital surface point is generated at position 1818 in the point cloud for an iso-density value of 0.3 since position 1818 is proportionally closer to the corresponding position of voxel 1806 with density 0.5 than the position of voxel 1808 with density 0. A digital surface point is generated at position 1810 in the point cloud for a selected iso-density value of 0.3 since position 1810 is proportionally closer to the corresponding position of voxel 1804 with density 0.5 than the position of voxel 1802 with density 0. A digital surface point is generated at position 1816 in the point cloud for a selected iso-density value of 0.3 since position 1816 is proportionally closer to the corresponding position of voxel 1804 with density 0.5 than the position of voxel 1808 with density 0, for example In some embodiments, the computer-implemented method can evaluate every voxel in the volumetric density file against the user-selected iso-value of density and generate one or more digital surface points in the point cloud as disclosed herein until no more voxels remain for evaluation in the volumetric density file.

FIG. 11(c) illustrates an example of a 2D depiction 18100 of a 3D point cloud 7000 with digital surface points 1830, 1834, 1836, 1838, and 1840 generated at positions in the point cloud corresponding to positions 1810, 1814, 1816, 1818, and 1820, respectively in the volumetric density file 1800 from FIG. 11(b) for an iso-value density of 0.3. As illustrated in the figure, only the digital surface points generated for a selected iso-value from the volumetric data file are included in the point cloud by the computer-implemented method. The computer-implemented method can save the generated digital point cloud 7000 to storage media. The computer-implemented method can in some embodiments, display and provide the generated point cloud 7000 to a user to view and/or manipulate.

In some embodiments the computer-implemented method reduces, the number of digital surface points in the point cloud 7000 from FIG. 11(a) through sampling, such as, for example, by selecting a subset of the digital surface points from the point cloud 7000 to provide a reduced point cloud. Selecting the subset of digital surface points from the point cloud 7000 can reduce the dataset size and complexity and simplify data structures and processing. In some embodiments, selecting the subset of the digital surface points from the point cloud can be performed by the computer-implemented method automatically.

In some embodiments of the computer-implemented method, point cloud 7000 can be reduced by selecting a desired level of distance between two or more digital surface points. In some embodiments, of the computer-implemented method, point cloud 7000 can be reduced by setting a minimum distance between digital surface points in the point cloud 7000. For example, during reduction of point cloud 7000, digital surface points can be specified not to be closer than a user-selectable distance. In some embodiments of the computer-implemented method, a minimum distance between points can be between 100 microns to 200 microns or less, for example. The minimum distance between points can be a user selectable value. The minimum distance between points can be initially set and then automatically applied during every surface selection thereafter, or can be selected on a per scan basis.

Figure 12A:
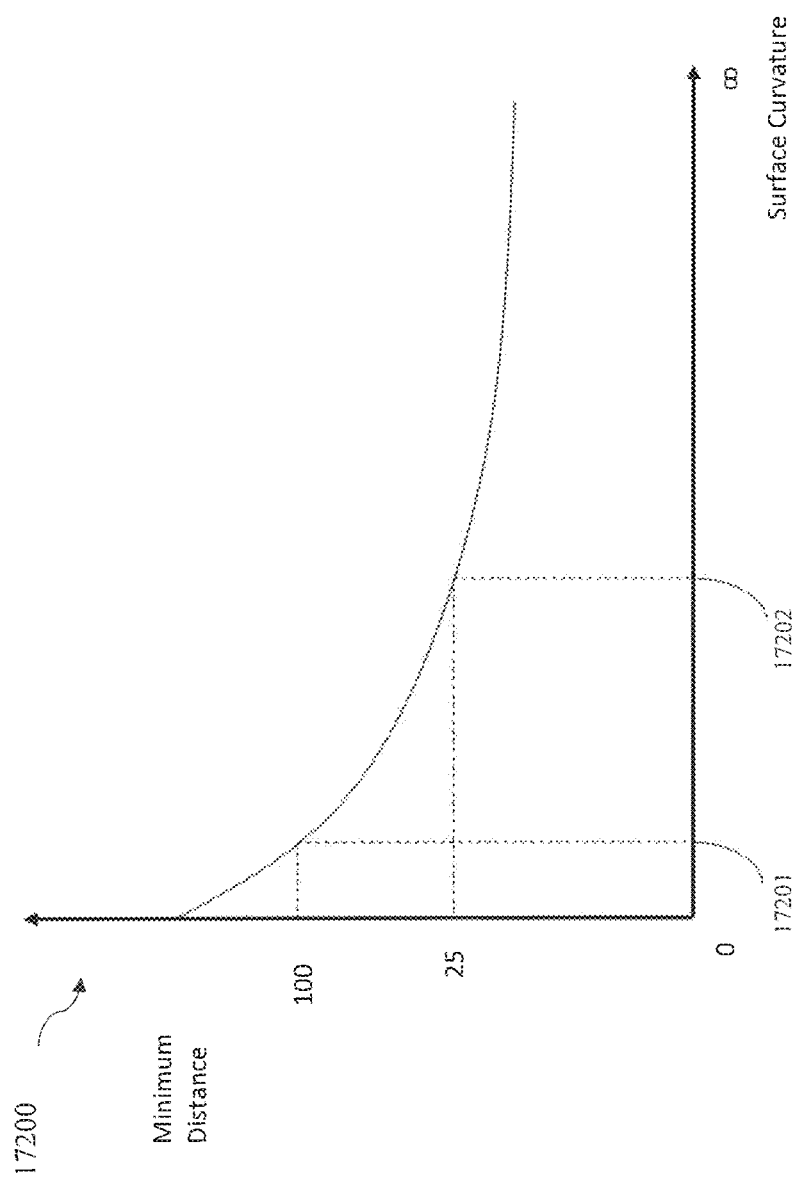
FIG. 12(a) is a graph illustrating a user selectable relationship between surface curvature and minimum distance.

In some embodiments of the computer-implemented method, the minimum distance can optionally be specified by a user to be a continuous function of surface curvature as illustrated in FIG. 12(a). In some embodiments, the computer-implemented method can load the point cloud and determine curvature by finding all the points in the neighborhood of a radius around each digital surface point, fitting a quadratic surface to the points in the neighborhood, and determining the module of mean curvature of that surface, for example. The computer-implemented method can be repeated for all points in the point cloud in some embodiments, for example.

In some embodiments, a computer-implemented method can alternatively determine curvature by loading a generated point cloud and for each digital surface point, finding all the points in the neighborhood of the radius around the digital surface point. The computer-implemented method can then determine a 3×3 covariance matrix for the coordinates of the points in the neighborhood. Next, the computer-implemented method can find all 3 eigenvalues of the covariance matrix, and finally approximate the curvature from the eigenvalues in some embodiments, e.g. minimal eigenvalue divided by the sum of eigenvalues or a monotone function of that fraction. This computer-implemented embodiment can account for zero mean curvatures for non-planar regions and can therefore be preferable in some embodiments, for example. The computer-implemented method can be repeated for all points in the point cloud in some embodiments, for example.

The radius of either method of determining curvature can be up to and including 60 digital surface points on average in the neighborhood of the digital surface point in the point cloud being evaluated, and can be a user selectable value. A selection of a smaller number of points and smaller radius can lead to faster computations, while selecting a larger number of points and larger radius can provide a more precise curvature estimation. The computer-implemented method can be repeated for all points in the point cloud, for example.

Once surface curvature is determined, the computer-implemented method can determine the minimum distance based on the particular amount of surface curvature. For example, FIG. 12(a) is a graph 17200 depicting a user-selectable relationship between surface curvature and minimum distance between digital surface points as an example. The computer-implemented method can determine the amount of surface curvature and then obtain the minimum distance between digital surface points based on the user selected relationship. In the example shown in FIG. 12(a), a digital surface region having a surface curvature value at 17201 can return a minimum distance of 100 microns between points for the digital surface region, for example. A greater surface curvature value at 17202 can return a minimum distance of 25 microns between points for the digital surface region, for example. In some embodiments, any digital surface points falling within the minimum distance of a digital surface point can be eliminated from the point cloud by the computer-implemented method. The computer-implemented method can be repeated for all points in the point cloud, for example.

In some embodiments of the computer-implemented method, minimum distance between points can be defined discretely rather than as a continuous function of surface curvature. For example, the minimum distance between digital surface points can be specified based on a curvature threshold of the digital surface. For example, curved digital surfaces having a surface curvature above a particular user-selectable value can have a user-selectable minimum distance between digital surface points that is lower than that of digital surface regions having a surface curvature below the threshold user-selectable curvature value.

In some embodiments of the computer-implemented method, the minimum distance between points can be reduced up to ¼ of the original distance, for example, based on curvature. For example, where the distance between digital surface points may be set to 100 microns, it can be reduced by the user to 25 microns between digital surface points, thereby increasing the number of digital surface points on the curved surface region(s). In some embodiments of the computer-implemented method, the minimum distance between digital surface points on a curved digital surface region can be a user selectable value, the distance can be initially set and then automatically applied during surface selection, and/or the minimum distance between digital surface points along one or more curved surface regions may be set independently with respect to other surfaces.

In some embodiments, if the digital surface point does not fall within the sampling/reduction criterion, then the digital surface point is eliminated from the point cloud. For example, if a minimum distance between digital points in the cloud is set and one or more neighboring digital surface point(s) fall within the minimum distance between digital surface points, then the computer-implemented method can eliminate the one or more digital surface points from the point cloud. If, however, one or more neighboring digital surface points fall outside of the minimum distance, then the one or more neighboring digital surface points are retained in the point cloud.

As an example, the computer-implemented method can load a point cloud and for each digital surface point determine one or more neighboring digital surface points within a radius from a generated point cloud. The radius in some embodiments can be up to and including 60 digital surface points in the neighborhood of the digital surface point in the point cloud being evaluated, and can be a user selectable value. An amount of curvature for the first and one or more neighboring digital surface points can be determined by the computer-implemented method as discussed previously. In some embodiments, the amount of surface curvature can be zero, or close to zero, indicating a flatter digital surface. In some embodiments, the amount of curvature can be greater than zero. In some embodiments, the computer-implemented method can determine a minimum distance between each digital surface point and the one or more neighboring digital surface points based on the amount of curvature between them. If the minimum distance between digital surface points is specified, then the computer-implemented method can determine whether the neighboring digital surface point(s) fall(s) within the specified minimum distance between digital surface points. If any of the one or more neighboring digital surface point falls within the minimum distance specified, then those neighboring digital surface points can be eliminated from the point cloud by the computer-implemented method. If the neighboring digital surface point falls outside of the minimum distance specified for surface curvature or no minimum distance is specified, then the one or more neighboring digital surface point(s) is/are retained in the point cloud.

In some embodiments of the computer-implemented method, if the first and neighboring digital surface point are on a curved digital surface based on a threshold curvature value, then the computer-implemented method can determine whether a minimum distance between digital surface points is specified. If the minimum distance between digital surface points is specified, then the computer-implemented method can determine whether the neighboring digital surface point falls within the specified minimum distance between digital surface points. If the neighboring digital surface point falls within the minimum distance specified, then the computer-implemented method can eliminate it from the point cloud. If the neighboring digital surface point falls outside of the minimum distance or the minimum distance is not specified for curved surfaces, then the computer-implemented method can retain it in the point cloud. If the computer-implemented method determines that the first and neighboring digital surface points are not on a surface curvature, then the computer-implemented method can determine whether the minimum distance between digital surface points for non-curved surfaces (i.e. flatter surfaces or surfaces whose curvature is below the threshold value for curvature) is specified. If the minimum distance between digital surface points is specified, then the computer-implemented method compares whether the neighboring digital surface point falls within the minimum distance between digital surface points for flatter surfaces. If the neighboring digital surface point falls within the minimum distance, then the computer-implemented method eliminates it from the point cloud. If the neighboring digital surface point falls outside of the minimum distance or a minimum distance between digital surface points for flatter surfaces is not specified, then the computer-implemented method retains the neighboring digital surface point in the point cloud.

Figure 12B:
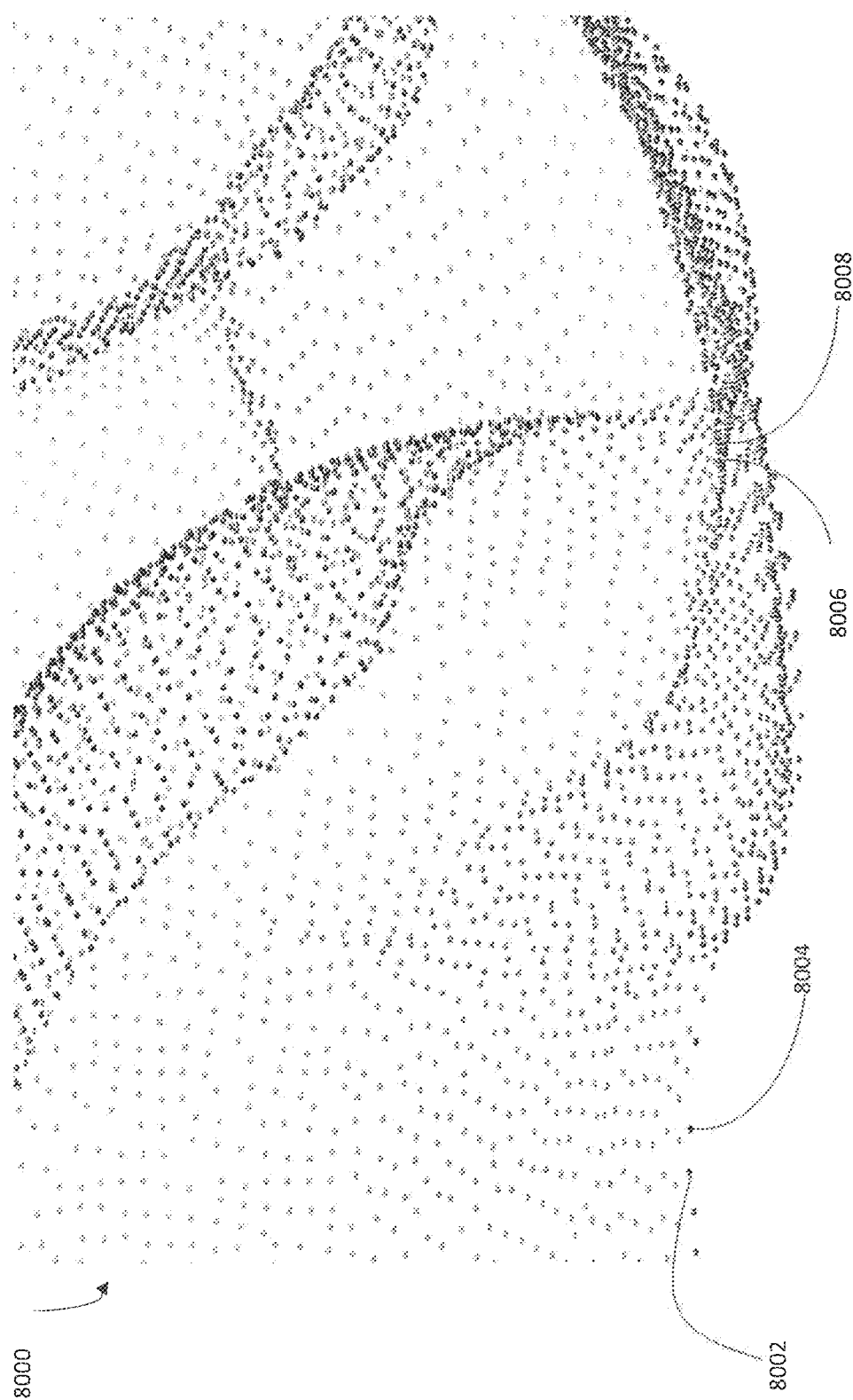
FIG. 12(b) is a perspective view of a reduced point cloud.

FIG. 12(b) illustrates a post-sampling reduced point cloud 8000 of point cloud 7000 having fewer digital surface points than the point cloud 7000 from FIG. 11(a). As shown in the example of FIG. 12(b), digital surface points 8002 and 8004 are spaced further apart than digital surface points 7004 and 7006 from FIG. 11(a), and intermediate digital surface points are not present in the post-sampling point cloud 8000 of FIG. 12(b). Also illustrated in the example of post-reduction point cloud 8000 are digital surface points 8006 and 8008 located on a curved surface. As discussed previously, this arrangement of digital surface points and the number of digital surface points on the curved surface in the reduced point cloud 8000 may result from either setting a minimum distance between digital surface points and/or setting a different minimum distance between digital surface points on curved surfaces versus non-curved or reduced-curvature/flatter surfaces in some embodiments of the computer-implemented method.

One advantage of sampling the point cloud prior to generating the digital surface mesh is to increase speed and reduce the data set and data structure complexity of any subsequent triangulation step by reducing the number of digital surface points to be triangulated, for example. This can, for example, increase processing speed and reduce the amount of storage necessary to process CT scans. This can increase the accuracy and efficiency of generating the digital surface mesh, as described below, for example.

Figure 15:
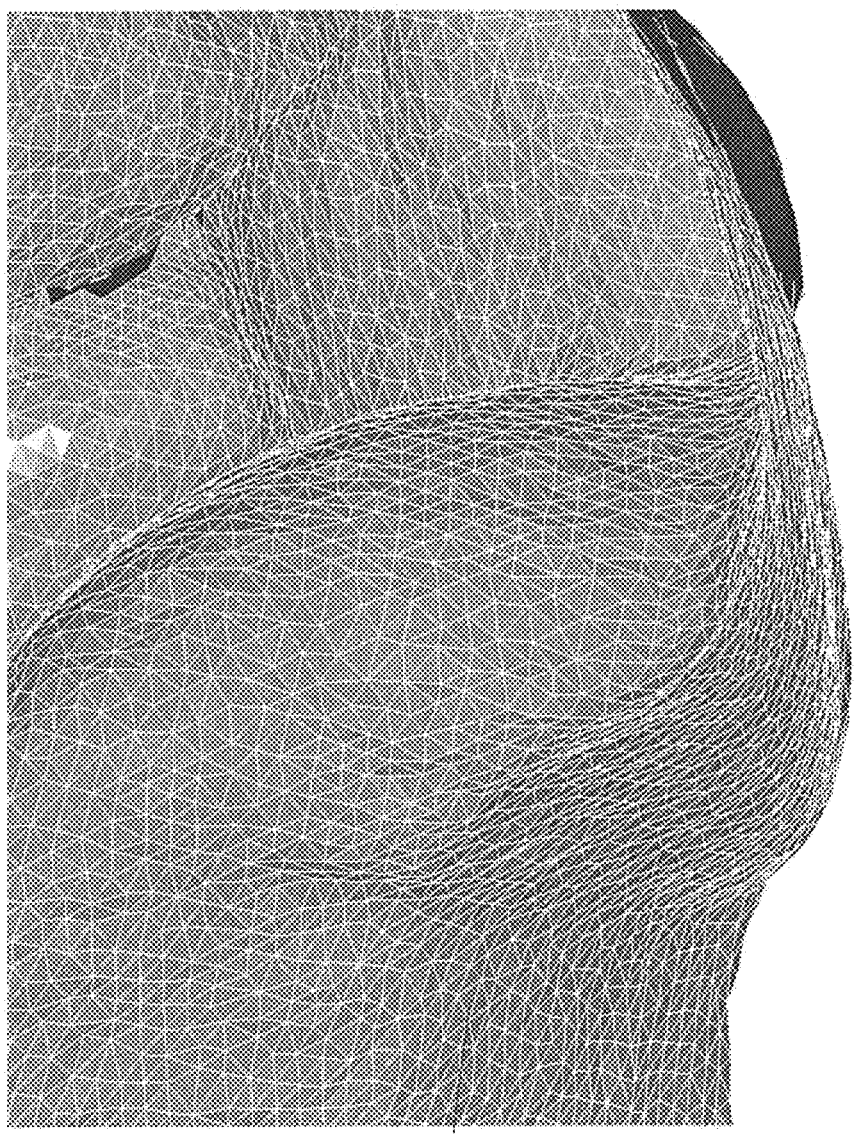
FIG. 15 is a perspective view of a digital model illustrating a triangulated digital surface mesh.

In some embodiments of the computer-implemented method, triangulation can be performed on the reduced point cloud 8000 to create digital surface mesh 9000 shown in FIG. 15, for example. This triangulation can in some embodiments of the computer-implemented method utilize Delaunay triangulation known in the art to create digital surface mesh 9000. The digital surface mesh 9000, however generated, is an interconnected network of triangles defining part or all of a surface of the physical dental impression 2000. In some embodiments, triangulation can be performed by the computer-implemented method automatically.

Figure 13:
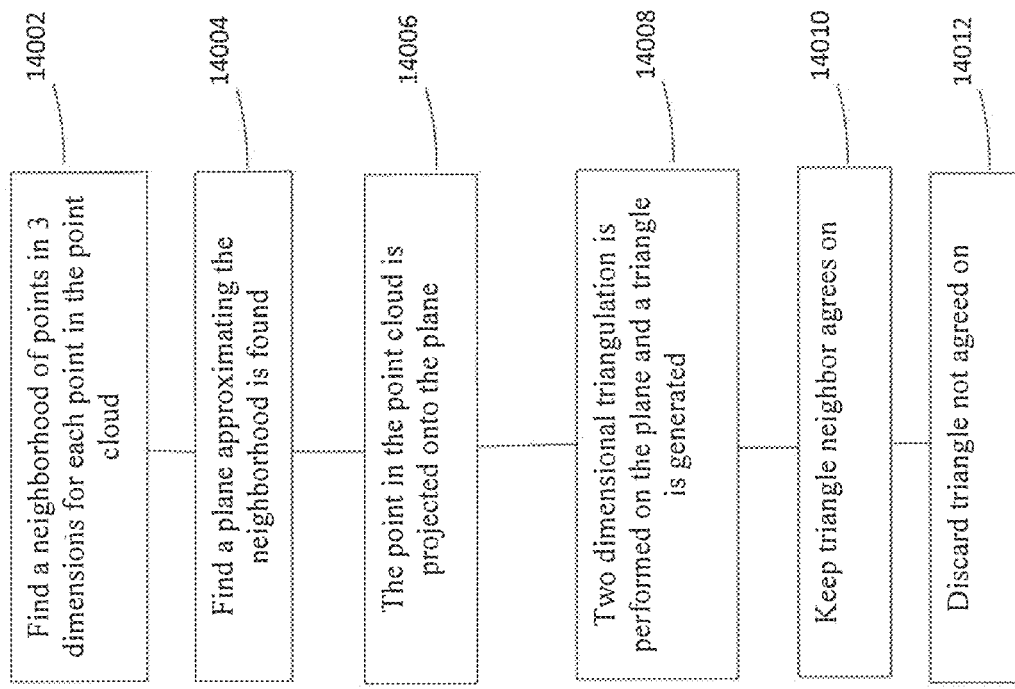
FIG. 13 illustrates a method of triangulation in some embodiments.

In some embodiments of the computer-implemented method, as illustrated in FIG. 13, triangulation can include finding a neighborhood of digital surface points in three dimensions for each digital surface point in the point cloud 8000 at 14002. In some embodiments, the neighborhood of digital surface points can be a user selectable radius up to and including 20 points. As an example, a plane approximating the neighborhood is found at 14004 by the computer-implemented method. The digital surface point in the point cloud 8000 is then projected onto the plane at 14006 to determine the ordering of neighboring points by the computer-implemented method. Three dimensional triangulation is performed and a triangle is generated at 14008 by the computer-implemented method. If the neighborhood agrees the triangle should be kept, then it is retained at 14010 by the computer-implemented method. Otherwise, the triangle is discarded at 14012 by the computer-implemented method. Triangulation of the reduced point cloud 8000 can produce a digital surface mesh with non-degenerate triangles. In some embodiments, each triangle can be close to an equilateral triangle, thereby generating a more accurate digital surface mesh. The computer-implemented method can be repeated for each point in the point cloud.

Figure 14:
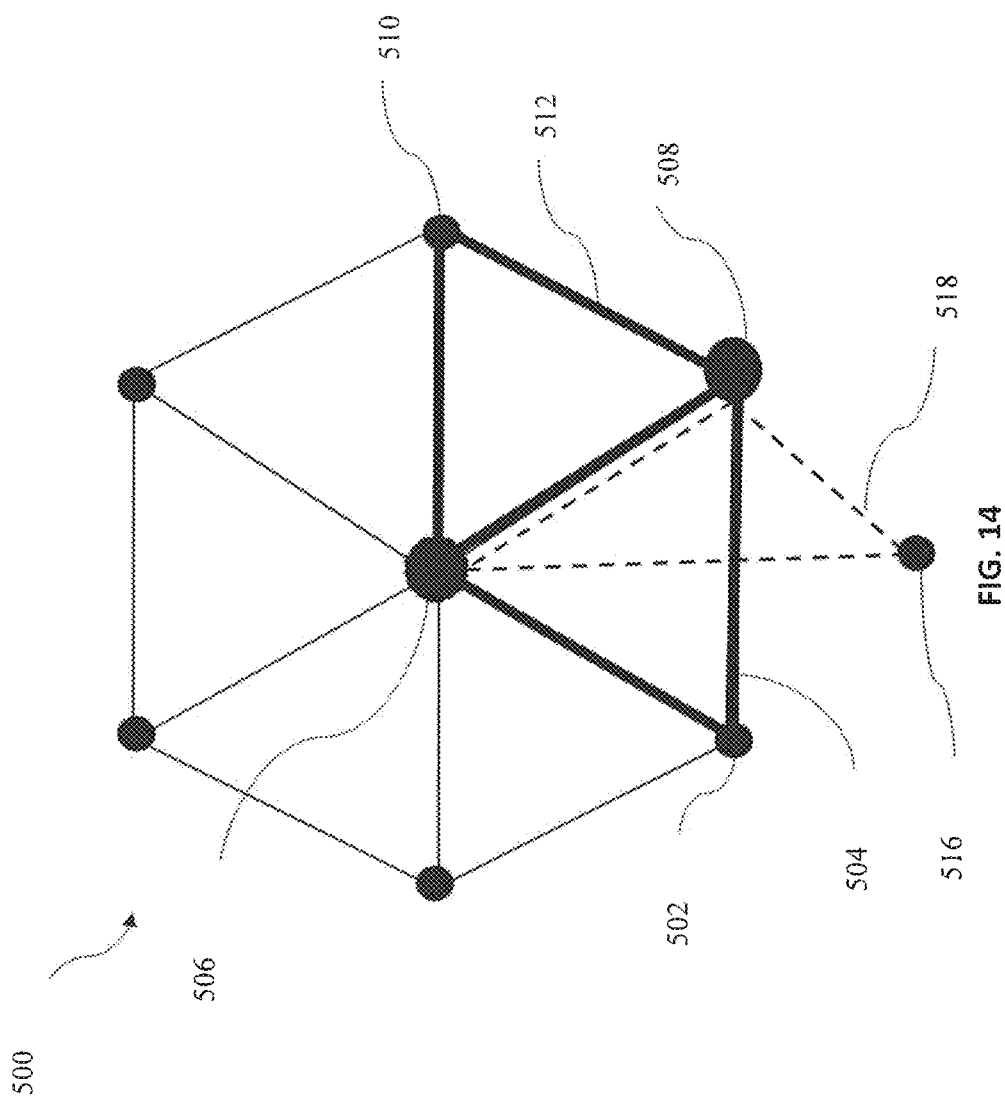
FIG. 14 is a perspective view of an example of triangulation of a point cloud.

FIG. 14 illustrates one example of triangulation in some embodiments of the computer-implemented method. Reduced point cloud 500 includes digital surface points 502, 506, 508, 510, and 516, for example, among other digital surface points. During triangulation in some embodiments of the computer-implemented method, a digital surface point is chosen and connected with its neighbors to create triangles that form a digital surface mesh. For example, digital surface point 506 is chosen and connected with its neighboring digital surface points 502 and 508 to form triangle 504. Digital surface point 506 is also connected with neighborhood digital surface points 508 and 510 to create triangle 512. Other triangles are similarly created by connecting other neighborhood digital surface points to digital surface point 506 as shown in FIG. 14. Once triangles are generated for one digital surface point, a new digital surface point is chosen, and triangles connecting the new digital surface point to its surrounding digital surface points are generated in some embodiments of the computer-implemented method. In the example shown in FIG. 14, new neighboring digital surface point 508 is chosen, for example, and connected to digital surface points 506 and 510 to create triangle 512. New digital surface point 508 is also, for example, connected to digital surface points 506 and 502 to create triangle 504. These triangles 504 and 512 created with chosen digital surface point 508 overlap with the triangles created when digital surface point 506 was the chosen digital surface point. Since the chosen digital surface points 506 and 508 agree on these triangles, the triangles are retained. Chosen digital surface point 508 also connects with its neighborhood digital surface points 506 and 516 to create triangle 518. Since triangle 518 was not generated when 506 was the chosen digital surface point, chosen digital surface points 506 and 508 do not agree on this triangle. The triangle can, in some embodiments of the computer-implemented method, be dropped and no digital surface mesh is created with triangle 518. The computer-implemented method can be repeated for each point in the point cloud.

FIG. 15 illustrates an example of a reduced point cloud that has been triangulated to create a digital surface mesh 9000. Triangulation of the reduced point cloud as described in this disclosure can generate a digital surface mesh 9000 of non-degenerate triangles 9002 in some embodiments of the computer-implemented method. Each of the triangles—such as triangle 9002—are close to equilateral.

Another example of creating a digital surface mesh is a conventional technique called marching cubes. An example of marching cubes is described in SYSTEM AND METHOD FOR THE DISPLAY OF SURFACE STRUCTURES CONTAINED WITHIN THE INTERIOR REGION OF A SOLID BODY, U.S. Pat. No. 4,710,876 assigned to General Electric Co., the entirety of which is hereby incorporated by reference. In one embodiment, the computerimplemented-method can implement conventional marching cubes by evaluating eight neighboring voxels of a given voxel to determine which voxels will contain a surface. Each given voxel can include an 8 bit integer representing each of the voxel's neighboring voxels. For the given voxel, the computer-implemented-method can compare each neighboring voxel value to the selected iso-value to determine whether the voxel falls within the cube defined by the neighboring voxels. If the computer-implemented method determines that the neighboring voxel value is greater than the selected iso-value, then the bit in an 8 bit integer corresponding to that neighboring voxel is set to one by the computer-implemented method. If the computer-implemented method determines that the neighboring voxel is less than the selected iso-value, then the corresponding bit is set to zero by the computer-implemented method. The resulting 8 bit integer after evaluation of all neighborhood voxels can be used as an index to select one or more predetermined polygon surfaces by the computer-implemented method as illustrated in FIGS. 1 and 2, FIGS. 3A through 3N, FIGS. 4A through 4N, FIGS. 4A' through 4N', FIG. 4B", and Tables 1 and 2 of U.S. Pat. No. 4,710,876, for example. Vertices of the polygon surfaces can be located along its respective edge based on linearly interpolating the voxels connected by the edge. A normal of each vertex can be interpolated by the computer-implemented method based on the gradient of the voxel. Other variants of marching cubes may also be utilized.

Figure 17:
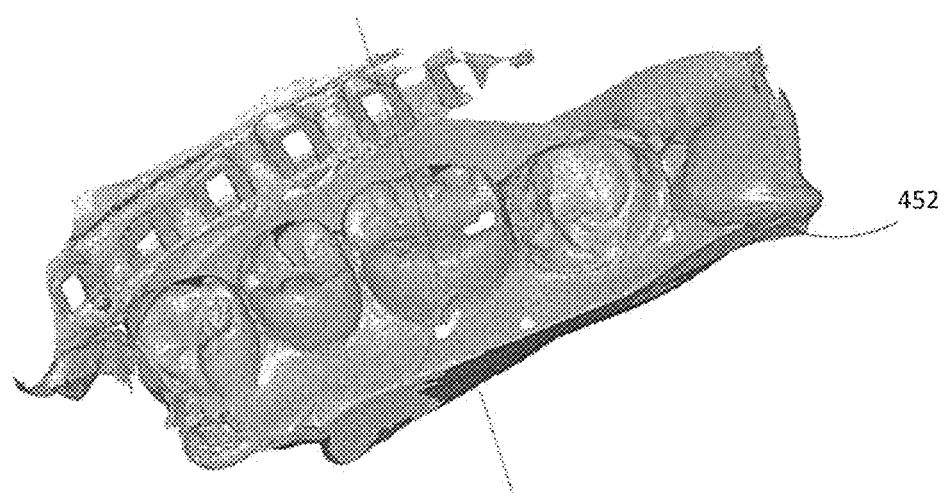
FIG. 17 is a 3-dimensional (3D) view of a digital model of a portion of a first jaw.
Figure 18:
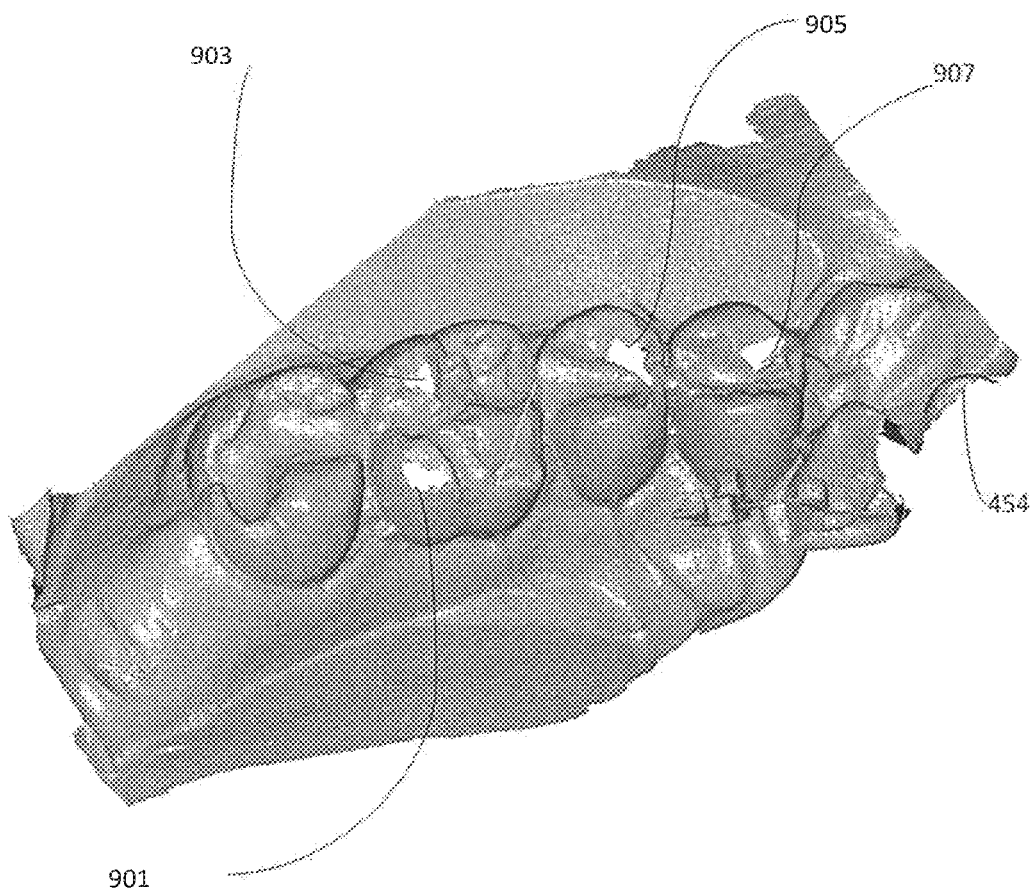
FIG. 18 is a 3-dimensional (3D) view of a digital model of a portion of a second jaw.

FIG. 16 shows a single digital dental impression 352 with both first and second jaws. Upon processing, the single digital dental impression 352 can be digitally split into a digital model of a first side such as first jaw 452 for example and optionally a digital model of a second side such as second jaw 454 for example as shown in FIG. 17 and FIG. 18, respectively. In some embodiments, the digital splitting occurs automatically, without user intervention. In some embodiments, the digital splitting can be performed by a user selecting a user interface element to initiate the digital splitting.

Direction Determination

Some features as indicated in the present disclosure may require directions to be determined in the digital model. In some embodiments, the computer-implemented method receives a digital model and determines one or more directions in the digital model. Some embodiments include generating one or more rays along the one or more directions in the digital model. In some embodiments, direction determination and/or ray generation can be performed by the computer-implemented method automatically. The computer-implemented method can determine the directions using any method. For example, several methods are described in the article "Four Ways to Create a Mesh for a Sphere" by Oscar Sebio Cajaraville, dated Dec. 7, 2015, which is hereby incorporated by reference in its entirety. The method described herein is an example for illustrative purposes.

Figure 19A:
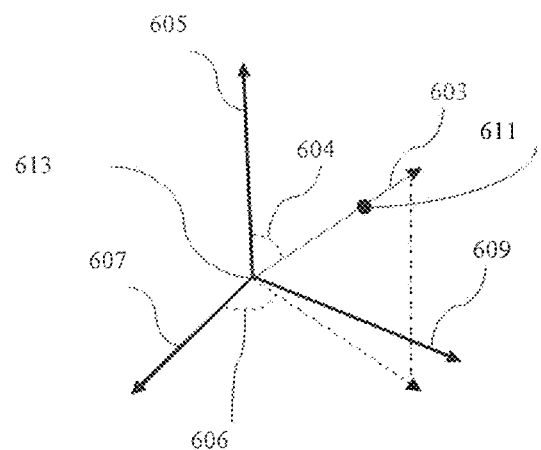
FIGS. 19(a), 19(b), and 19(c) are illustrations of determining one or more directions.
Figure 19B:
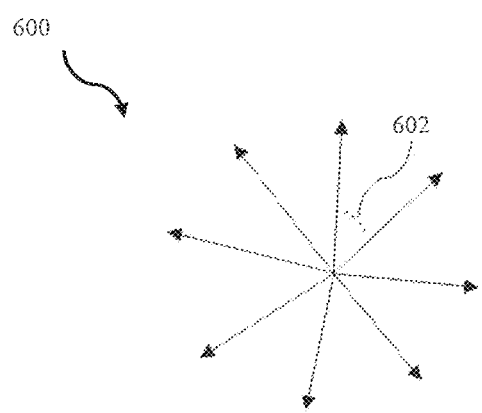

In one embodiment, the computer-implemented method can receive a digital model determine directions as illustrated in FIG. 19(a). FIG. 19(b) illustrates directions 600. In some embodiments, a user-selectable angle 602 between the directions 600 can be 5 degrees, for example. However, a greater or smaller angle between directions can be used, and can be adjusted by the user.

FIG. 19(a) illustrates an example in some embodiments of determining one or more directions. For example, direction 603 forms angle 604 with axis 605 and angle 606 with axis 607. The computer-implemented method can increment the angles 604 and 606 to determine directions in 360 degrees in the digital model. For example, the angle 604 can be incremented in some embodiments from 0 to 180 by 10 degrees and the angle 606 can be incremented from 0 to 360 by 20 degree increments. In some embodiments, the angles 604 and 606 can be incremented by any amount. The figure illustrates coordinate axes 607, 609, and 605, which can correspond, for example, to the x-y-z axes, respectively. Also illustrated in the figure is an example direction 603 formed by an angle a 604 with respect to the z-axis 605 and an angle b 606 between the x-axis 607 and the projection on to the x-y plane. In one embodiment, the computer-implemented method can determine directions based on the angle a 604 and angle b 606 as follows:

```
StepA=pi/(NA)
StepB=2*pi/(NB)
for i=0, i < NA; i++
  { a=i*StepA
      for k=0; k< NB; k++
      {
        b=k* StepB;
        x = sin(a)cos(b);
        y = sin(a)sin(b);
        z - cos(a)
      }
  }
``` where NA and NB are user-selectable values, and NA is the number of steps of A and NB is the number of steps of B. In some embodiments NA and NB can be a user selectable value. In some embodiments, NA and NB can be between 20 to 100. The x, y, z coordinates can represent a position 611 in space through which one or more directions originate from the origin 613.

Figure 19C:
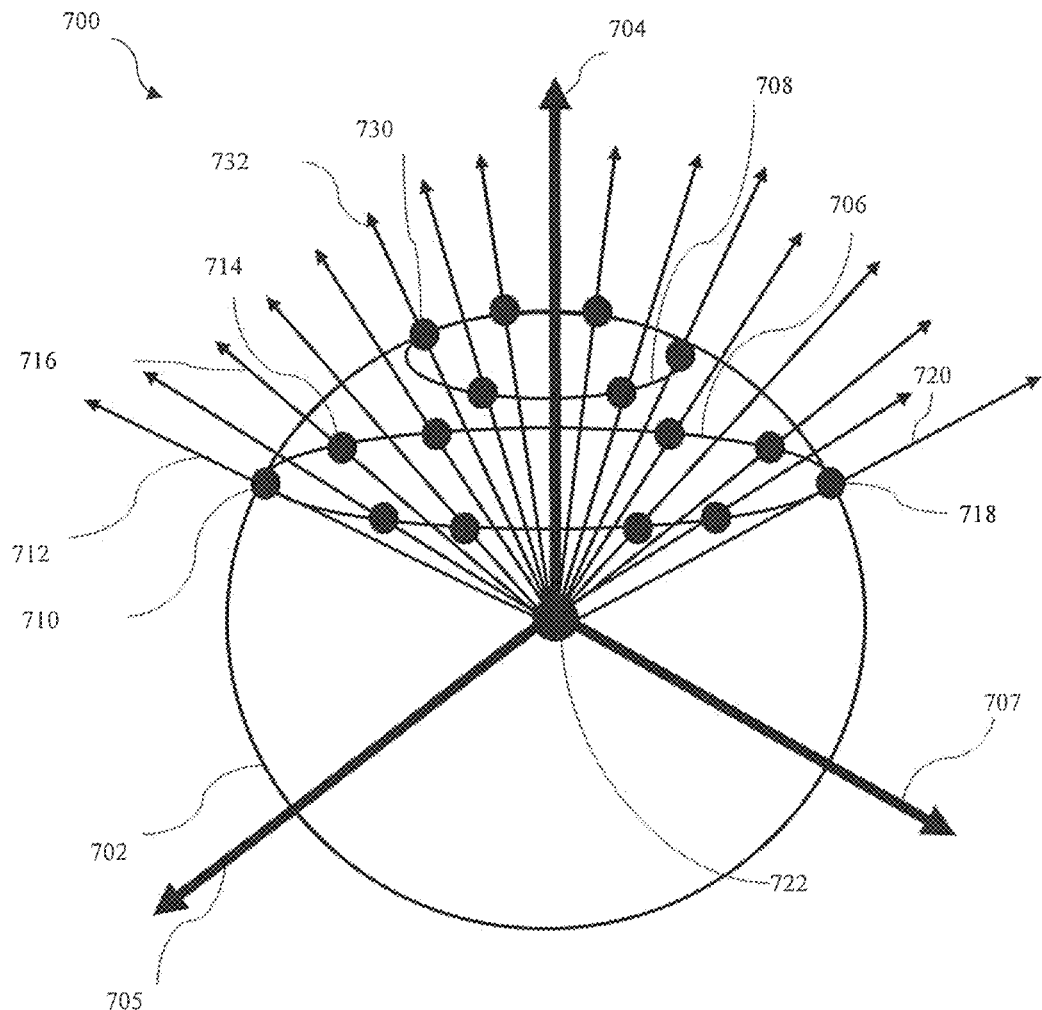

FIG. 19(c) illustrates an example of determining directions in the digital model as described herein. A unit sphere 702 includes axes 704, 705, and 707 and origin 722. Based on the user-selectable values of NA and NB, the computer-implemented method can determine several directions in the digital model. In some embodiments, the value of NB can determine the number of coordinate points through which directions are generated from the origin in a circle. In some embodiments, the value of NA can determine the number of circles. For example, the computer-implemented method can initially determine coordinate point 730 and generate a direction 732 from origin 722 through the coordinate point 730. The computer-implemented method can generate additional coordinate points in a circle 708 and determine directions through each coordinate point from the origin 722. In some embodiments, the number of coordinate points can be determined by the user-selectable value of NB. The computer-implemented method can next determine coordinate points in a circle 706 and determine directions through the coordinate points. For example, the computer-implemented method can determine direction 712 from the origin 722 through the coordinate 710 and direction 720 through coordinate point 718. The computer-implemented method can determine direction 716 through the next coordinate point 714. The computer-implemented method can determine directions through coordinate points on circle 706. An angle between the directions 712 and 720 can define the aperture (also referred to herein as the "cone aperture"). FIG. 19(c) shows coordinate points, directions, circles, and apertures for illustrative purposes only; more or fewer coordinate points, directions, circles, and apertures are contemplated. The computer-implemented method can provide the directions and/or rays generated to determine different features of the digital model as described below.

Surface Visibility

Some features as indicated in the present disclosure may require determining surface visibility of surface regions in the digital model. In some embodiments, the computer-implemented method can determine visibility of surface regions in a digital model. Surface visibility can be determined using any technique including but not limited to z-buffering. In some embodiments, surface visibility can be determined by the computer-implemented method automatically. One method is described herein as an example.

Figure 20:
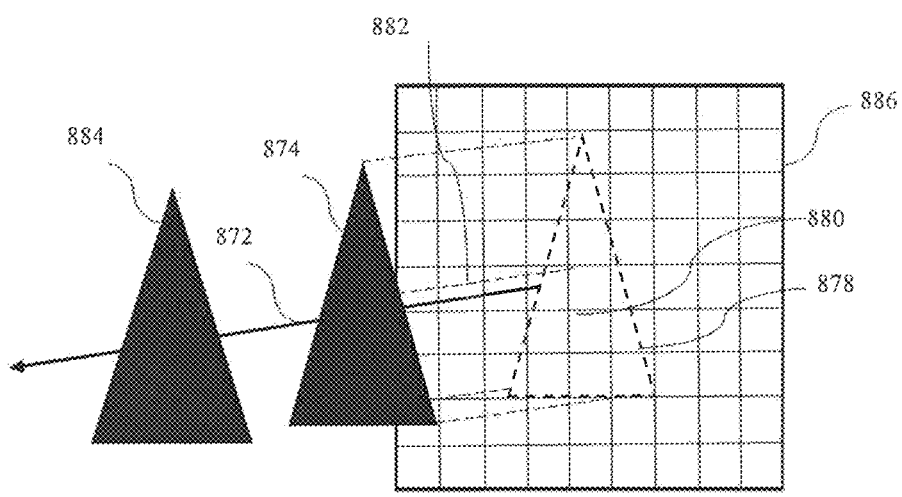
FIG. 20 is an illustration of determining surface visibility.

As illustrated in FIG. 20, for example, the computer-implemented method can receive a digital model and project a digital surface triangle 874 of the digital model onto a pixel grid 886 that is perpendicular to a direction 872 to generate a projected triangle 878. The computer-implemented method determines pixels 880 bounded by projected triangle 878 as belonging to the triangle 874, along with its distance from the grid (z-depth) 882 along direction 872. The computer-implemented method can determine the triangle 874 is visible from direction 872. The computer-implemented method can repeat this process for every triangle of the digital model to determine visible surface triangles.

If another triangle along the direction 872 has a shorter z-depth, then the computer-implemented method projects that triangle on to the pixel grid 886 instead. For example, as illustrated in FIG. 20, triangle 884 is along the direction 872. However, triangle 874 is also along the direction 872 and has shorter z-depth 882. The computer-implemented method projects triangle 874 onto the pixel grid 886 instead of triangle 884. The computer-implemented method also stores the z-depth value of the triangle 874 along with the pixels 880.

Curvature Determination

Some features as indicated in the present disclosure may require curvature determination of digital surface regions in the digital model. In some embodiments, the computer-implemented method can receive a digital model and determine curvatures of digital surface regions. The computer-implemented method can determine curvature of digital surface regions using any technique. In some embodiments, curvature determination can be performed by the computer-implemented method automatically.

In some embodiments, the digital surface regions include triangles. The curvature of a triangle can be determined by taking an average of the curvature of the triangle's edges, or an average of the curvature of the triangle's vertices.

Figure 21:
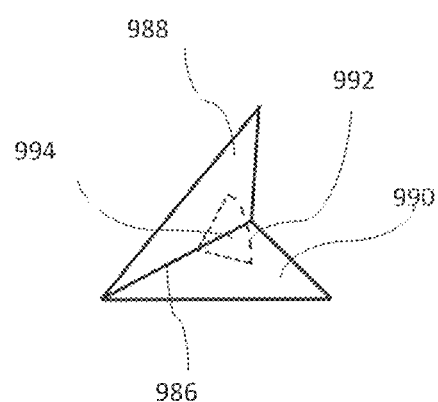
FIG. 21 is an illustration of curvature determination.

In some embodiments, the computer-implemented method can determine the curvature of the triangle by taking an average of the curvature of its edges. FIG. 21 illustrates one example of determining curvature at an edge 986 connecting two triangles 988 and 990. In some embodiments, the computer-implemented method can determine the curvature at edge 986 based on a dihedral angle 992 formed at the edge 986 between a particular triangle 990 and its adjacent neighborhood triangle 988 in the digital surface mesh as illustrated. The dihedral angle 992 can be determined by the computer-implemented method as an angle formed between the two adjacent triangles 988 and 990 in a third plane 994 that is perpendicular to the edge 986 formed by the two adjacent triangles 990 and 988. For example, in some embodiments, the computer-implemented method can take the sin ($\varphi$), where $\varphi$ is a dihedral angle 992 between two adjacent triangles 990 and 988. The computer-implemented method can repeat this curvature function at all triangle edges.

Alternatively, in some embodiments, the computer-implemented method can determine the curvature of the triangle by taking an average of the curvature of the triangle's vertices. For example, in some embodiments, the computer-implemented method can determine curvature at each vertex P by selecting a neighborhood of vertices (size N) around P, optionally using connection information to decrease the search space. The computer implemented method can fit a quadric patch $F(x,y,z)=0$ onto the neighborhood of points. The computer implemented method can determine a projection $P_0$ of P onto the patch, such that $F(P_0)=0$. The computer-implemented method can determine the curvature properties of F at $P_0$ and assign the curvature properties to P.

In some embodiments, the computer-implemented method can, for example, use quadric form $ax^2+by^2+cz^2+2exy+2fyz+2gzx+2lx+2my+2nz+d=0$ since each datum (x,y,z) will not lie perfectly on the surface of F. The computer-implemented method can determine the coefficients of the patch surface (a, b, c, e, f, g, l, m, n, d), from a 10×10 real symmetric eigenproblem of the form $A=D^TD$, where $D_i$ is the N×10 design matrix, each row of which is built up by $[x_i^2\ y_i^2\ z_i^2\ x_iy_i\ y_iz_i\ x_iz_i\ x_i\ y_i\ z_i\ 1]$, where i=1, . . . , N. The matrix can have 10 real eigenvalues and 10 corresponding eigenvectors. The coefficients of the eigenvector corresponding to the smallest eigenvalue $\lambda_1$ are the coefficients a, b, c, e, f, g, l, m, n, d of the quadric surface that best approximates the point cloud locally around P. The computer-implemented method uses a, b, c, e, f, g, l, m, n to determine values E, F, G, L, M, N by letting $F(x,y,z)=ax^2+by^2+cz^2+exy+fyz+gxz+lx+my+nz+d=0$, an implicit quadric surface in $R^3$, so that first order partial derivatives are $F_x=2ax+ey+gz+l$, $F_y=2by+ex+fz+m$, and $F_z=2cz+fy+gx+n$. The coefficients E, F, G are determined as $E=1+F_x^2/F_z^2$, $F=F_xF_y/F_z^2$, and $G=1+F_y^2/F_z^2$. Since second order partial derivatives are $F_{xx}=2a$, $F_{yy}=2b$, $F_{zz}=2c$, $F_{xy}=F_{yx}=e$, $F_{yz}=F_{zy}=f$ and $F_{xz}=F_{zx}=g$ and the magnitude of the gradient is $|\nabla F|=\sqrt{F_x^2+F_y^2+F_z^2}$, then coefficients L, M, N of the Second Fundamental Form are:

$$L = \frac{1}{F_z^2|\nabla F|}\begin{vmatrix} F_{xx} & F_{xz} & F_x \\ F_{zx} & F_{zz} & F_z \\ F_x & F_z & 0 \end{vmatrix},$$

$$M = \frac{1}{F_z^2|\nabla F|}\begin{vmatrix} F_{xy} & F_{yz} & F_y \\ F_{zx} & F_{zz} & F_z \\ F_x & F_z & 0 \end{vmatrix},$$

$$N = \frac{1}{F_z^2|\nabla F|}\begin{vmatrix} F_{yy} & F_{yz} & F_y \\ F_{zy} & F_{zz} & F_z \\ F_y & F_z & 0 \end{vmatrix}$$

The computer-implemented method then determines matrices A and B from E, F, G, L, M, N as:

$$A = \begin{bmatrix} L & M \\ M & N \end{bmatrix} \text{ and } B = \begin{bmatrix} E & F \\ F & G \end{bmatrix}$$

and determines principle curvatures $k_1$ and $k_2$ as the eigenvalues of the matrix $B^{-1}*A$.

The computer-implemented method can apply a selected scalar function to the principal curvatures $k_1$ and $k_2$ to determine the selected curvature function ("SCF"). For example, for principle curvatures $k_1$ and $k_2$, the computer-implemented method can determine Gaussian curvature (K) as $K=k_1 k_2$ or mean curvature (H) as $H=\frac{1}{2}(k_1+k_2)$.

The radius of either method of determining curvature can be up to and including 60 digital vertices on average in the neighborhood of the vertex being evaluated, and can be a user selectable value. A selection of a smaller number of points and smaller radius can lead to faster computations, while selecting a larger number of points and larger radius can provide a more precise curvature estimation. The computer-implemented method can be repeated for all vertices of the digital surface mesh, for example.

Occlusion Axis

Some embodiments include determination of an occlusion axis of the digital dental impression. For example, digitally splitting the single digital dental impression can include determining an occlusion axis. The occlusion axis is orthogonal to a biting surface, and is the direction from each jaw to the other. In some embodiments, the occlusion axis is provided in the digital model. In some embodiments, the computer-implemented method can receive the single digital dental impression and automatically determine the occlusion axis of an arbitrarily oriented digital dental impression that includes bite information.

In some embodiments, the computer-implemented method can automatically determine the occlusion axis by first calculating a least squares plane on the entire digital surface and then determining a normal orthogonal to least squares plane as the occlusion axis. In some embodiments, the least squares plane can be determined by the computer-implemented method by first determining a set of points such as either all vertices or centers of all faces of the digital surface mesh, for example. The computer-implemented method can assign a "weight" (or "mass") to each point. For example, the computer implemented method can set the weight of every vertex of the digital surface mesh equal to 1. Alternatively, the computer-implemented method can set the weight of the center of every face in the digital surface mesh with the weight equal to the face area. Alternatively, the computer-implemented method can set the weight of the set of points to other values. Next, the computer-implemented method can find a center of mass of the set of points. Next, the computer-implemented-system can determine a covariance matrix 3×3 relative to the center of mass and find 3 pairs of eigenvector and eigenvalue of the matrix.

The computer-implemented method can determine the least squares plane as the plane passing through center of mass with the normal equal to the eigenvector corresponding to the smallest eigenvalue. The computer-implemented method can determine a least squares line as the line passing through the center of mass with the direction vector equal to the eigenvector corresponding to the largest eigenvalue.

Figure 22:
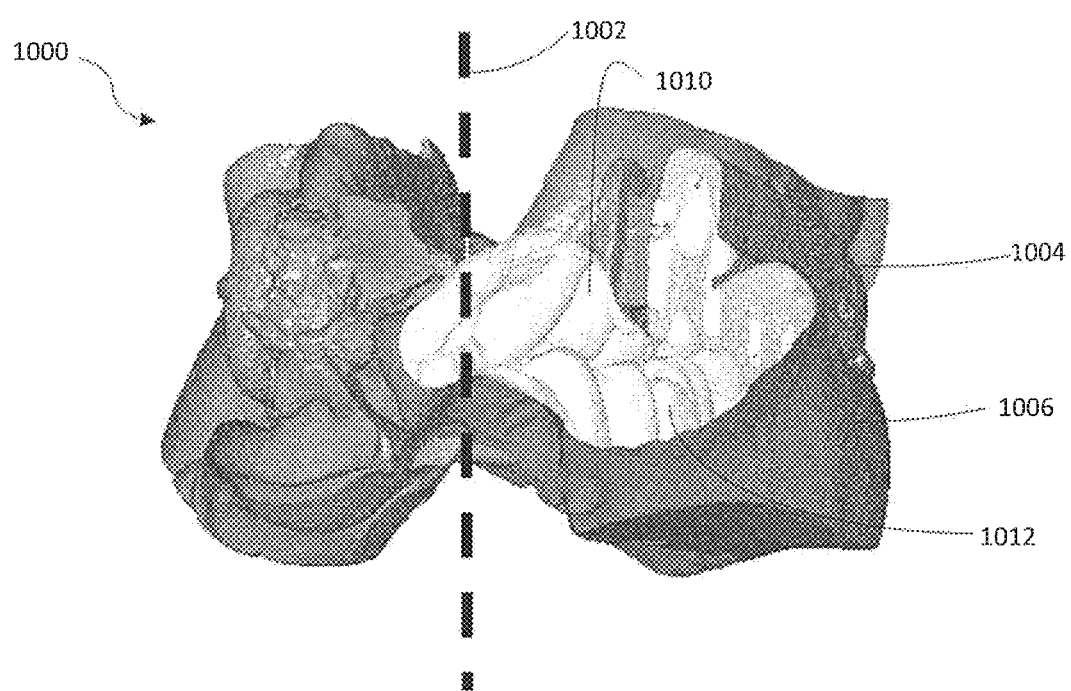
FIG. 22 is an example of a 3-dimensional (3D) digital dental model.

In some embodiments, the computer-implemented method can generate one or more rays along one or more directions as described in the Direction Determination section of the present disclosure in the digital model to determine digital dental impression material thickness in the digital model and determine the occlusion axis based on the thickness. FIG. 22 illustrates a digital dental impression 1000 of a triple tray impression with first and second sides 1004 and 1006 and an occlusion axis 1002 to be found from the digital dental impression 1000 of the sides 1004 and 1006. As illustrated in FIG. 22, the occlusion axis 1002 is in a direction from a first side 1004 of the digital dental impression 1000 such as first jaw for example to a second side 1006 of the digital dental impression 1000 such as a second jaw for example, and is orthogonal to first and second biting surfaces 1010 and 1012.

Although digital dental impression 1000 is shown in FIG. 22 at a particular orientation for illustrative purposes, the digital dental impression 1000 may be arbitrarily oriented in any direction and at any angle in three dimensions. Additionally, first and second sides 1004 and 1006 may correspond to either the upper or lower jaw; the orientation of digital dental impression 1000 as illustrated in FIG. 22 is not intended to restrict first side 1004 to an upper or lower jaw, nor restrict second side 1006 to an upper or lower jaw. Likewise, the orientation of digital dental impression 1000 as illustrated in FIG. 22 is not intended to imply or restrict first biting surface 1010 to an upper or lower biting surface, nor restrict biting surface 1012 to an upper or lower biting surface.

The computer-implemented method can automatically detect occlusion axis 1002 of the arbitrarily oriented digital dental impression 1000 based on features in the digital dental impression 1000. For example, in some embodiments, the computer-implemented method can automatically determine the occlusion axis of a digital triple tray impression by determining a plurality of candidate directions to determine a first and last intersection point between the digital dental impression and one or more rays along a chosen direction. A metric between the first and last intersection point is calculated for a plurality of directions and a criteria for the occlusion axis is determined and can be user-selectable. The criteria can be applied to the metric to one or more candidate directions. The metric can be, for example, a thickness or length of digital dental impression material in some embodiments.

Figure 23A:
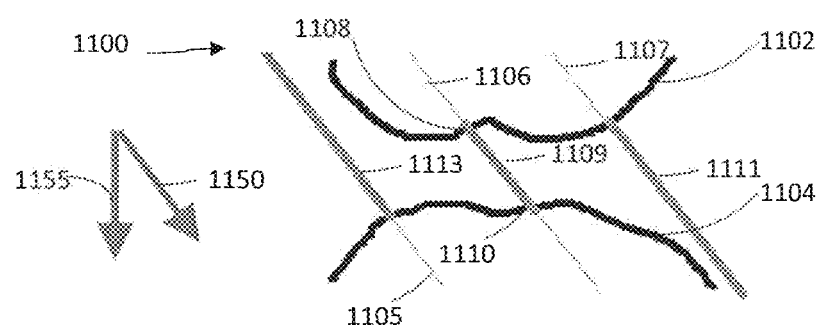
FIG. 23(a) and FIG. 23(b) are cross sectional illustrations of portions of a patient dentition with one or more rays generated along chosen directions.
Figure 23B:
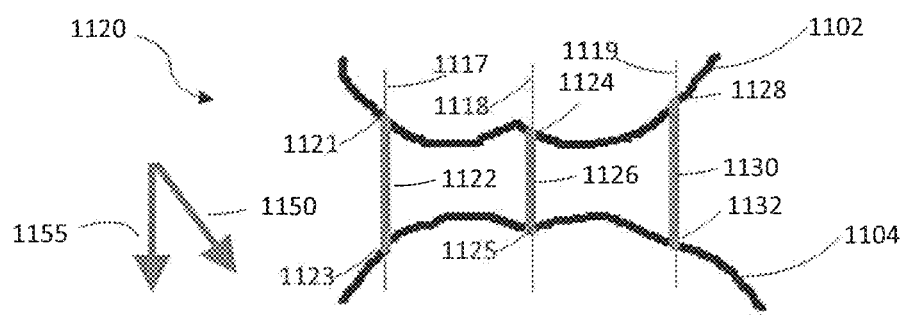

FIG. 23(a) and FIG. 23(b) show examples of cross section representations 1100 and 1120, respectively, of the digital dental impression 1000 with first and second digital biting surface regions 1102 and 1104. As illustrated in the example shown in FIG. 23(a), the computer-implemented method can generate one or more rays along multiple candidate directions 1150 and 1155 as described in the Direction Determination section and other portions of the present disclosure, and determine first and last intersection points 1108 and 1110 between the digital dental impression cross section 1100 and a ray 1106 along a chosen direction 1150. Although candidate directions 1150 and 1155 are shown for illustrative purposes in the figure, many other candidate directions are possible. In the example of FIG. 23(a), ray 1106 intersects with digital dental impression cross section 1100 at the first biting surface region 1102 at intersection point 1108 and intersects the second biting surface region 1104 at intersection point 1110, thereby establishing a thickness of digital dental impression material 1109. The thickness of digital dental impression material 1109 can be the distance or length between first intersection point 1108 and last intersection point 1110, or thickness of digital dental impression material along a direction. Also shown are rays 1105 and 1107, also along a chosen direction 1150. Although ray 1105 is shown to only intersect with the second biting surface region 1104, it also intersects with the first biting surface region 1102 (not shown) and has a thickness of digital dental impression material along the direction. Similarly, although ray 1107 is shown to intersect with only the first biting surface region 1102, it also intersects with second biting portion 1104 (not shown) and has a thickness of digital dental impression material along the direction 1111.

FIG. 23(b) illustrates an example of the computer-implemented method with generated multiple candidate directions 1150 and 1155 and rays 1117, 1118 and 1119 along a chosen direction 1155 rather than direction 1150. As shown in FIG. 23(b), ray 1117 along the chosen direction 1155 has first and last intersection points 1121 and 1123, respectively, thereby establishing a thickness of digital dental impression material 1122. Ray 1118 along the chosen direction 1155 has first and last intersection points 1124 and 1125, respectively, thereby establishing a thickness of digital dental impression material 1126. Ray 1119 has first and last intersection points 1128 and 1132, respectively, thereby establishing a thickness of digital dental impression material 1130. The thicknesses of digital dental impression material 1122, 1126, and 1130 can be the distance or length between their respective first and last intersection points.

In some embodiments, the computer-implemented method determines one or more metrics between the first and last intersection point for a plurality of directions and selects a criteria for the occlusion axis. In some embodiments, the metric can be the thickness of digital dental impression material along directions in a chosen direction. As discussed previously, the thickness of digital dental impression material can be the distance or length between corresponding first and last intersection points of the ray with the digital dental impression 1000. The metric can be, for example, the thicknesses of digital dental impression material 1113, 1109, and 1111 for corresponding rays 1105, 1106, and 1107, respectively, as shown in FIG. 23(*a*). The metric can be, for example the thicknesses of digital dental impression material 1122, 1126, and 1130 of corresponding rays 1117, 1118, and 1119 in the example illustrated in FIG. 23(*b*). In some embodiments, the metric can be, for example, the average of thicknesses of digital dental impression material in a chosen direction. For example, the metric can be the average of thicknesses of digital dental impression material 1113, 1109, and 1111 for corresponding rays 1105, 1106, and 1107, respectively, as shown in FIG. 23(*a*) and the metric can be, for example the average of thicknesses of digital dental impression material 1122, 1126, and 1130 of corresponding rays 1117, 1118, and 1119 in the example illustrated in FIG. 23(*b*).

Some embodiments include the computer-implemented method selecting a criteria indicating the occlusion axis and applying the criteria to the metric to one or more candidate directions. For example, selecting the criteria can include selecting a minimum of the average thicknesses of digital dental impression material along a direction among the candidate directions 1150 and 1155. For example, a first average of the thicknesses of digital dental impression material 1109, 1111, 1113 for rays along chosen direction 1150 from FIG. 23(*a*) and a second average of the thicknesses of digital dental impression material 1122, 1126, 1130 for rays along chosen direction 1155 from FIG. 23(*b*) can be calculated by the computer-implemented method. Applying the selecting criteria, a minimum of the first and second averages is selected by the computer-implemented method, which in this example is the second average. Since the second average corresponds to chosen direction 1155, criteria indicating the occlusion axis in this would be along the chosen direction 1155 in this example. The occlusion direction and/or occlusion axis can, in some embodiments, also be referred to as the direction facing the opposing jaw.

In some embodiments, the computer-implemented method can utilize graphics hardware to generate two renderings for each of the plurality of candidate directions. For example, the computer-implemented method can generate a first rendering in a chosen direction and a second rendering generated in a direction opposite the chosen direction. A thickness of digital dental impression material at each pixel can be obtained by the computer-implemented method as a difference between z-depth values of the first and second rendering. In some embodiments, chosen direction having the least thickness of digital dental impression material or z-depth difference is the occlusion direction/axes or direction facing the opposing jaw. In some embodiments, the z-depth difference can be determined by the computer-implemented method from every side of the digital dental impression. In some embodiments, the graphics card can be a video card.

Figure 24A:
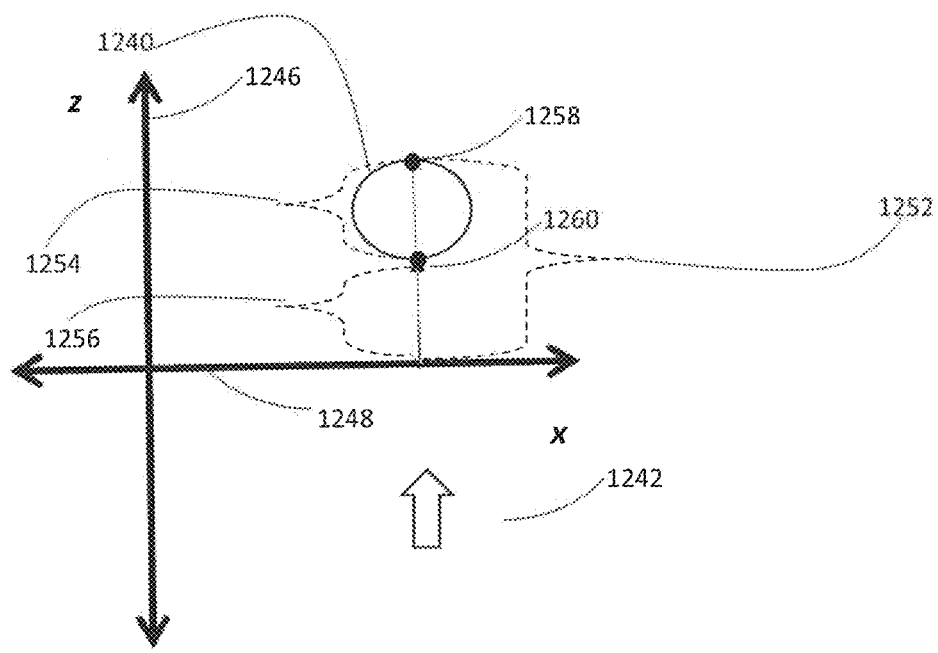
FIG. 24(a) is a graphical plot show z-depth of an image of a portion of patient dentition.
Figure 24B:
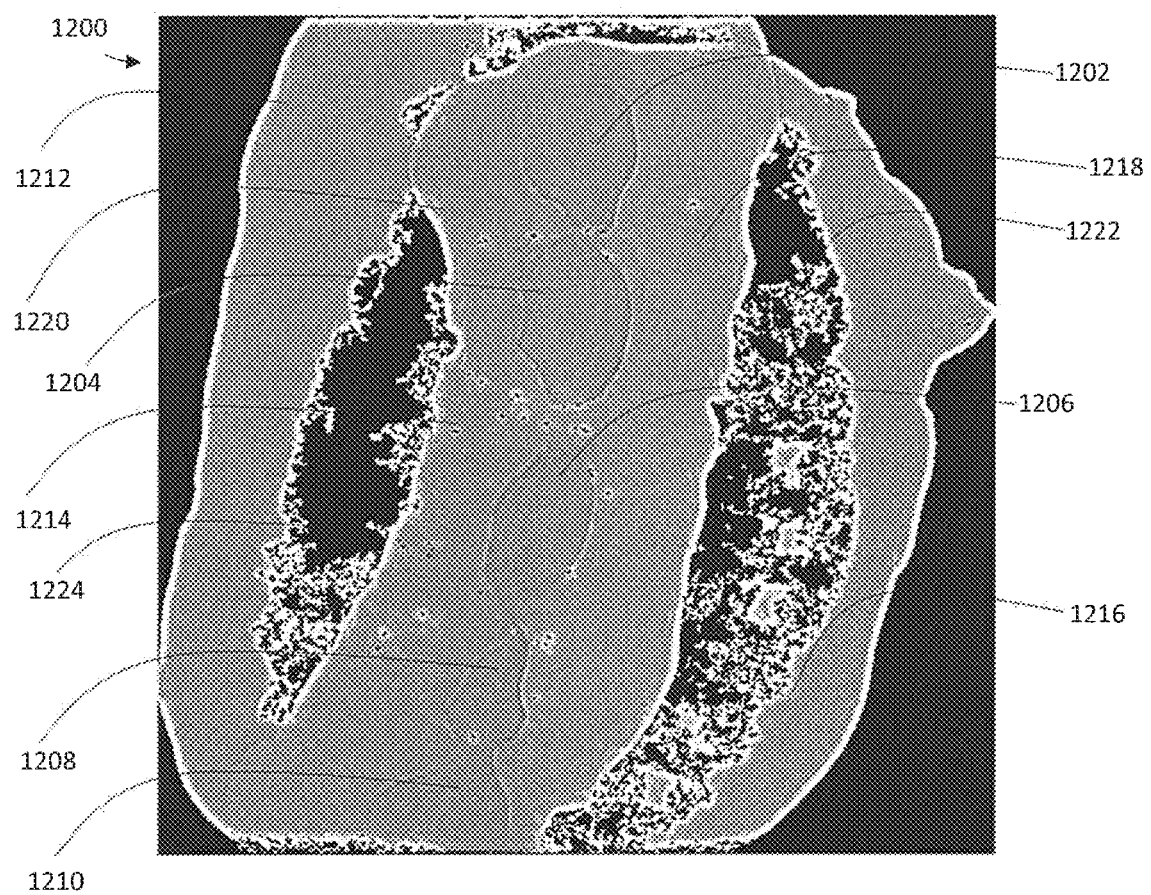
FIG. 24(b) is a 3-dimensional (3D) surface image representation of a portion of patient dentition.

FIG. 24(*a*) illustrates calculating thickness of digital dental impression material using pixels' z-depths plots in some embodiments. As shown in FIG. 24(*a*), z-axis 1246 plots a depth of 1256 for pixel 1260 of image 1240 rendered in chosen direction 1242, for example. Z-axis 1246 plots a depth of 1252 for pixel 1258 having the same x-y coordinates as pixel 1260 when image 1240 is rendered in a direction opposite the chosen direction 1242, for example. The difference between z-depth values 1252 and 1256 of the pixel 1260 rendered in the chosen direction 1242 and pixel 1258 rendered the direction opposite the chosen direction 1242 establishes the object thickness of digital dental impression material 1254. The chosen direction having the minimal thickness of digital dental impression material between pixels rendered in opposite directions is, for example, the occlusion direction, or the direction facing the other jaw.

FIG. 24(*b*) illustrates different thicknesses of digital dental impression material of regions based on first and second renderings. Regions 1202, 1204, 1206, 1208, and 1212 illustrate the most narrow parts. Regions 1214, 1216, 1218, and 1220 illustrate thicker parts, for example with a thickness of digital dental impression material more than 10 mm in some embodiments. Regions 1222 and 1224 illustrate areas where a direction does not find two intersections with impression having surface normal looking inside. One advantage of generating two renderings and using z-depth in some embodiments can be increased speed, for example.

Figure 25:
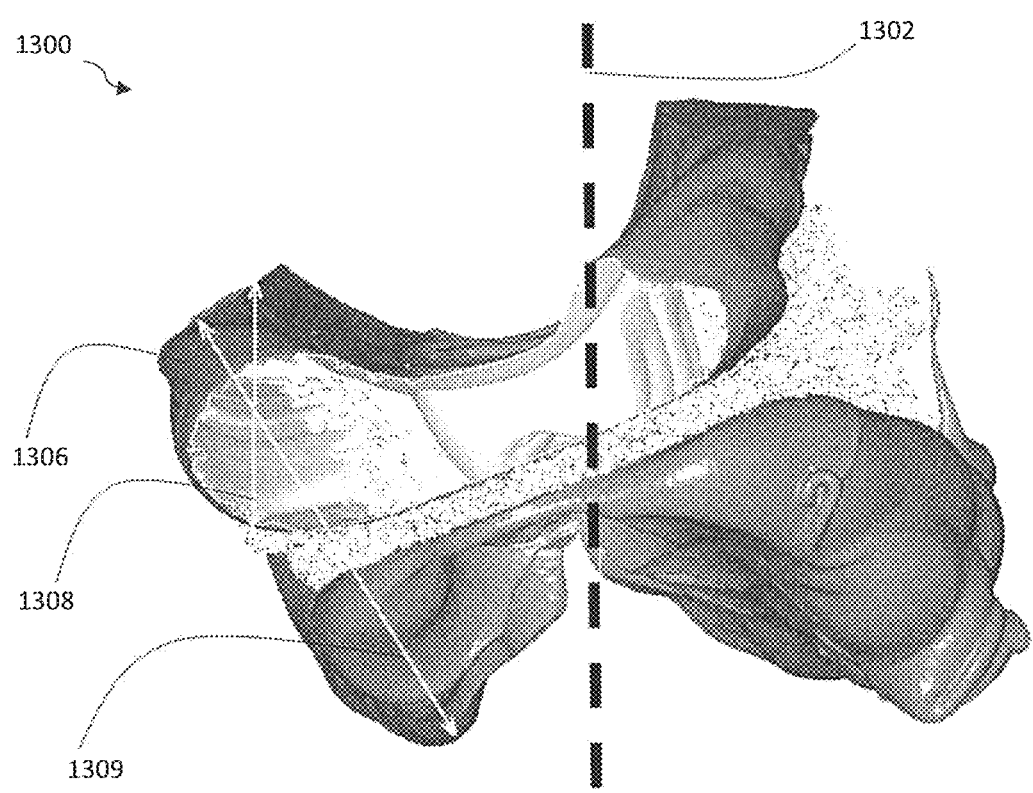
FIG. 25 is a cross-section of a 3-dimensional (3D) patient dentition.

In some embodiments, one or more walls of the digital dental impression can dominate in thickness of digital dental impression material and can affect averaging. For example, as illustrated in FIG. 25, the thickness of digital dental impression material for ray 1308 is less than the thickness of digital dental impression material for ray 1309, which has a bigger thickness of digital dental impression material due to the walls 1306 of the digital dental impression. This can lead to the incorrect occlusion direction/axis 1302.

Figure 26:
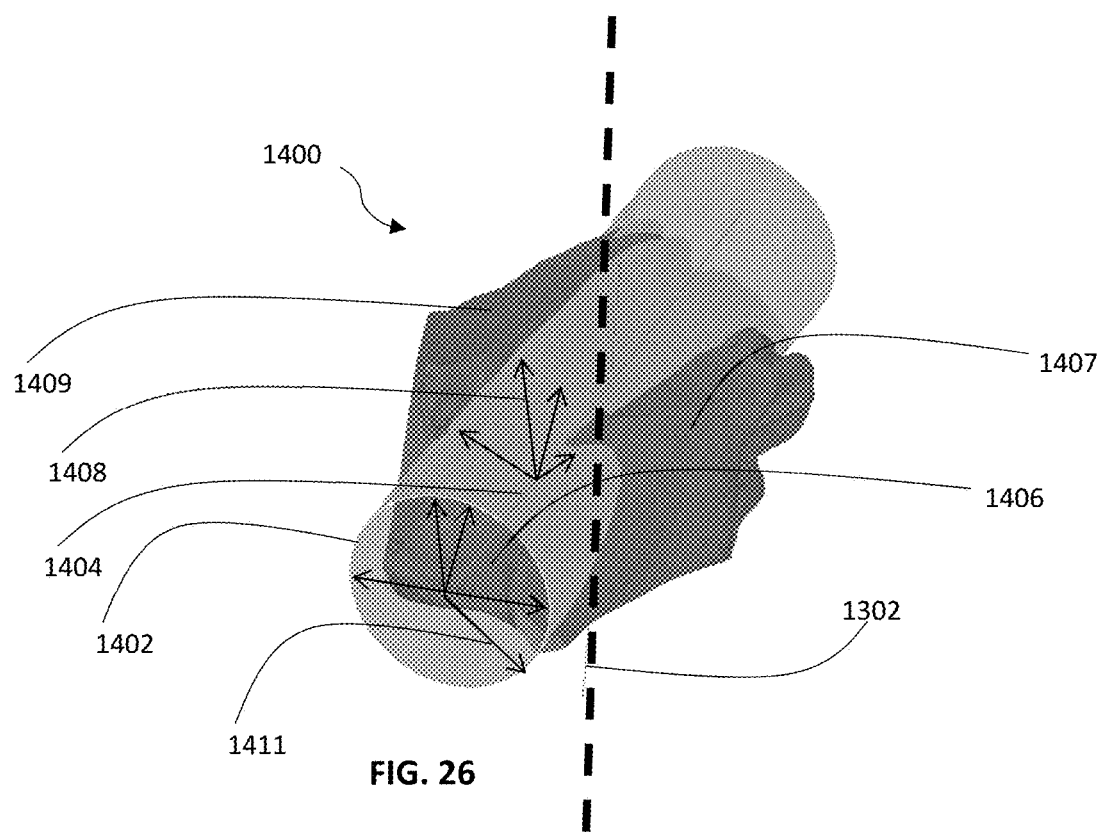
FIG. 26 is a perspective view of patient dentition showing a cylinder along a best least-squares line fit to the digital surface of the digital model.

Some embodiments of the computer-implemented method can determine an approximate location of teeth in anterior and quadrant triple tray impressions by determining a cylinder along a least-squares line fit to the digital surface of the digital model and computing a thickness of digital dental impression material along each of a plurality of directions only inside the cylinder. For example, FIG. 26 illustrates a dental impression 1400. In some embodiments, dental impression 1400 is an anterior triple tray impression. In some embodiments, dental impression 1400 is a quadrant triple tray impression. The computer-implemented method can apply a best line fit (least squares fit) 1404 as described in the present disclosure for the axis of the cylinder based on the entire digital surface of the digital model. In some embodiments, the method of least-squares can include, for example, calculating a least-squares line for all points or coordinates for the digital surface of the digital model as described herein or using any technique. The best line fit is also known as the least squares fit.

The best line fit 1404 can thus be established by the computer-implemented method for the points or coordinates that are part of the digital surface of the digital model. As illustrated in the figure, cylinder 1402 can be arranged with a radius to include teeth and exclude walls 1407 and 1409. Cylinder 1402 can be arranged to extend along a best line fit 1404 to a surface 1406 such that its radius is orthogonal to the best line fit 1404. In some embodiments, thickness of digital dental impression material is computed by the computer-implemented method only for triangles visible within the cylinder. In some embodiments, the radius is set to a parametric value. In some embodiments, the radius can be between 2 millimeters and 50 millimeters, for example. Other ranges may be possible. For illustrative purposes, only some rays 1408 and 1411 are shown in the figure. In some embodiments, for anterior and quadrant cases, it can be enough for the computer-implemented method to search the occlusion direction/axis 1302 only among directions orthogonal to the direction of the best line fit 1404 and within the cylinder. One advantage of using the cylinder 1402 to determine the occlusion direction is increased speed in some embodiments, for example. Since the dataset can be reduced to only data the within the cylinder, faster processing times are possible in some embodiments. Another advantage of using the cylinder to determine the occlusion axis 1302 can be greater accuracy in some embodiments, for example. Since the walls are eliminated by limiting the dataset to only considering data within the cylinder, error-causing wall thicknesses of digital dental impression material can be reduced or eliminated from the thickness of digital dental impression material determination in some embodiments.

Figure 27:
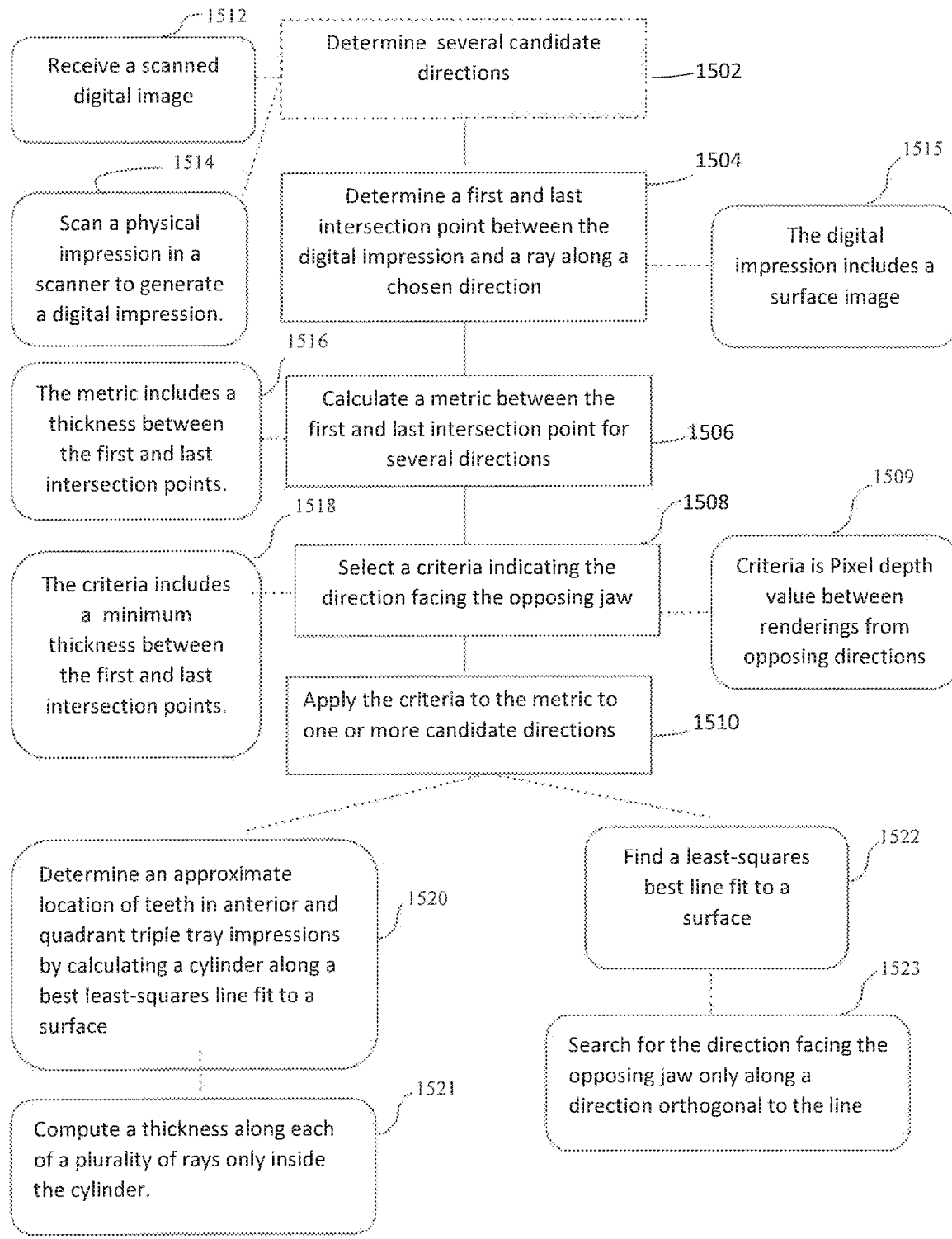
FIG. 27 and is a block diagram illustrating processes of automatic detection of a direction facing an opposite jaw.

FIG. 27 illustrates a computer-implemented method related to automatic detection of a an occlusion axis in a digital dental impression in some embodiments. In FIG. 27, a plurality of candidate directions is determined at 1502. A first and last intersection point between the digital dental impression and one or more rays along a chosen direction is determined at 1504. A metric between the first and last intersection point for a plurality of directions is calculated at 1506. A criteria indicating the occlusion axis is selected 1508. The criteria is applied to the metric to one or more candidate directions at 1510.

Some embodiments include receiving a scanned digital dental impression in step 1512. The image can be CT scanned or optically scanned. Some embodiments include scanning a physical impression in a scanner to generate a digital dental impression in step 1514. The physical impression can be CT scanned or optically scanned. The digital dental impression can be a surface image in step 1515.

In some embodiments, the metric can be a thickness of digital dental impression material between the first and last intersection points in step 1516. The criteria can be a minimum thickness of digital dental impression material between the first and last intersection points 1518. Some embodiments of the computer-implemented method include generating a first rendering in a first direction, generating a second rendering in a second direction opposite the first direction and calculating the metric at each pixel as a difference between depth values of the first and second renderings in step 1509. Some embodiments of the computer-implemented method can include determining an approximate location of teeth in anterior and quadrant triple tray impressions by calculating a cylinder along a best least-squares line fit to the digital surface of the digital model and computing a thickness of digital dental impression material along each of a plurality of directions only inside the cylinder in steps 1520 and 1521. Some embodiments of the computer-implemented method can include finding a least-squares best line fit to the digital surface of the digital model and searching for the occlusion axis only along a direction orthogonal to the line in steps 1522 and 1523.

Figure 28:
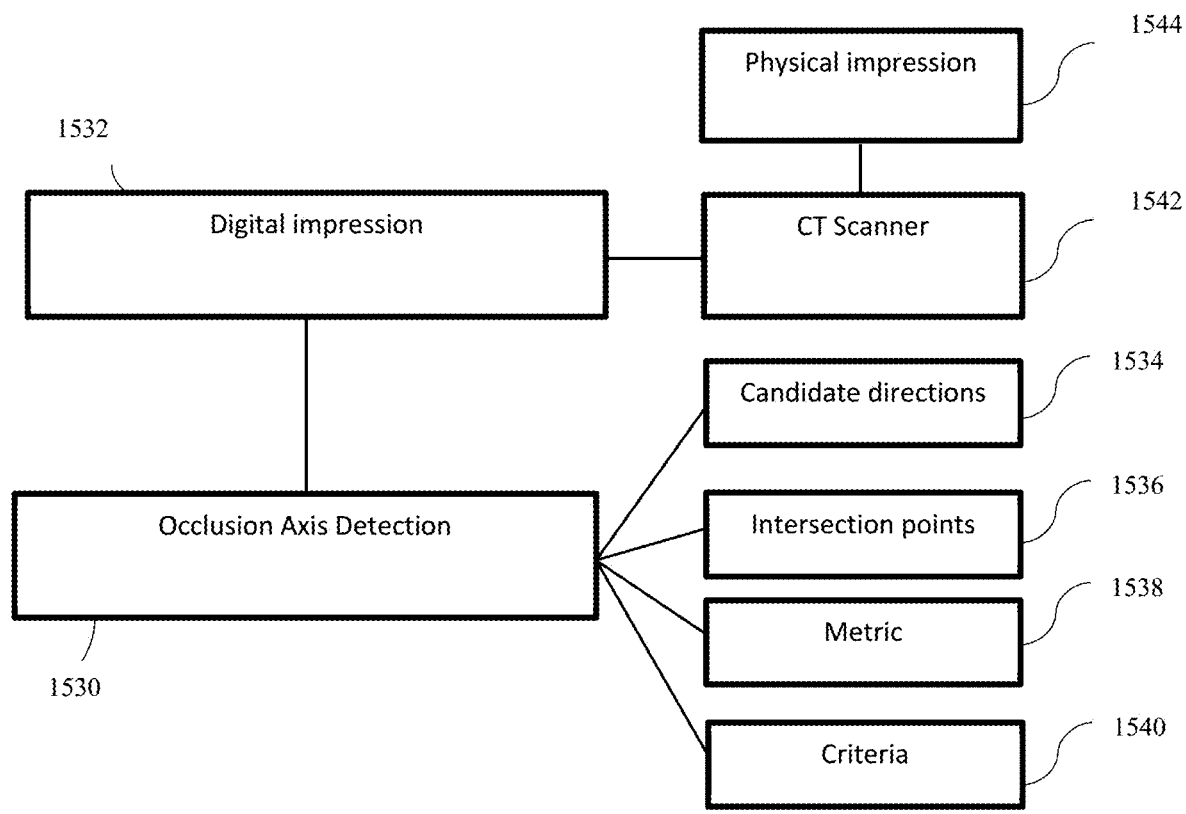
FIG. 28 is a diagram illustrating features of detecting occlusion axis.

FIG. 28 one or more optional automatic occlusion axis detection features 1530 in some embodiments. The features 1530 can be implemented in a digital dental impression processing system in some embodiments, for example. The features 1530 can include receiving a digital dental impression 1532. The digital dental impression 1532 can include a surface image. The features 1530 can include determining candidate directions 1534 in the digital dental impression 1532. The features 1530 can include determining a first and last intersection point 1536 between the digital dental impression 1532 and along a chosen direction, calculate a metric 1538 between the first and last intersection point for several directions, select a criteria 1540 indicating the occlusion axis, and apply the criteria 1540 to the metric 1538 to one or more candidate directions 1534. The metric can be a thickness of digital dental impression material or distance between the first and last intersection points 1536. The criteria 1540 can include a minimum value of the metric 1538. The criteria can be a pixel depth between two renderings from opposite directions. The renderings can be done on a video card. The video card can be internal. Applying the criteria 1540 to the metric 1538 in one or candidate directions 1534 can include finding a least-squares best line fit to the digital surface of the digital model and searching for the occlusion axis only along a direction orthogonal the line. In some embodiments, the features 1530 can include determining an approximate location of teeth in anterior and quadrant triple tray impressions by calculating a cylinder along a best least-squares line fit to the digital surface of the digital model and computing a thickness of digital dental impression material along each of several directions only inside the cylinder (See FIG. 26). In some embodiments, the features 1530 can include an optional a CT scanner 1542 arranged to generate a digital dental impression 1532 of a physical impression 1544 as illustrated in FIG. 28.

In some embodiments, a system of automatic detection of an occlusion axis in a digital dental impression is disclosed. The system includes a processor, a computer-readable storage medium including instructions executable by the processor to perform steps including: determining a plurality of candidate directions, determining a first and last intersection point between the digital dental impression and along a chosen direction, calculating a metric between the first and last intersection point for a plurality of directions, selecting a criteria indicating the occlusion axis and applying the criteria to the metric to one or more candidate directions.

In some embodiments, a non-transitory computer readable medium storing executable computer program instructions for automatic detection of a direction facing an opposing jaw in a digital dental impression is disclosed. The computer program instructions can include instructions for: determining a plurality of candidate directions, determining a first and last intersection point between the digital dental impression and along a chosen direction, calculating a metric between the first and last intersection point for a plurality of directions, selecting a criteria indicating the occlusion axis, and applying the criteria to the metric to one or more candidate directions.

Digital Splitting

In some embodiments, the computer-implemented method can digitally separate two jaws in a digital dental impression from each other or digitally separate a single jaw side from a non-anatomical side in a digital dental impression. The computer-implemented method of splitting a digital dental impression includes determining one or more first digital surface regions visible in one or more first directions on a first side of the digital dental impression along the occlusion axis and determining one or more second digital surface regions visible in one or more second directions on a second side of the digital dental impression along the occlusion axis. Surface region determination can be performed automatically by the computer-implemented method automatically in some embodiments.

Figure 29:
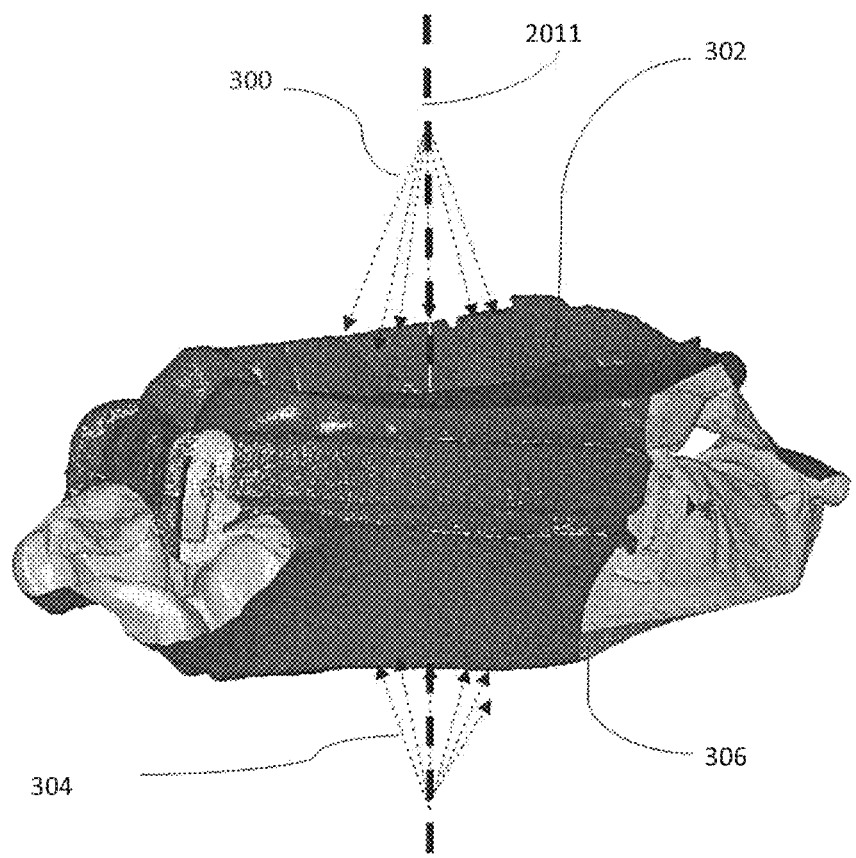
FIG. 29 a 3D digital model of a digital dental impression illustrating an example of surface region determination.

FIG. 29 illustrates an example of determining a first and second side of the digital dental impression in first and second directions along an occlusion axis. In some embodiments, the computer-implemented method can generate first set of directions 300 and second set of directions 304 as discussed in the Direction Determination section and throughout the present disclosure. The cone aperture of the directions generated can be any value. In one embodiment, the cone aperture can be up to 60 degrees, for example. In one embodiment, the cone aperture can be up to 120 degrees. The cone aperture can be increased or decreased as necessary so that a sufficient region of the digital surface is visible. The cone aperture can be the angle between any pair of the most distant directions in the cone aperture.

In some embodiments, the computer-implemented method determines first and second triangles and unattributed triangles by projecting a triangle in a direction onto a 2D plane of pixels as described in the Surface Visibility section and other sections of the present disclosure. As illustrated in FIG. 29, the computer-implemented method determines first digital surface regions visible in first directions 300 on a first side 302 of the digital dental impression around the occlusion axis 2011. The computer-implemented method determines second digital surface regions visible in second directions 304 on a second side 306 of the digital dental impression around the occlusion axis 2011 as illustrated in FIG. 29. In some embodiments, digital surface regions visible from both first directions 300 and second directions 304 are determined to be unattributed regions by the computer-implemented method. In some embodiments, digital surface regions not visible from either first directions 300 and second directions 304 are also determined to be unattributed regions by the computer-implemented method. In some embodiments, the one or more first and second digital surface regions can include triangles, for example.

Figure 30:
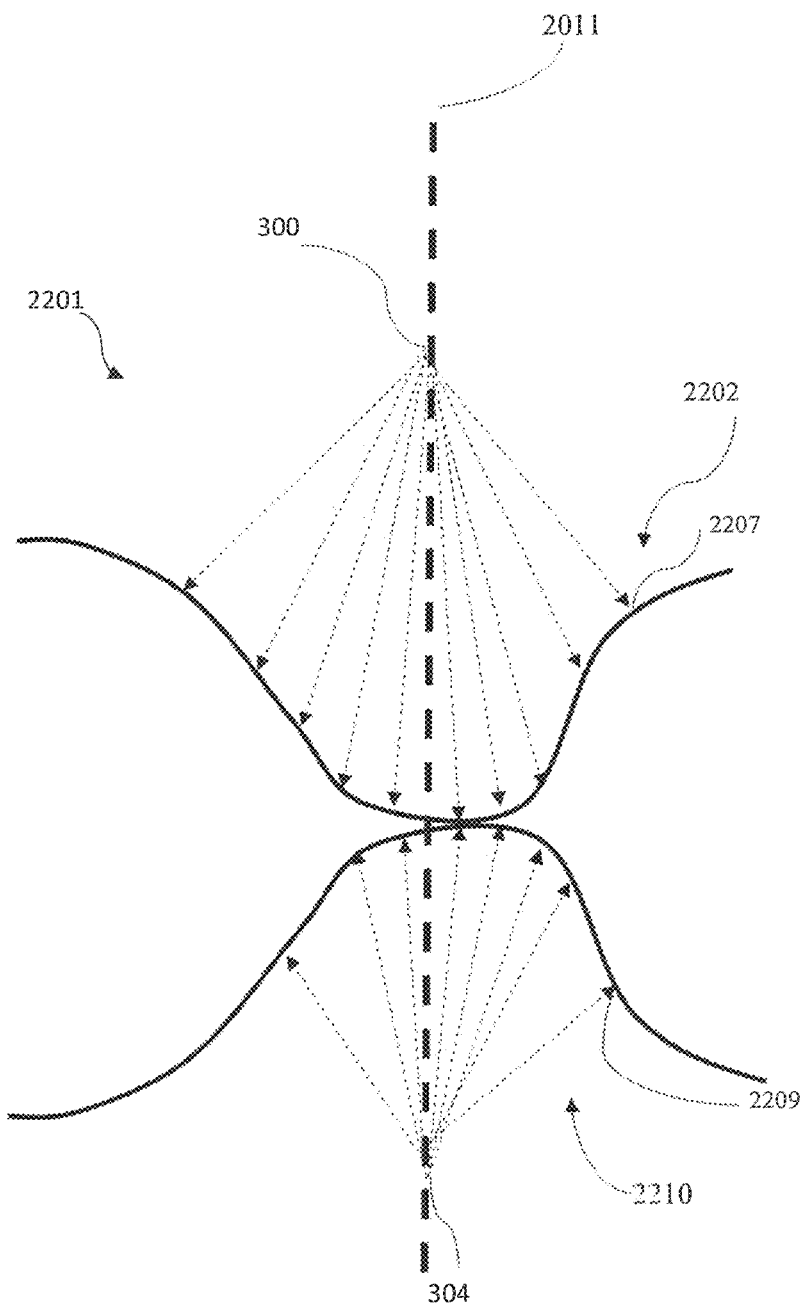
FIG. 30 is a 2D cross-section illustration showing surface region determination from two sides of a digital dental impression.

FIG. 30 illustrates a cross section of at least a portion of a first side 2202 of digital dental impression 2201 and at least a portion of a second side 2210 of the digital dental impression 2201 with occlusion axis 2011. In some embodiments, the computer-implemented method determines one or more first digital surface regions 2207 visible from one or more first directions 300 around the occlusion axis 2011 on the first side 2202 of digital dental impression 2201. In some embodiments, the one or more first digital surface regions 2207 can include one or more digital surface mesh triangles. In some embodiments, the computer-implemented method can determine one or more digital surface mesh triangles visible in at least one direction of the first set of directions 300 as belonging to the first digital surface region.

In some embodiments, the computer-implemented method determines one or more second digital surface regions 2209 visible in one or more second directions 304 around the occlusion axis 2011 on the second side 2210 of digital dental impression 2201. In some embodiments, one or more second digital surface regions 2209 can include one or more digital surface mesh triangles. In some embodiments, the computer-implemented method can determine one or more digital surface mesh triangles oriented toward at least one direction of the second set of directions 304.

In some embodiments, some digital surface regions may not be visible from one or more first directions 304 or one or more second directions 304. One or more unattributed regions 2212 can arise when the impression material between teeth of opposite jaws is too thin, for example. As shown in FIG. 18, this can cause "holes" or tunnels 901, 903, 905, 907 to appear in some areas.

Figure 31:
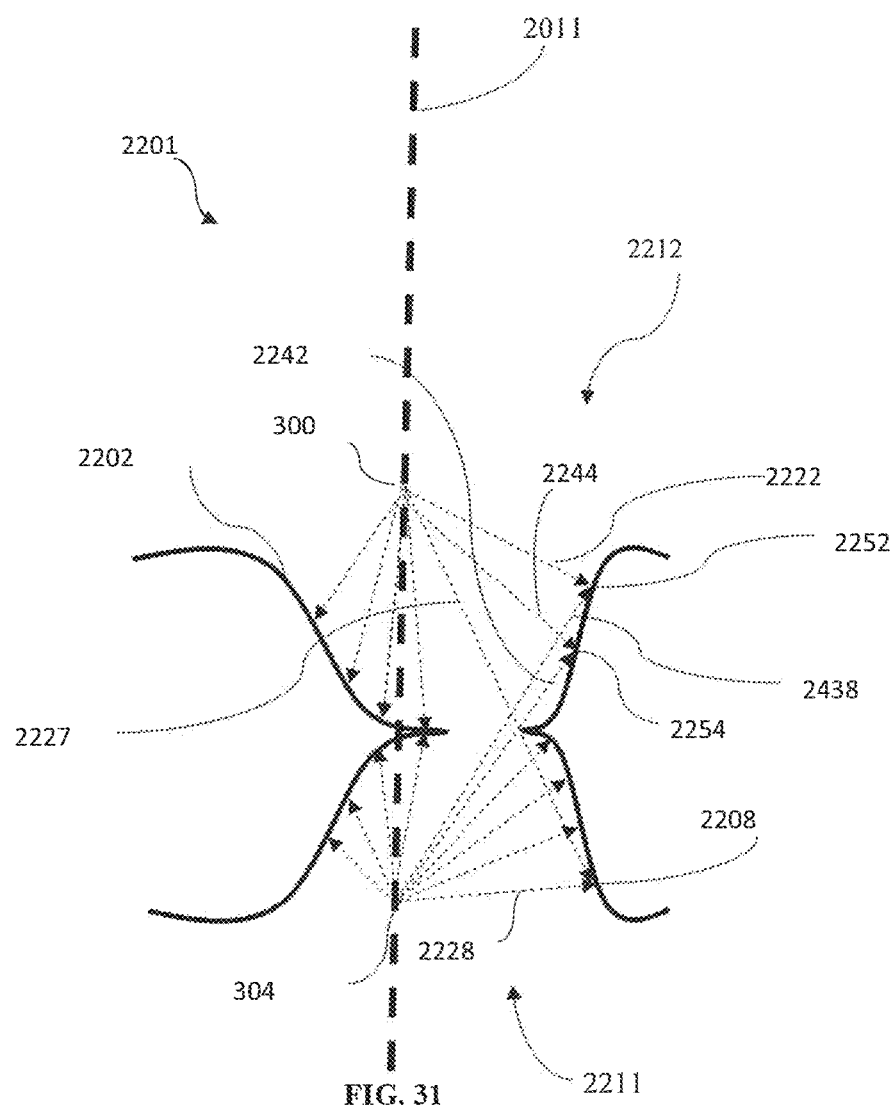
FIG. 31 is a 2D cross-section illustration showing surface region determination from two sides of a digital dental impression having holes or thin impression material regions.

The example in FIG. 31 shows one potential effect of tunnels 902. FIG. 31 illustrates an example of a cross section of a region of a first side 2212 and a region of a second side 2211 of the digital dental impression 2201 with occlusion axis 2011. Due to missing or thin impression material between first side 2212 and the second side 2211, digital surface region 2252 is visible from one or more directions 2222 from the first set of directions 300 and to one or more directions 2438 from the second set of directions 304. Similarly, digital surface region 2254 is visible from at least one or more directions 2244 from the first set of directions 300 and from at least one or more directions 2242 from the second set of directions 304, and digital surface region 2208 is visible from at least one or more directions 2227 from the first set of directions 300 and to one or more directions 2228 from the second set of directions 304.

Since the digital surface regions 2252, 2254 and 2208 are visible from at least a portion of both first and second sets of directions, the computer-implemented method determines the one or more digital surface regions in those digital surface areas to be unattributed regions. In some embodiments, digital surface regions may not be visible from any direction. The computer-implemented method determines these to be non-visible digital surface regions.

In some embodiments, the first and second digital surface regions and the one or more unattributed regions are triangles.

In some embodiments, the computer-implemented method can segment the entire digital dental impression surface into one or more digital segments. In some embodiments, the computer-implemented method can segment the digital dental impression surface in three dimensions (3D) using curvature based segmentation. This can include, for example, watershed segmentation. Segmentation can be performed by the computer-implemented method automatically in some embodiments.

In some embodiments, the digital dental impression surface can include one or more triangles that connect at edges and vertices to form the digital surface mesh. In some embodiments, the computer-implemented method determines the curvature of every triangle in the digital surface mesh. The computer-implemented method can determine the curvature of each particular triangle by either determining the average curvature of the particular triangle's vertices or the average curvature of the particular triangle's edges as described in the Curvature Determination section and other sections of the present disclosure.

Figure 32A:
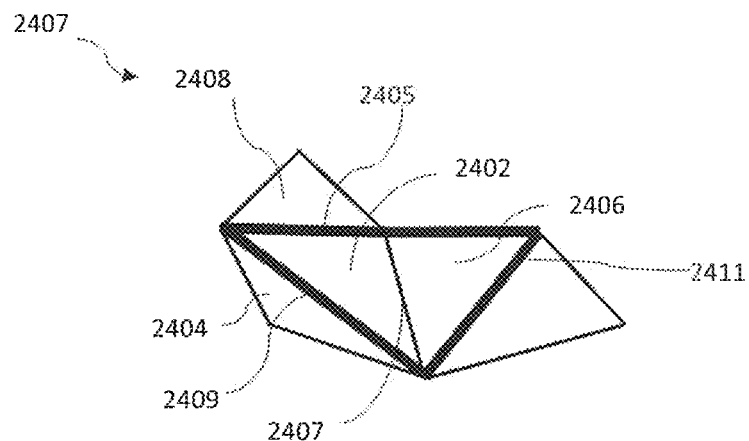
FIGS. 32(a), 32(b), and 32(c) are illustrations showing segmentation.
Figure 32B:
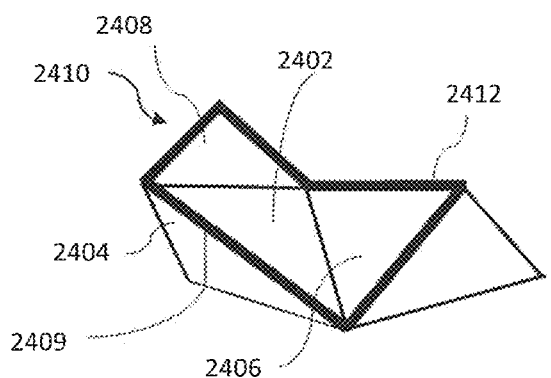
Figure 32C:
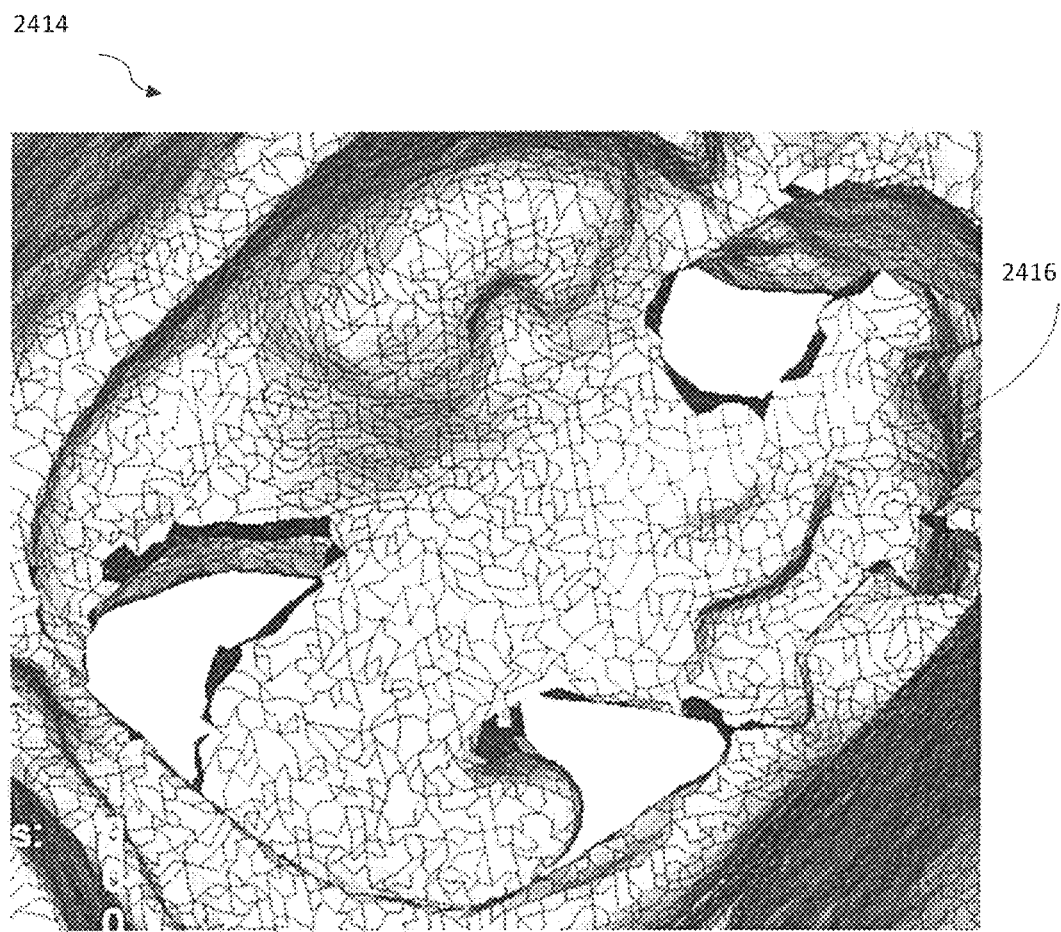

In one embodiment, the computer-implemented method can determine the curvature of a particular triangle by determining a curvature at each of the edge of the particular triangle and calculating an average of the edge curvatures as discussed in the Curvature Determination section of the present disclosure. FIG. 32(*a*) illustrates an example in some embodiments of determining an average of the edge curvatures in which a particular triangle 2402 includes a first edge 2405, a second edge 2407, and a third edge at 2409. The computer-implemented method can determine the curvature at the first edge 2405 based on the dihedral angle between the particular triangle 2402 and adjacent triangle 2408. The computer-implemented method can determine the curvature at the second edge 2407 based on the dihedral angle as described in this disclosure between the particular triangle 2402 and adjacent triangle 2406. The computer-implemented method can determine the curvature at the third edge 2409 based on the dihedral angle between the particular triangle 2402 and adjacent triangle 2404. The computer-implemented method can then determine the average of the curvatures of the first edge 2405, the second edge 2407, and the third edge at 2409 to determine the curvature of the particular triangle 2402. The computer-implemented method can in some embodiments store the curvature of the particular triangle 2402 in a look-up table, for example. The computer-implemented method can repeat this process with every triangle in the digital surface mesh and determine the curvature at each triangle in the digital surface mesh.

In some embodiments, the computer-implemented method can assign a user-selectable positive or negative sign to each triangle's curvature For example, if the curvature is set to the most convex edges, then any concave regions are assigned a negative sign, and any convex regions are assigned a positive sign. If the curvature is set to the most concave edges, then any convex regions are assigned a negative sign, and any concave regions are assigned positive signs. The concavity/convexity can be defined with respect to a digital surface normal. For surface normal directed outside of the digital surface, the computer-implemented method can assign a positive value to convex edges and a negative value to concave edges, for example. For normals directed inside of the digital surface, the computer-implemented method can assign positive values to convex edges and negative values to concave edges, for example. In some embodiments, segment boundaries correspond to maximum curvatures along the digital surface.

After determining each particular triangle's curvature, the computer-implemented method can segment triangles based on 3D curvature-based segmentation. In some embodiments, watershed segmentation is used. For example, in some embodiments, the computer-implemented method determines the curvature for each triangle. The curvature of each triangle can, in some embodiments, be stored in a lookup table. The computer implemented-method can start with a triangle with a minimum curvature as a particular triangle being evaluated. The computer-implemented method can look up the curvatures of triangles in the neighborhood of the particular triangle being evaluated from the look up table, for example. In some embodiments, the computer-implemented method can determine neighboring triangle curvatures from the look-up table. Any neighboring triangles with curvatures greater than the particular triangle being evaluated can be added to a segment to which the particular triangle being evaluated belongs. Any neighboring triangles with curvatures less than the curvature of the particular triangle are not added to the particular triangle's segment. The computer-implemented method then selects a neighborhood triangle as the next particular triangle to be evaluated and repeats the process for every triangle.

FIG. 32(*a*) illustrates an example in some embodiments of watershed segmentation of triangles. As discussed herein, the computer-implemented method determines the curvature of all of the triangles in the digital surface mesh. In one embodiment, the computer-implemented method stores the curvatures of the triangles in a lookup table. The computer-implemented method identifies the triangle with the minimum curvature, for example, particular triangle 2402. In some embodiments, the computer-implemented method can determine the triangle with the minimum curvature using the look up table. The computer-implemented method determines the curvatures of neighboring triangles 2404, 2408 and 2406. In some embodiments, the computer-implemented method can determine the curvatures of neighboring triangles from the lookup table. In the example, if the neighboring triangle 2406 has a greater curvature compared to the curvature of triangle 2402, then the neighboring triangle 2406 can be considered as part of the same watershed as the particular triangle 2402. The computer-implemented method combines the digital surface triangle 2402 with triangle 2406 into a single segment such as segment 2411 as illustrated in FIG. 32(*a*).

The computer-implemented method next can compare the curvature of neighboring triangle 2404 with the curvature of the particular triangle 2402, for example. If, for example, the curvature of neighboring triangle 2408 is greater than the minimum curvature (i.e. the curvature of 2402), then the triangle 2408 is merged with the segment 2411 containing triangle 2402. As illustrated in FIG. 32(*b*), segment 2412 is formed after merging triangle 2408.

If a neighborhood triangle has a lower curvature than the particular triangle 2402 in question, then the neighborhood triangle is not merged with the segment containing the particular triangle 2402 by the computer-implemented method. For example, if neighboring triangle 2404 has a lower curvature than the triangle 2402, then 2404 is not merged with the segment 2412 to which particular triangle 2402 belongs.

After processing a first particular triangle, the computer-implemented method changes to a new particular triangle which can be a neighboring triangle of the first particular triangle. The computer-implemented method can repeat determining segmentation with the new particular triangle being evaluated and segment the entire digital surface. FIG. 32(*c*) illustrates one example of a segmented digital surface mesh 2414 that includes segment 2416 for example.

Figure 33:
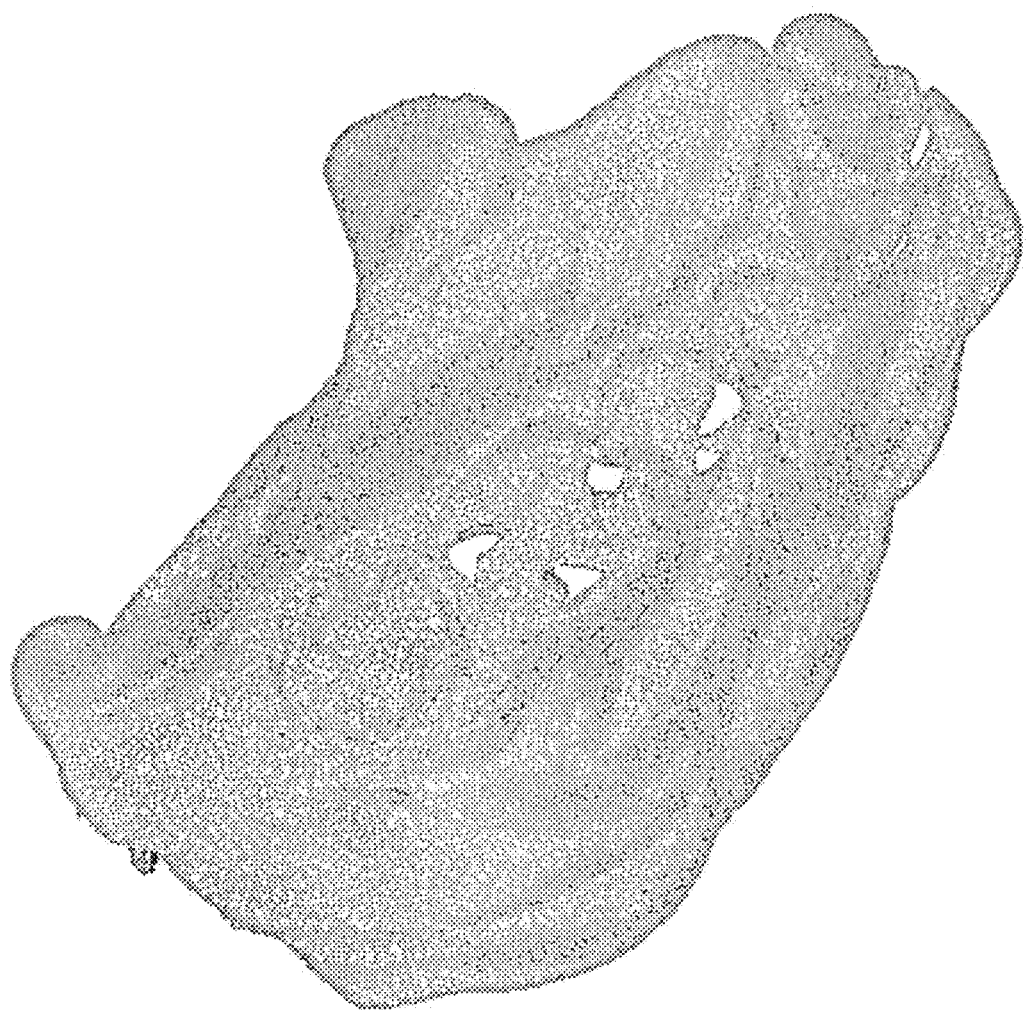
FIG. 33 is a 3D digital model illustrating segments.

After performing segmentation of triangles, the digital surface mesh can contain a large number of segments as illustrated in FIG. 33. In some embodiments, the number of segments can be reduced by the computer-implemented method by merging two or more segments together. In some embodiments, the computer-implemented method can merge small segments into larger ones based on geometric attributes such as their average curvature, average size, area, perimeter, perimeter to area ratio, and other geometric factors. In some embodiments, small segments can be merged based on the visibility of the triangles being merged. Merging can be performed automatically by the computer-implemented method in some embodiments.

In some embodiments, the computer-implemented method determines a merge-priority for every two neighboring segments. The computer-implemented method can determine merge-priority of two neighboring segments based on their attributes. If two segments can merge based on their attributes, then in some embodiments the computer-implemented method determines priority based on geometric factors. For example, the computer-implemented method can determine priority based on 1) average curvature inside each segment and on their common boundary (the segments with small difference between the curvature on the boundary and inside the segments merge earlier) and 2) the ratio of the length of the common boundary to the minimal perimeter of the two segments (the segments with larger ratio merge earlier).

In some embodiments, the computer-implemented method can store priorities in a priority-queue. The computer-implemented method can extract the highest priority from the queue, merge the corresponding two segments, and update the priorities between newly formed segments and their neighbors in the queue. The computer-implemented method can repeat this process until no two segments can be merged any more.

In some embodiments, the smaller segments can be merged until there are between 30-100 large segments, for example. One advantage of merging the segments as described in the present disclosure is more accuracy of the split digital model jaws, for example.

In some embodiments, the computer-implemented method can assign segments to a first side, a second side, or an unattributed side of the digital dental impression based on a majority of triangles in the segment. The computer-implemented method can determine side attribution automatically in some embodiments. No segment is attributed to both sides. If a segment includes unattributed triangles, then the unattributed triangles are assigned to the same side as the majority of the triangles by the computer-implemented method. For example, in FIG. 32(b), if a majority of the triangles 2402, 2406, and 2408 were determined by the computer-implemented method to belong to a first side, then the entire segment 2412 is determined by the computer-implemented method to belong to the first side after segmenting. This can resolve any triangles that may have been initially visible from both sides or not visible at all from both sides and therefore determined to be unattributed triangles. No single segment contains parts of both the upper and the lower sides. Every segment represents either a portion of the first side or a portion of the second side, and the boundary between first and second side on the digital surface can coincide with the boundary of some segments. For example, if triangle 2406 were visible from both the first and second sides, it would have been determined by the computer-implemented method to be unattributed to either side. The triangle 2406 is determined by the computer-implemented method to be part of the first side if both triangle 2402 and 2408 were determined to be part of the first side. This is because the majority of the triangles in the segment 2412 were determined to be part of the first side.

If a majority of triangles in a segment do not belong to either side, the entire segment can be determined to be unattributed by the computer-implemented method.

In some embodiments, the segment is attributed to the same side as at least one of its parts by the computer-implemented method.

In some embodiments, the digital surface segments can be identified by the computer-implemented method based on an initial orientation of the physical dental impression in the scanner. For example, as illustrated in FIG. 3, a user can specify the initial orientation of the physical dental impression with respect to a source to specify which side 147 of the physical impression 146 is facing the scanner source such as source of x-ray radiation 142. For single-sided impressions, the user can indicate that either the impression side or the non-impression side is facing the source prior to scanning the physical dental impression. For triple tray and/or full arch impressions, the user can indicate that an upper or lower jaw is initially facing the source prior to scanning the physical dental impression. After scanning the physical impression, generating the digital model, and splitting the digital model into at least one impression segment, the computer-implemented system can determine that the digital surface with the shortest distance to the source is the side initially oriented to face the source. For example, if the first digital surface has the shortest distance to the source, then the first digital surface is the side identified by the user prior to scanning. The second digital surface would then be either the other side (for triple tray and two full arch physical impressions) or the non-impression surface (for single side impressions). In some embodiments, the initial orientation of the physical dental impression in the scanner is known prior to scanning. The computer-implemented method can use the known initial orientation of the physical dental impression in the scanner to classify one or two jaws. For example, the computer-implemented method can classify a preparation jaw and an antagonist jaw or an upper jaw and lower jaw.

Single Jaw Impressions

Figure 34A:
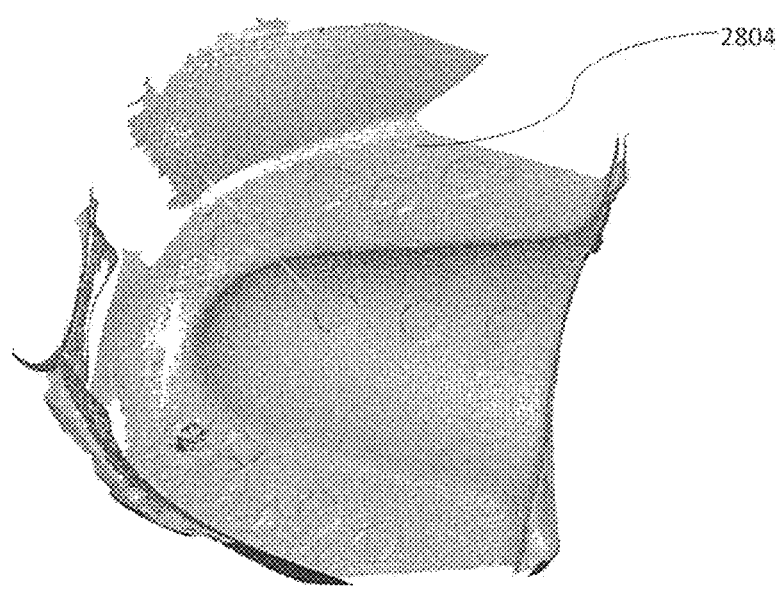
FIG. 34(a) is a 3D digital model of a non-impression side of a single jaw digital dental impression.
Figure 34B:
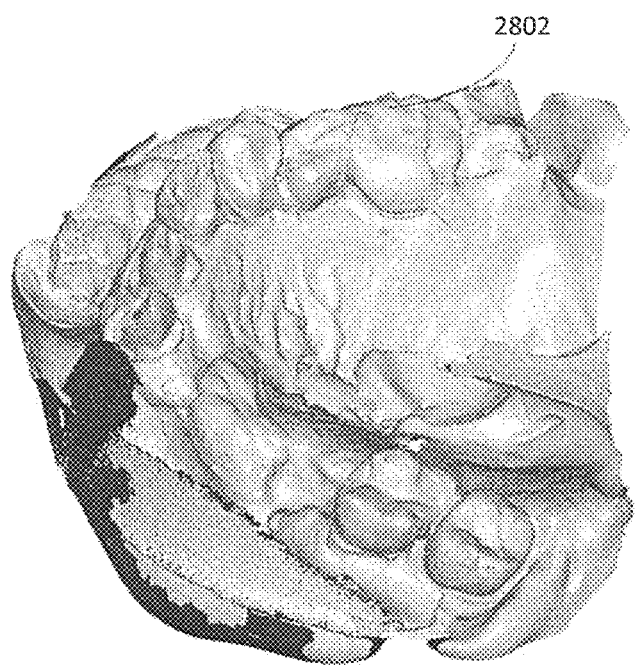
FIG. 34(b) is a 3D digital model of an impression side of a single jaw digital dental impression.

Some embodiments include digitally excluding non-anatomical data from a digital model of a single-jaw dental impression such as the one shown in FIG. 34(a), for example. Digitally excluding non-anatomical data from a digital model of a single-jaw dental impression can be performed automatically in some embodiments. Single-jaw impressions can contain an imprint of only one jaw, with the other side of the impression lacking any anatomical information. With single-jaw dental impressions, for example, a first side can be an impression side 2802 and a second side can be a non-impression side 2804 that bears no impression as shown in FIG. 34(a) and as illustrated in FIG. 34(b). In some embodiments, the non-impression side 2804 can be deleted from the digital model.

Figure 34C:
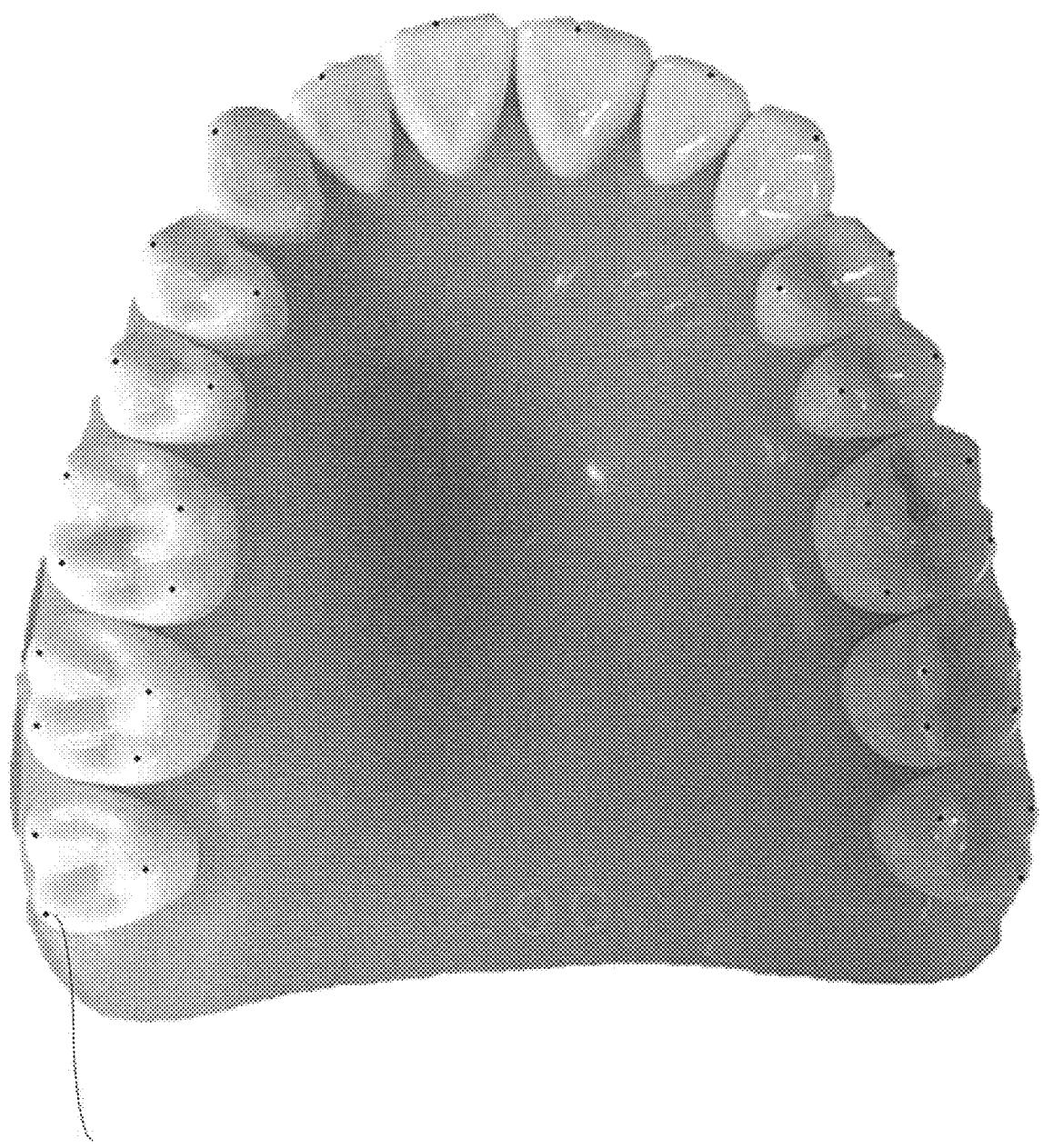
FIG. 34(c) is a 3D digital model of an impression side of a single jaw digital dental impression with detected cusps.

In some embodiments, determining the impression side 2802 can be based on the presence of dental features such as cusps, for example. Cusps are typically raised points on a tooth crown. The number of cusps on a tooth can depend on the type of tooth. For example, canine teeth may possess a single cusp, premolar teeth may have two cusps each, and molar teeth can have four or five cusps. Cusps appear most on the impression side 2802. For example, an impression side 2802 will typically have more cusps than a non-impression side 2804. For example, FIG. 34(c) illustrates the impression side 2802 with many cusps 2806 detected (denoted by white circles in the figure). FIG. 34(a) illustrates a non-impression side 2804 in which fewer or no cusps, for example, were detected. The computer-implemented method can detect one or more cusp regions on the first side and fewer cups regions on the second side, which is a non-impression side. Cusps can be detected as described in the Cusp Detection section.

Figure 34D:
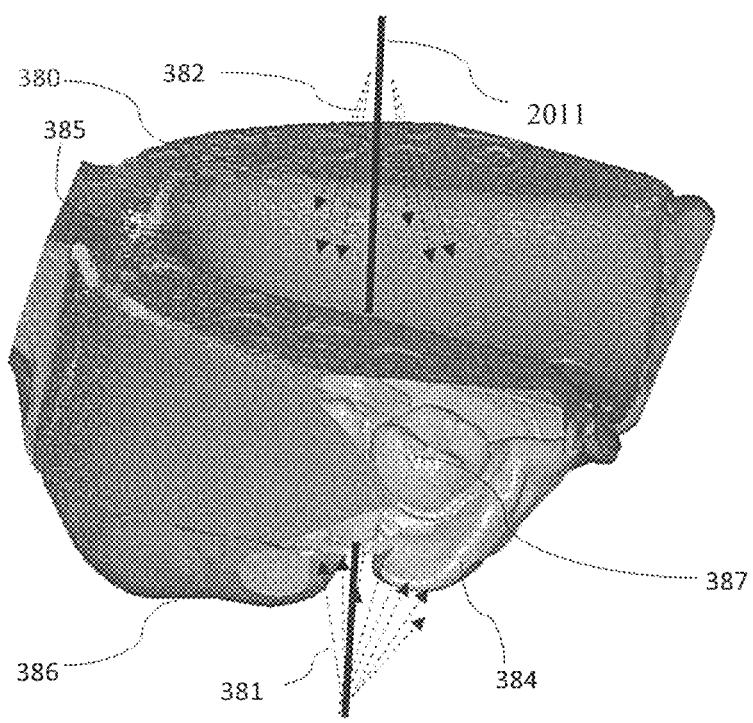
FIG. 34(d) is a 3D digital model example of a single jaw digital dental impression.

As illustrated in the example shown in FIG. 34(d), the computer-implemented method can determine one or more cusps 387 to determine an impression side 384 and non-impression side 380, for example.

The computer-implemented method can perform surface region determination, segmentation, merging, side attribution, handle non-anatomical features, implement other features as described the present disclosure for single jaw impressions. In some embodiments, the surface regions can be digital surface mesh triangles, for example.

For example, as discussed earlier in this disclosure and as illustrated in FIG. 34(d), the computer-implemented method can determine a first digital surface region 386 as visible from one or more first directions 381 around a first side 384 of the digital model of the triple tray impression along the occlusion axis 2011. The computer-implemented method can determine a second digital surface region 385 as visible from one or more second directions 382 around a second side 380 of the digital model of the triple tray impression along the occlusion axis 2011.

In some embodiments, the rays can be selected in the cone around occlusion direction with the aperture 60 degrees with the angles between individual rays not less than 10 degrees, for example. In one embodiment, the cone aperture to can be a user-selectable value up to and including 40 degrees, for example. However, the aperture can be increased or decreased as necessary to cover a sufficient digital surface region. For example, for cusps detection if the aperture is decreased too much, then not all cusps will be found on teeth inclined relative to the occlusion direction. If the aperture is increased too much, then false cusps will be found on the folds of the gum or other not-tooth regions of the digital surface.

The computer-implemented method can segment the digital surface mesh as described in the present disclosure. For example, the computer-implemented method can segment the digital surface mesh of the single-jaw impression using curvature based segmentation as described in the present disclosure. For single-jaw impressions, the segments can include impression segments and non-impression segments, for example. The segments can be merged as described in the present disclosure. The computer-implemented method can delete non-anatomical digital surface mesh features as described in the disclosure herein. For example, the computer-implemented method can delete the non-impression side 380 by retaining only those digital surface mesh segments visible from the impression side 384.

Cusp Detection

To detect cusps, the computer-implemented program first determines an occlusion axis 2904. The occlusion axis can be provided in the digital model, or can be determined as described in the present disclosure for example in the Occlusion Axis section and throughout the present disclosure.

In some embodiments, the computer-implemented method determines all digital surface peaks in the digital surface model. In some embodiments, the peaks can be determined based on certain criteria, such as having the highest curvature, based on a height, or height to radius ratio.

Figure 35:
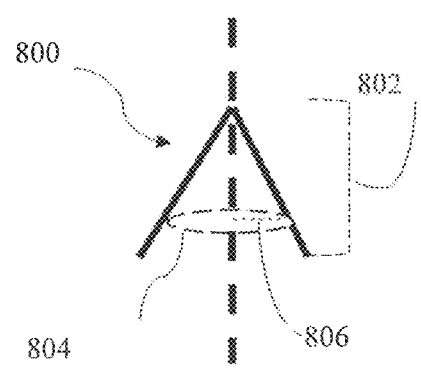
FIG. 35 is an illustration of an example of detecting cusps.

For example, as shown in the example of FIG. 35, the computer-implemented method can in some embodiments detect cusps by determining one or more peaks 800, which can be determined based on a height 802 and a neighborhood radius 806 of perimeter 804 on a given tooth. The perimeter 804 in some embodiments is an empirically set value. In some embodiments, the height 802 to radius 806 ratio is determined and if the height to radius ratio approximately equal to 1, then the peak 800 is identified as a cusp by the computer-implemented method. This can help distinguish a cusp from a ridge, for example.

Figure 36A:
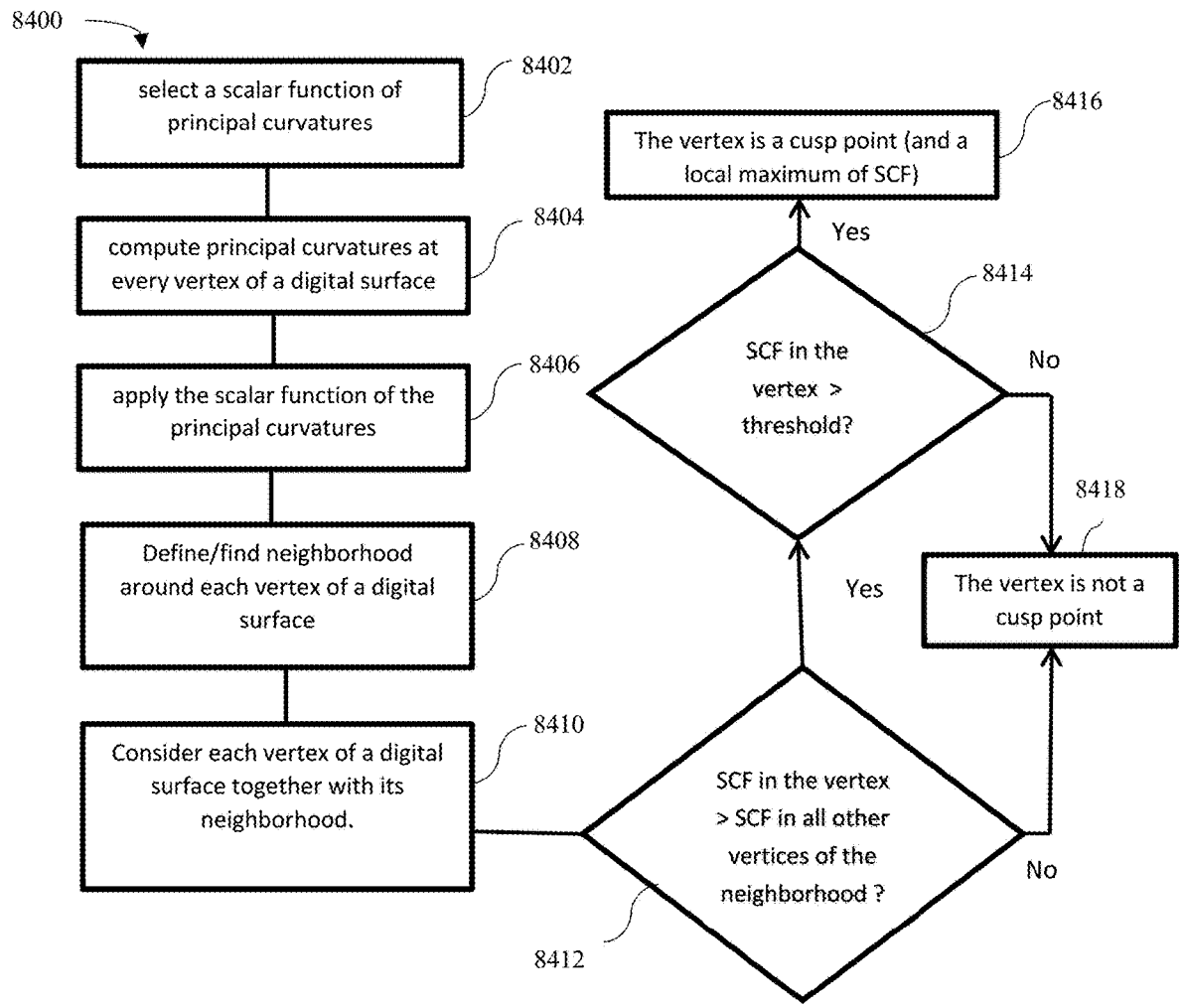
FIG. 36(a) is a flowchart example of detecting cusps via curvature.
Figure 36B:
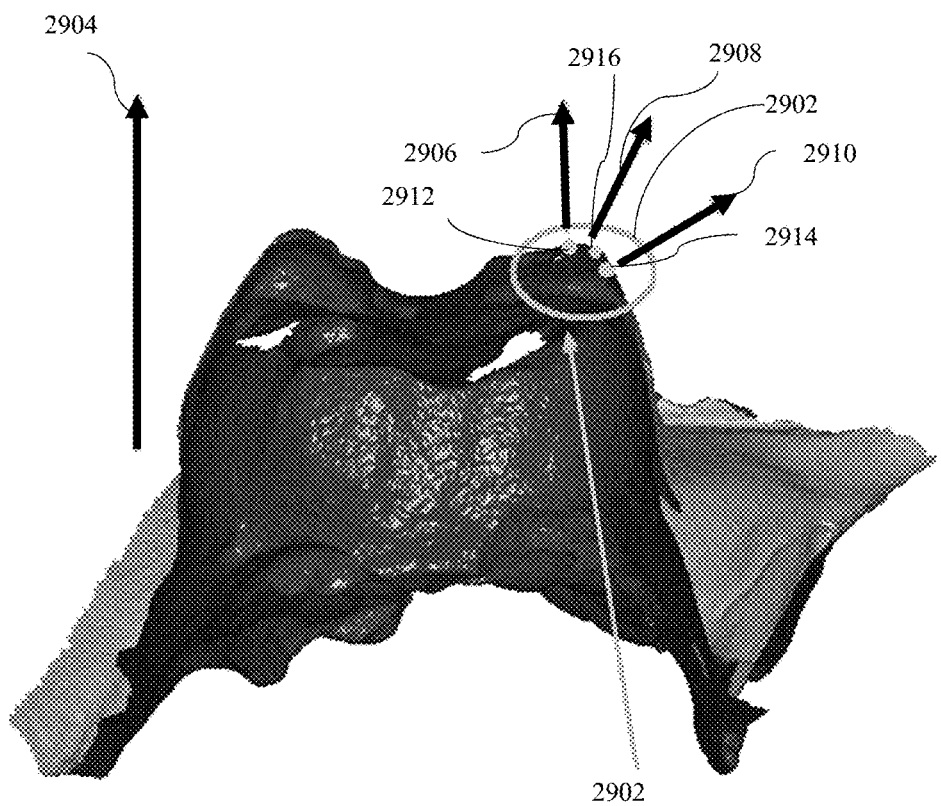
FIG. 36(b) is a 3D digital model of a single tooth illustrating an example of detecting cusps via local maxima.

In some embodiments, the computer-implemented method can detect cusps via curvature, as illustrated in FIG. 36(*a*) and as described in the Curvature Determination section and throughout the present disclosure, for example. The computer-implemented method can be configured to determine a user-selectable scalar function of principal curvatures at 8402. For example, the computer-implemented method can be configured to select between any scalar functions, including Gaussian curvature and Mean curvature, or any other scalar function. Next, the computer implemented-method can determine principal curvatures at every vertex of a digital surface mesh at 8404. The principle curvatures can be determined by any technique or method. In one embodiment, the principle curvatures are determined for every vertex by the computer-implemented method as described herein, for example in the Curvature Determination section of the present disclosure. The computer-implemented method can apply the selected scalar function to the principle curvatures to determine a selected curvature at 8406. The computer-implemented method can then define/find neighborhood around each vertex of a digital surface at 8408. The computer implemented-method can consider each vertex of a digital surface together with its neighborhood at 8410. The computer implemented method can compare the SCF in the vertex with the SCF in all other vertices of the neighborhood at 8412. If the SCF in the vertex is not greater than the SCF in all other vertices of the neighborhood, then the vertex is not a cusp point at 8418. If the SCF in the vertex is greater than the SCF in all other vertices of the neighborhood, then the computer-implemented method compares the SCF in the vertex to a user-selectable threshold at 8414. If the SCF in the vertex exceeds the threshold, then the computer-implemented method determines that the vertex is a cusp point (and a local maximum of SCF) at 8416. In some embodiments, the mean curvature and $k_1$ near dental cusps can be at least 100 $m^{-1}$ or higher, for example.

In some embodiments, the computer-implemented method can detect tooth cusps by determining local maxima by directions as illustrated in the example of FIG. 36(*b*). In some embodiments, the computer-implemented method can determine directions 2906, 2908, and 2910 as described, for example, in the Direction Determination section and throughout the present disclosure. In some embodiments, at least one direction is along the occlusion axis 2904. For example, direction 2906 can be along the occlusion direction 2904. For each selected direction, the computer-implemented method determines local surface maxima in the direction. For example, as illustrated in the figure, local maximum 2912 is determined along direction 2906, local maximum 2916 is determined along direction 2908, and local maximum 2914 is determined along direction 2910. In some embodiments, the computer-implemented method can determine the local surface maxima in a particular direction ("maxima" or "directional maxima") by determining all vertices in a neighborhood of a selected radius of a local maximum having a lower projection (i.e. height) along the direction than the local directional maxima. The computer-implemented method can form a cluster of points of local directional maxima. In some embodiments, each cluster can include one or more local directional maxima. In some embodiments, the one or more several directional maxima can be for one or more directions. In some embodiments, a close group can be designated as two or more directional maxima at or below a threshold distance that can be set by a user and used to process every digital image automatically. In some embodiments, the threshold distance can be in the range of 0 to 1 mm. A cluster can be designated as at least K directional maxima in the close group, where K is a user-selectable value specifying the number of directional maxima in the close group necessary to form a cluster. The computer-implemented method can define cusp-points as centers of clusters containing at least K directional maxima at 8466. Decreasing the value of K can lead to detection of more cusps on the digital surface, and increasing K can decrease the number of cusps found, for example. For example, setting the value of K to 5 requires at least 5 directional maxima within the close group distance to form a cluster. The computer-implemented method can determine the center of the cluster to be the cusp-point. If in the example only 4 or fewer directional maxima were located within the close group distance, then the computer-implemented method would not determine the 4 or fewer directional maxima to be a cluster.

Two Full Arch Impressions

Figure 37A:
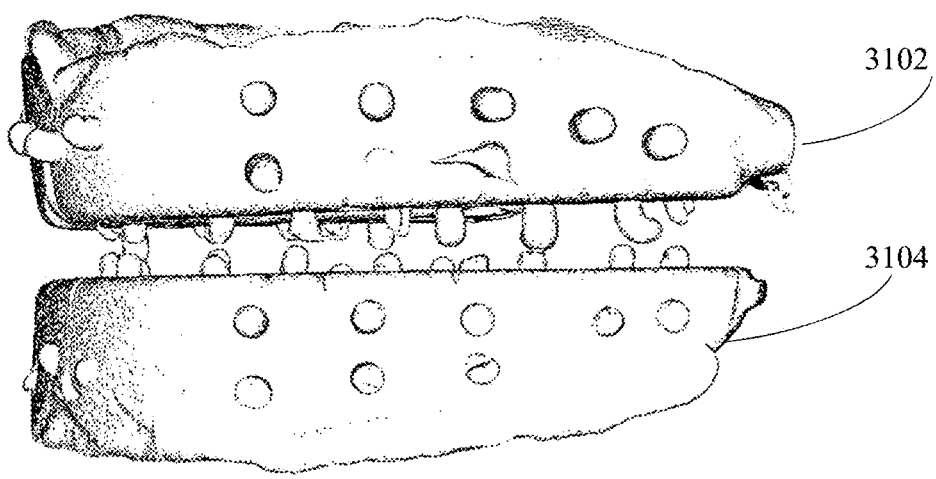
FIG. 37(a) is an illustration of two independent full arch impressions.
Figure 37B:
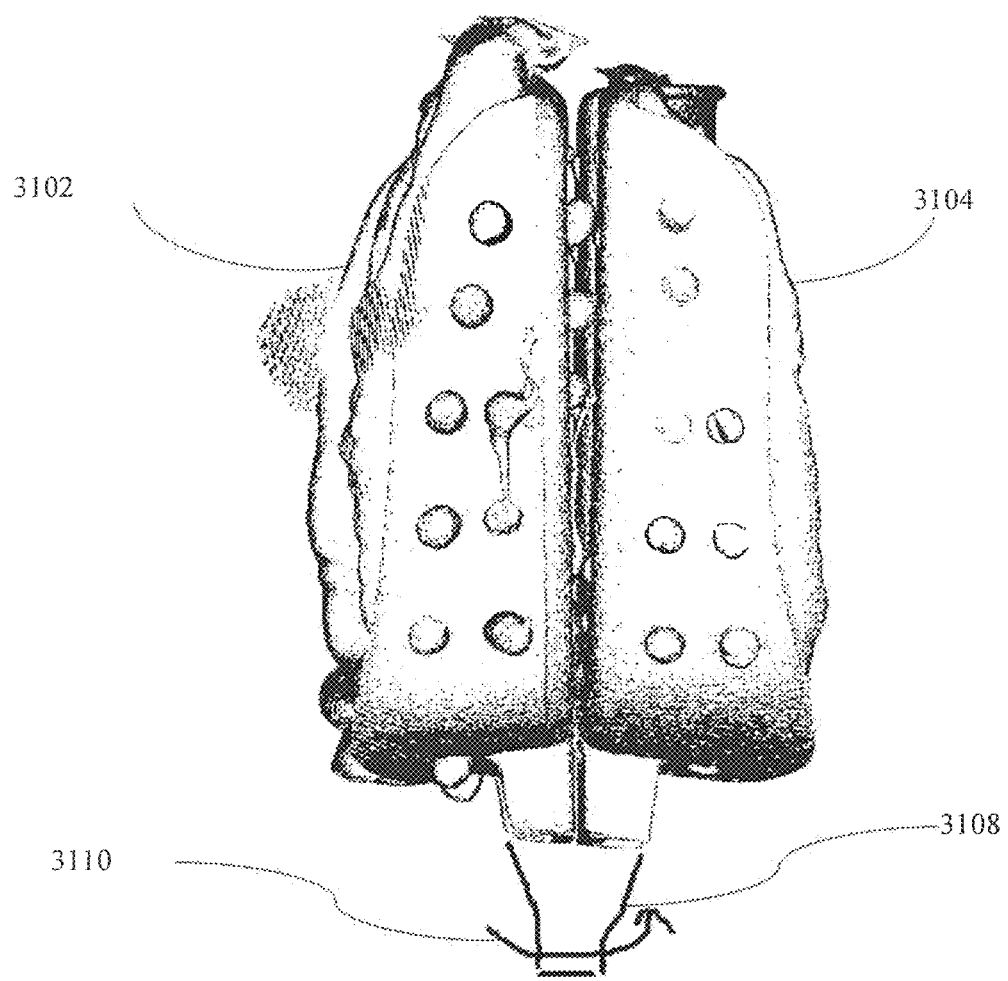
FIG. 37(b) is an illustration of scanning the two independent full arch impressions together.
Figure 38:
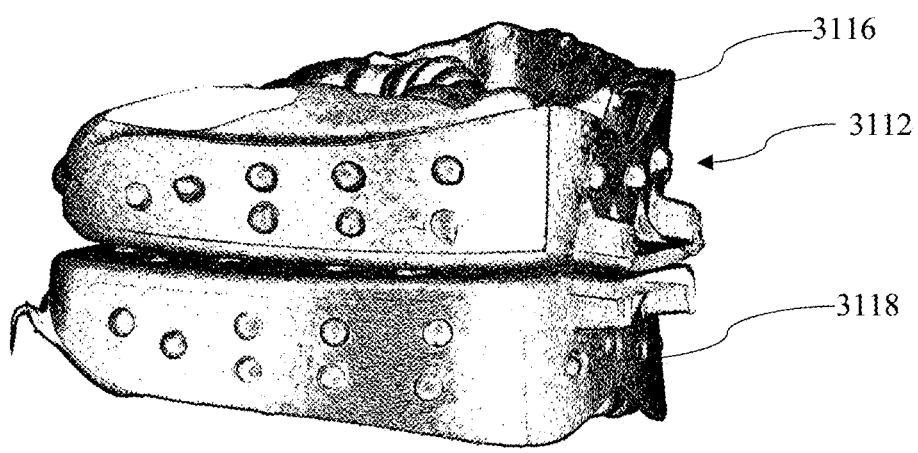
FIG. 38 is a 3D digital model of the two full arch impressions.

Some embodiments include a computer-implemented method of splitting a single image of two full arch physical impressions that were scanned together. For some patients, two separate (full arch) physical impressions are received instead of a triple tray impression, for example. As illustrated in the example shown in FIG. 37(a), independent first and second full arch physical dental impressions 3102 and 3104 are received. In some embodiments, the full arch physical impressions 3102 and 3104 can be mounted together onto a mounting element 3108. The mounting element 3108 can be configured to receive the independent physical first and second full arch impressions 3102 and 3104 and hold them in proximity during scanning as illustrated in FIG. 37(b). The mounting element 3108 and the two full arch physical impressions 3102 and 3104 can be placed in a CT scanner. In some embodiments, the mounting element 3108 and the two full arch physical impressions 3102 and 3104 together can be rotated 3110 in the CT scanner and scanned as shown, for example. The rotation can be clockwise or counter clockwise, and the first and second full arch physical impressions 3102 and 3104 can be mounted on the mounting element 3108 in any orientation. Scanning the independent first and second full arch physical impressions 3102 and 3104 together produces a single digital file of voxels. As illustrated in FIG. 38, a single digital surface 3112 of the two full arch physical impressions can be generated from the single digital image as discussed previously in the present disclosure. In some embodiments, the single digital file of voxels can be converted into the single digital surface 3112 using Marching Cubes or other techniques known in the art as discussed previously in the present disclosure. In some embodiments, the single digital file of voxels can be converted into a single digital surface 3112 by the computer-implemented method using the methods described in the PROCESSING CT SCAN OF DENTAL IMPRESSION application filed concurrently with this application as discussed previously in the present disclosure in the Digital Dental Impression section, for example. The single digital surface 3112 can be split into first 3116 and second 3118 digital full arch surfaces by the computer-implemented method. In some embodiments, splitting the single digital surface into first and second digital full arch surfaces can be performed by the computer-implemented method automatically.

Figure 39:
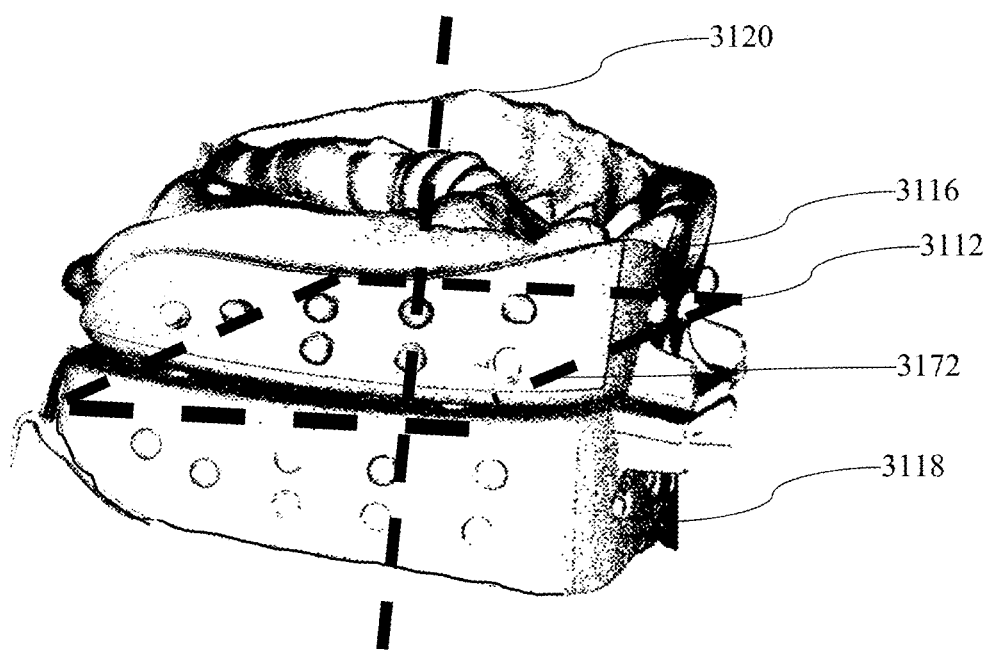
FIG. 39 illustrates an example of a 3D digital model with an occlusion axis and a least squares plane.

In some embodiments, splitting the single digital surface of the two full arches 3112 by the computer-implemented method includes determining an occlusion axis 3120 as illustrated in the example of FIG. 39. In some embodiments, the occlusion axis 3120 of the single digital surface 3112 can be automatically determined by the computer-implemented method by determining a least squares plane 3172 for the entire digital surface and determining the occlusion axis 3120 as a normal to the least squares plane 3172 as described in the present disclosure.

In some embodiments, splitting the single digital surface 3112 by the computer-implemented method includes surface region determination, segmentation, merging, and detecting cusps, as described previously in this disclosure.

Figure 40:
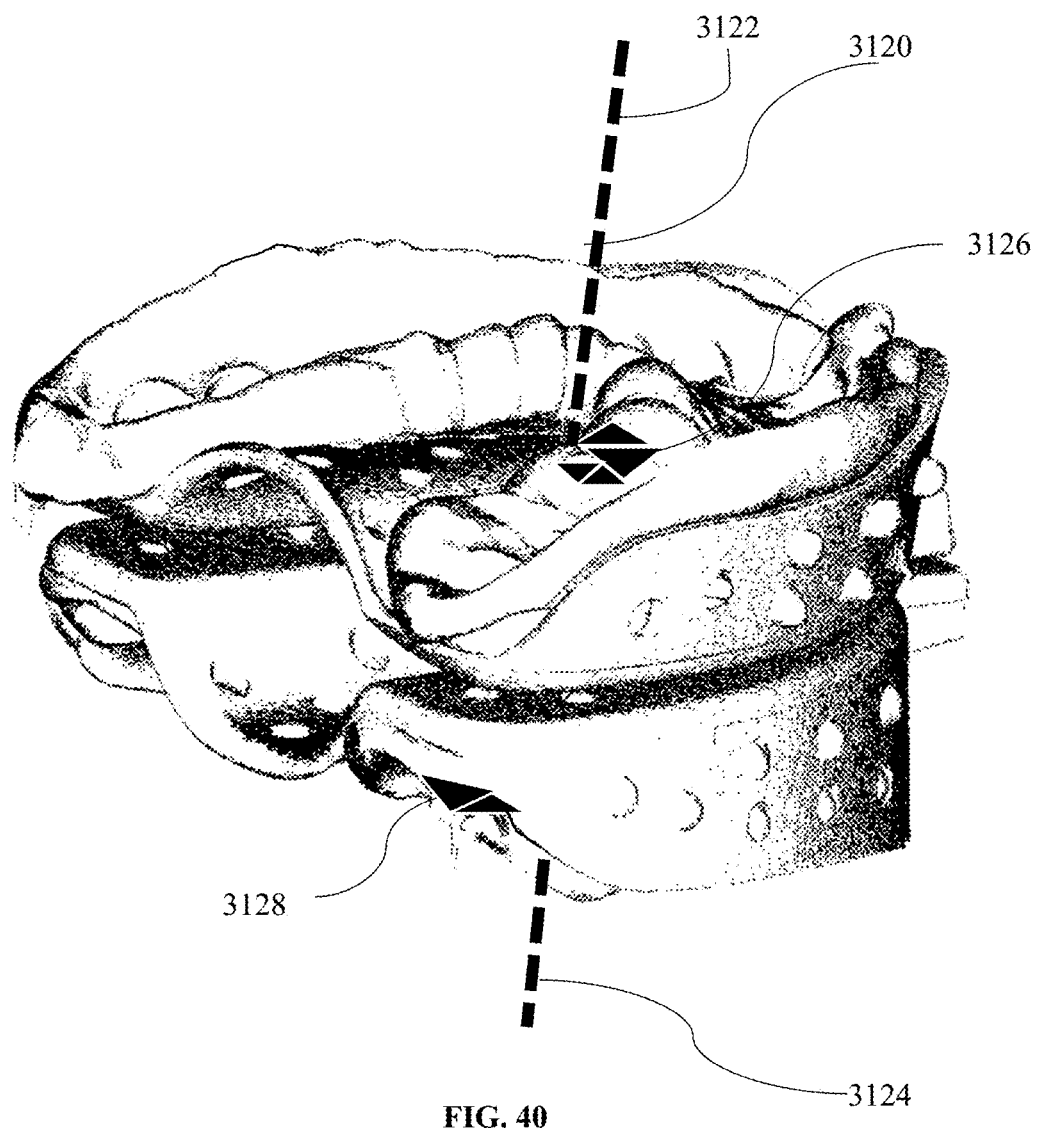
FIG. 40 is a 3D digital model illustrating an example of visible triangles on a surface of two full arch impressions.

For example, as illustrated in the example of FIG. 40, the computer-implemented method can determine one or more first digital surface regions 3126 on a first side 3122 of the single digital surface 3112 around the occlusion axis 3120 and one or more second surface regions 3128 on a second side 3124 of the single digital surface 3112. The computer-implemented method can determine each of the first digital surface regions 3126 visible in the second digital surface regions 3128 as unattributed. As illustrated in the example of FIG. 40, the digital surface regions (both labeled and unlabeled) can be, for example, digital surface mesh triangles. The surface regions and surface mesh triangles illustrated in FIG. 40 and are for illustrative purposes only.

In some embodiments, the computer-implemented method can segment the digital dental impression surface in three dimensions (3D) using curvature based segmentation as described previously in this disclosure. Curvature based segmentation in some embodiments can include determining surface curvature of the one or more first, second, and unattributed digital surface regions and joining the one or more regions into one or more segments. This can include, for example, watershed segmentation as described in this disclosure.

After performing segmentation of digital surface regions, the digital surface mesh can contain a large number of segments as described previously in this disclosure. The number of segments can be reduced by the computer-implemented method by merging two or more segments together. In some embodiments, the computer-implemented method can merge small segments into larger ones based on their curvature, area, perimeter, and other metrics as described previously in the present disclosure.

In some embodiments segmentation by the computer-implemented method can classify the one or more smaller segments as non-anatomical imprints for exclusion from the digital dental impression as described previously in the present disclosure.

Figure 41:
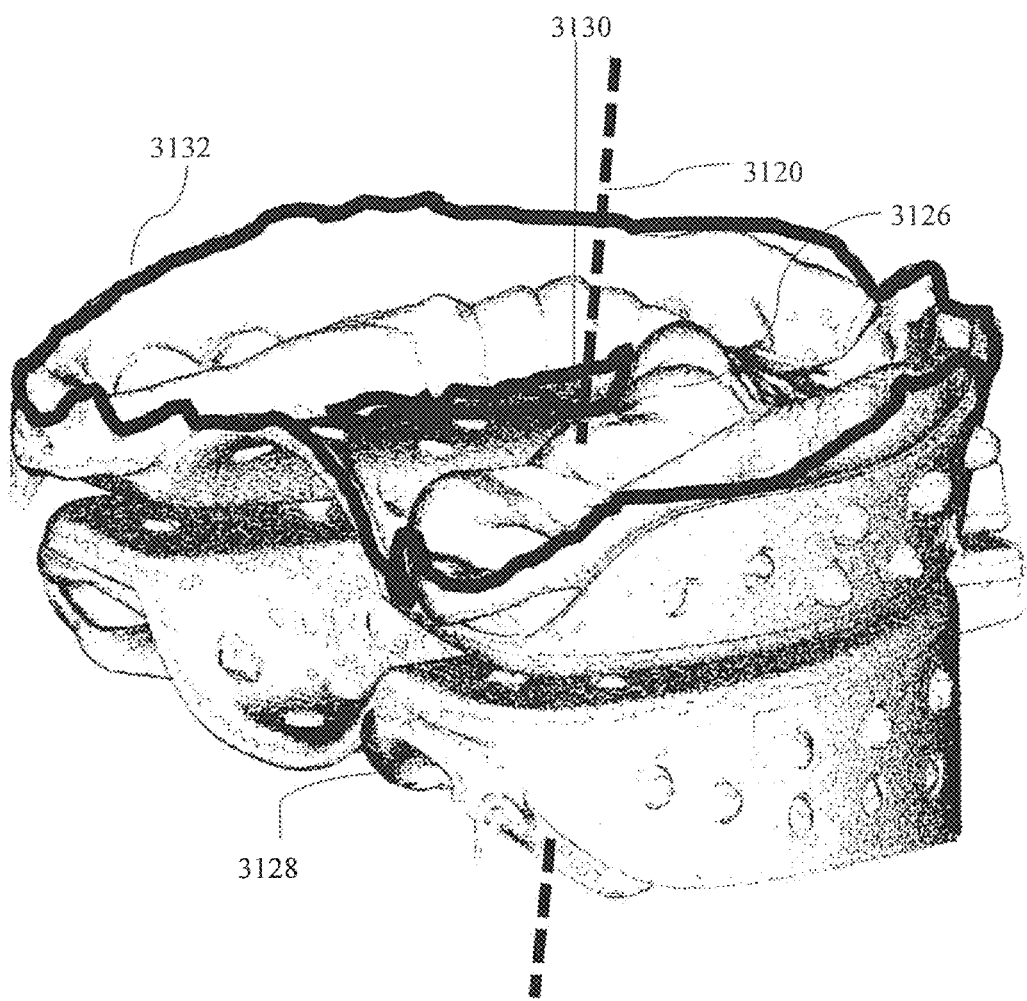
FIG. 41 illustrates an example of a 3D digital model segment.
Figure 42:
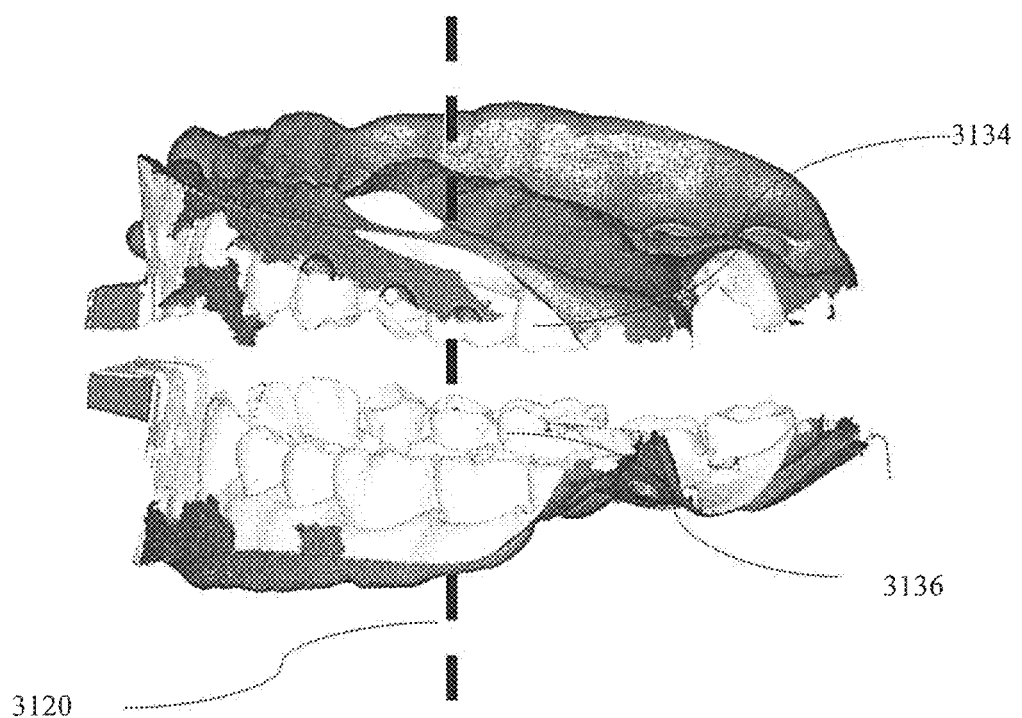
FIG. 42 is a 3D digital model of digitally separated full arch impressions.

In some embodiments, a largest connected component among the first and second set of surface regions 3126 and 3128 can be selected by the computer-implemented method to disconnect or split the digital surfaces of both jaws. For example, a largest connected component 3132 as shown in FIG. 41 among the first surface regions 3126 can be used to split digital jaw surfaces as illustrated in FIG. 42 into a first jaw 3134 and a second jaw 3136.

One advantage of scanning two full arch physical impressions together is to reduce the occupancy of the CT scanner and therefore decrease the time required to scan the full arch physical impressions, for example. This can increase efficiency by allowing for more scans in the same period of time, for example.

Figure 43:
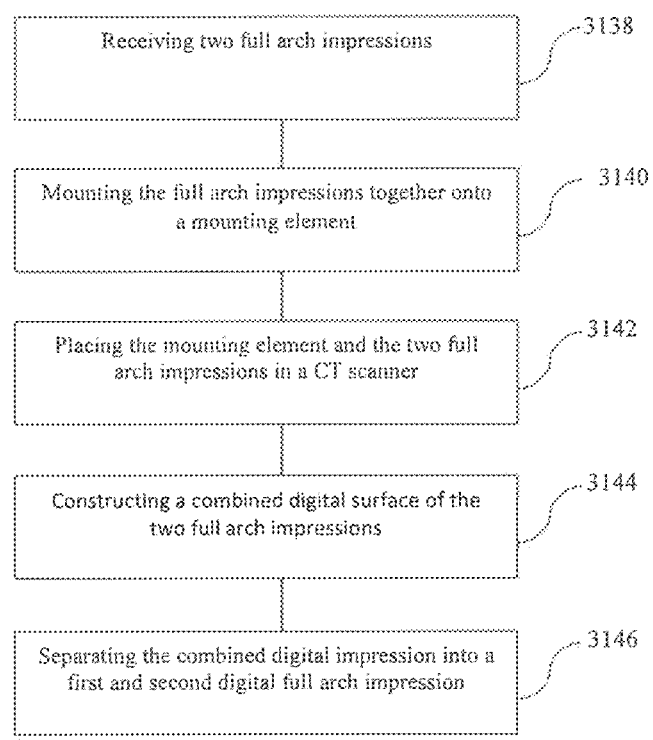
FIG. 43 is a flow chart of a method of scanning two full arch physical impressions.

As illustrated in FIG. 43, also disclosed is a method of scanning two full arch physical impressions together in some embodiments. The method includes receiving two full arch physical impressions 3138, mounting the full arch physical impressions together onto a mounting element 3140, placing the mounting element and the two full arch physical impressions in a CT scanner 3142, constructing a combined digital surface of the two full arch physical impressions 3144, and splitting the combined digital dental impression into a first and second digital full arch impression 3146.

Extraneous Digital Surface Regions

Figure 44A:
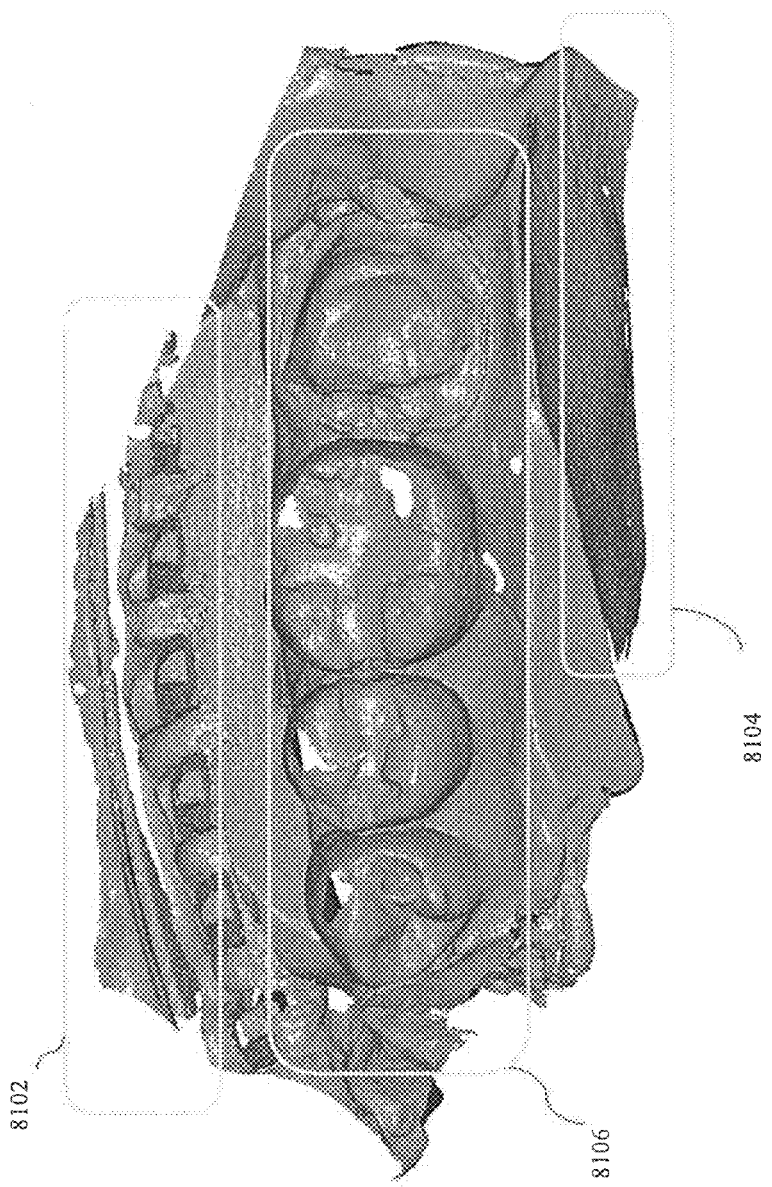
FIG. 44(a) is an example of digital model with extraneous regions.
Figure 44B:
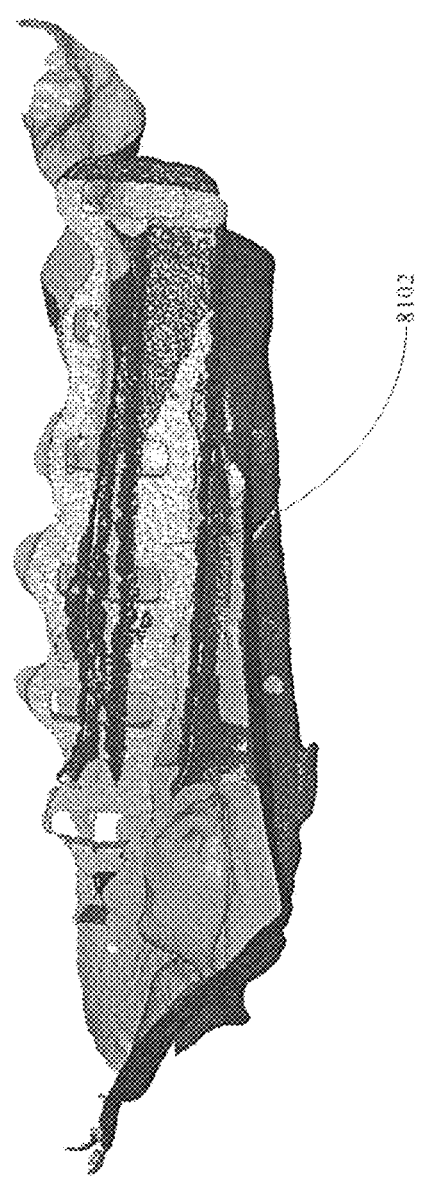
FIG. 44(b) is a side view of a digital model of an example extraneous region.

Digital dental impressions can contain extraneous data that may not be useful for dental processing. This extraneous data can represent walls and other extra material, for example. FIG. 44(a) illustrates a digital dental impression model that includes a region of extraneous material 8102 and 8104 such as walls, for example, along with a teeth and gum area 8106 of the digital impression. FIG. 44(b) further illustrates a digital impression model showing the extraneous material 8102 from the side.

The extraneous material 8102 can interfere with and slow down digital processing of the digital dental model and therefore preferably is partly or entirely removed. In some embodiments, the areas of interest such as the teeth and gum areas 8106 can be determined and retained, while any extraneous areas such as 8102 and 8104 can be removed or excluded, thereby providing a digital dental model with more useful information. The removal of extraneous material 8102 can be performed during generation of the dental digital model automatically, or can be applied to an already generated dental digital model automatically or by a user action, such as selecting a menu option or clicking a button through an input device to remove the extraneous material 8102. In some embodiments, one or more of the features can be performed automatically, for example.

In some embodiments, a computer-implemented method of automatically detecting and removing extraneous material from a digital dental impression can include, for example, receiving a digital dental impression. In some embodiments, the digital dental impression can be received by a computer system from digital storage media. For example, the digital dental impression can be received as a digital file over the network or from internal or external storage media. In some embodiments, a physical impression can be scanned by a CT scanning system and directly provided, for example.

In some embodiments, the computer-implemented method can detect one or more dental features in the digital dental impression. The dental features can be tooth cusps, for example. Teeth typically have at least one cusp on an occlusal surface. For example, canines can have one cusp, maxillary premolars and the mandibular first premolars can typically have two cusps, mandibular second premolars can have three cusps (one buccal and two lingual). Maxillary molars can have two buccal cusps and two lingual cusps and mandibular molars can have four or five cusps. Accordingly, detection of cusps such in the digital dental model can provide an indication of the location of one or more teeth. Detecting the location of cusps is described in the Cusp Detection section of the present disclosure.

In some embodiments, the computer-implemented method filters one or more dental features in a digital model of a digital dental impression. In some embodiments, the computer-implemented method filters cusps by evaluating each candidate-cusp point to determine whether the candidate-cusp point is a tooth cusp. If a cusp is not a tooth-cusp, then the computer-implemented method does not use the non-tooth cusp in further processing. If the cusp is a tooth-cusp, then the computer-implemented method uses the tooth-cusp in further processing.

Figure 45A:
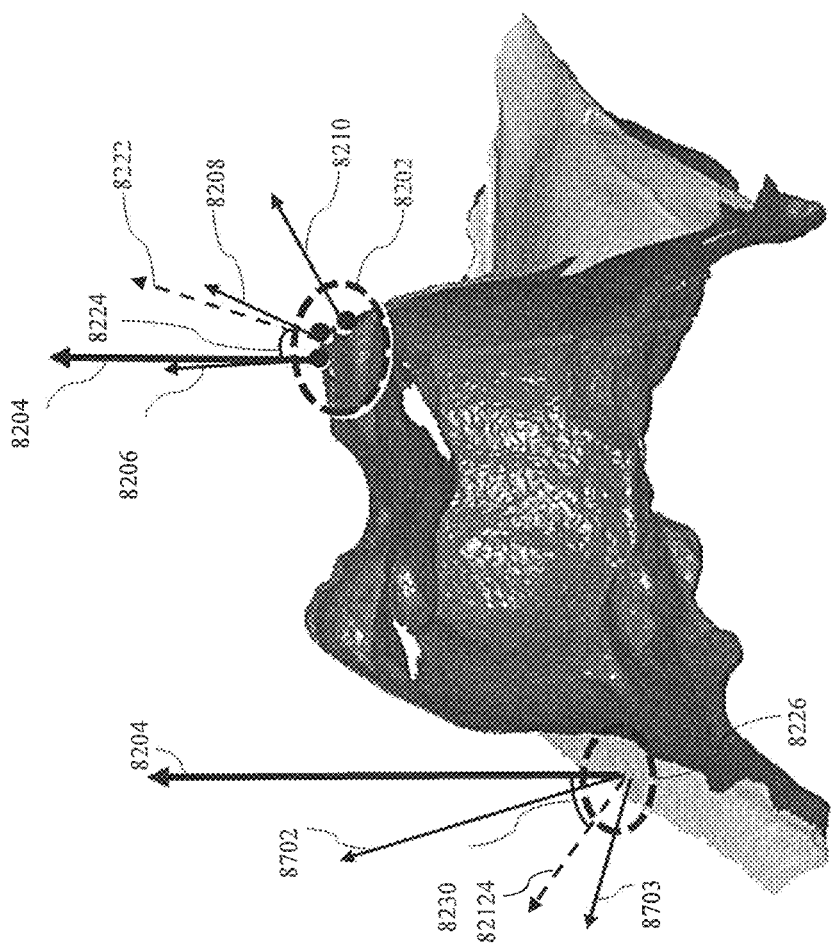
FIG. 45(a) is a 3D digital model example of a single tooth with cusp regions.
Figure 45B:
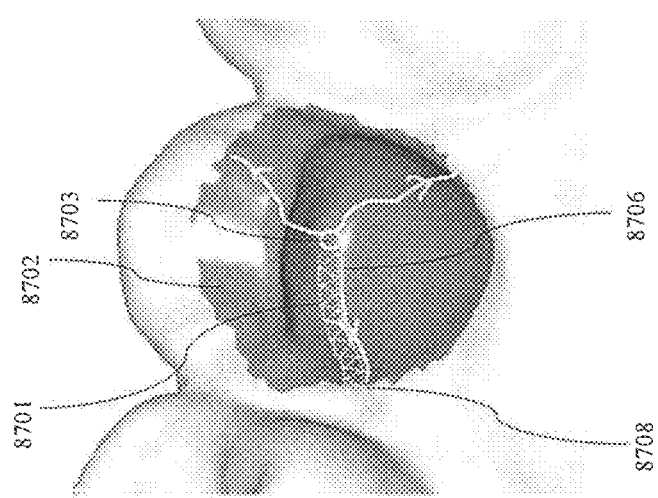
FIG. 45(b) is a 3D digital model example of a single tooth illustrating examples of shortest paths.
Figure 45C:
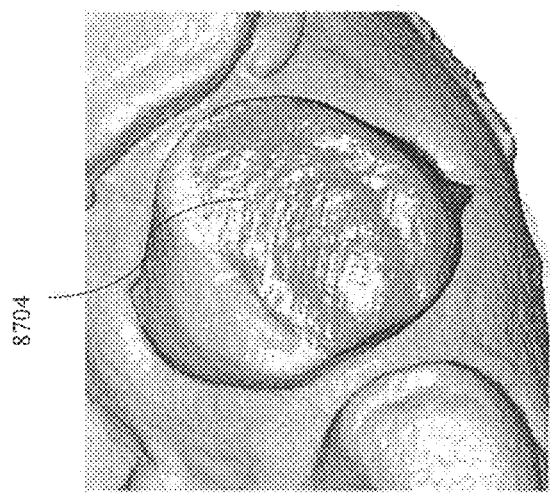
FIG. 45(c) is a 3D digital model example of a single tooth illustrating a 2D region.

As illustrated in FIG. 45(*a*), the computer-implemented method can determine cusp regions as described previously. In some embodiments, candidate cusp-points can be located on parts of the digital surface other than teeth. For example, candidate-cusp points can be located on gum areas, planar base, or walls of the digital model. In some embodiments, the computer-implemented method can filter out candidate cusp-points not located on the teeth. The computer-implemented method can filter cusps by an angle between a cusp-region average normal and an occlusion direction in some embodiments. The computer-implemented can filter cusps comprises filtering by ratio of surface area in 3D to a visible 2D surface area from occlusion direction in some embodiments.

In some embodiments, the computer-implemented method can filter one or more cusp regions by angle to determine if the cusp region is a tooth cusp or a non-tooth cusp. In some embodiments, the angle can be between a cusp-region average normal and the occlusion axis. For example, the computer-implemented method can determine a cusp-region as several local maxima as described previously, each of the local maxima having a normal. The computer-implemented method can determine a cusp-region average normal of the local maxima for a user-selectable radius. For example, the user-selectable radius can be 1 mm around a candidate cusp-point in some embodiments. In some embodiments, the user-selectable radius can be more or less than 1 mm. The computer-implemented method can determine an angle between the cusp-region average normal and the occlusion direction. If the angle exceeds a user-selectable normal threshold angle, then the computer-implemented method can determine that the cusp region is not a tooth cusp region. The computer-implemented method can exclude non-tooth cusp regions from further processing. If the angle is within a user-selectable normal threshold angle, then the computer-implemented method determines that the cusp region is a tooth cusp region. The computer-implemented method can include tooth cusp regions in further processing.

For example, as illustrated in FIG. 45(*a*), the computer-implemented method can determine cusp region 8202 and several local maxima normals 8206, 8208, and 8210. The computer-implemented method can determine the average normal of cusp region 8202 to be average normal 8222 based on the local maxima normal 8206, 8208, and 8210. The computer-implemented method can determine average normal 8222 having average normal angle 2224 with respect to occlusion direction 8204. In some embodiments, the computer-implemented method can determine a cusp region is a tooth-cusp region if the average normal angle 2224 does not exceed a user-selectable normal angle threshold. For example, in some embodiments, the computer-implemented method can determine a cusp-region to be a tooth cusp region if the average normal angle 2224 does not exceed the normal threshold angle of 30 degrees. In some embodiments, the normal threshold angle can be greater or less than or equal to 30 degrees. In the example of FIG. 45(*a*), the computer-implemented method can determine that the cusp region 8202 is a tooth-cusp and retain the cusp region 8202 for further processing.

The computer-implemented method can filter each cusp region. For example, the computer-implemented method can determine cusp region 8226, which includes local maxima 8702 and 8703. The computer-implemented method can determine average normal 8212 for the local maxima of cusp region 8226, for example, which can form average normal angle 8230 with respect to the occlusion orientation 8204. If the average normal angle 8230 is greater than the user-selected normal threshold angle, then the computer-implemented method determines the cusp region 8226 to be a non-tooth cusp region and removes it from further processing.

In some embodiments, the computer-implemented method can also filter one or more cusp regions based on a surface area ratio between a three dimensional region (3D) of a candidate cusp point and the two dimensional (2D) region of the candidate cusp point from the occlusal direction. For example, as illustrated in FIG. 45(*b*), the computer-implemented method can filter one or more cusp regions by determining a candidate cusp ratio of a region area in 3D to a region area in 2D from the occlusion direction. In some embodiments, the computer-implemented method determines the candidate cusp ratio as follows:

candidate cusp ratio=(3*D* surface area)/(2*D* surface area).

In some embodiments, the computer-implemented method can determine surface region boundaries and surface areas of regions based on the triangles or other shape comprising the digital surface mesh. For example, as illustrated in FIG. 45(*b*), the computer-implemented method can include a digital surface mesh of triangles 8701. The digital surface mesh of triangles 8701 are representatively displayed for illustrative purposes. The computer-implemented method can with a user-selectable predefined radius determine a 3D region 8702 around a candidate cusp point 8703, for example, by determining one or more radius paths 8706 along edges of one or more adjacent triangles of the digital surface mesh. As illustrated in the figure, the boundary of the 3D region 8702 is defined by the user-selectable predefined radius around the candidate cusp point 8703 along such that a shortest radius path 8706 contained in the 3D region 8702 from the candidate cusp point 8703 to any boundary point 8708 is not more than the user-selectable predefined radius. In some embodiments, the user-selectable predefined radius can be, for example, 5 mm. The computer-implemented method then determines the 3D surface area of the 3D region 8702. In some embodiments, the computer-implemented method can determine the 3D surface area by summing the areas of each of the digital triangles in the 3D region 8702. Using the same boundaries as the 3D region 8702, the computer-implemented method determines a 2D region surface area of the 2D region 8704 of the same candidate cusp point from the occlusal axis as illustrated in FIG. 45(*c*). In some embodiments, the computer-implemented method can determine the 2D surface area by summing the areas of each of the digital triangles in the 2D region 8704. The computer-implemented method then determines the candidate cusp ratio as (3D surface area)/(2D surface area). If the candidate cusp ratio of the is below a user-selectable minimum threshold ratio, then the computer-implemented method determines that the cusp region is substantially planar and is therefore not a tooth cusp region and removes the cusp region from further processing. In some embodiments, the user-selectable minimum threshold ratio can be, for example close to 1.25. If the ratio is above a user-selectable maximum threshold ratio, then the computer-implemented method determines that the candidate peak is a narrow peak extended along the occlusion direction (present in some "walls"), and is therefore not a tooth cusp region and remove the cusp region from further processing. In some embodiments, the maximum threshold ratio can be, for example, 5.0.

The computer-implemented method can apply one or more of the filters to every candidate cusp point to determine the tooth cusps as described in the present disclosure.

In some embodiments, the computer-implemented method can digitally join the one or more dental features. The computer-implemented method can digitally join the one or more dental features by constructing a best fit smooth curve or a polyline passing through or close to a maximum number of the dental features, for example. For example, in the case of dental features being tooth cusps, the computer-implemented method can digitally join the tooth cusps by constructing a best fit smooth curve or a polyline passing through or close to a maximum number of tooth cusps. In some embodiments, the computer-implemented method digitally joins filtered dental features such as, for example, tooth cusps.

Figure 46A:
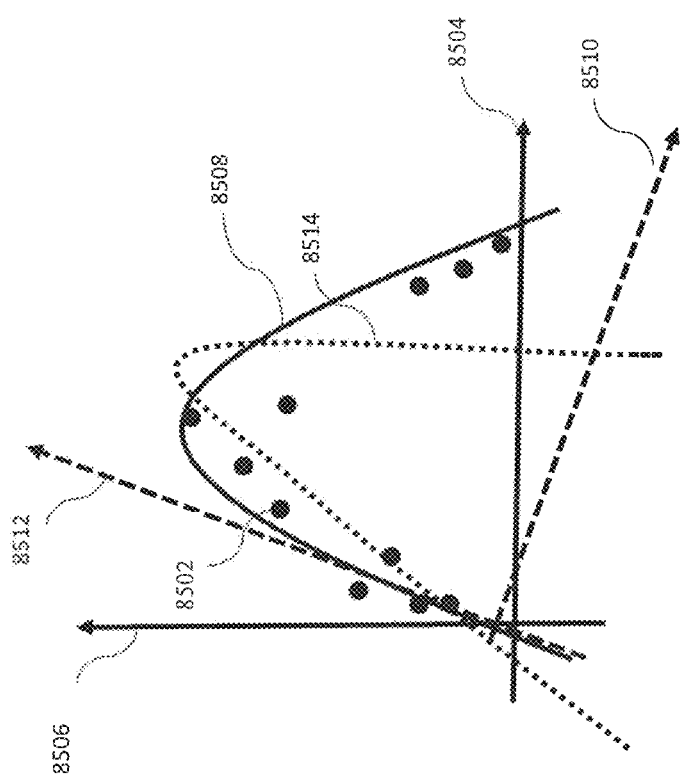
FIG. 46(a) is a graph illustrating an example of determining a best fit parabola.
Figure 46B:
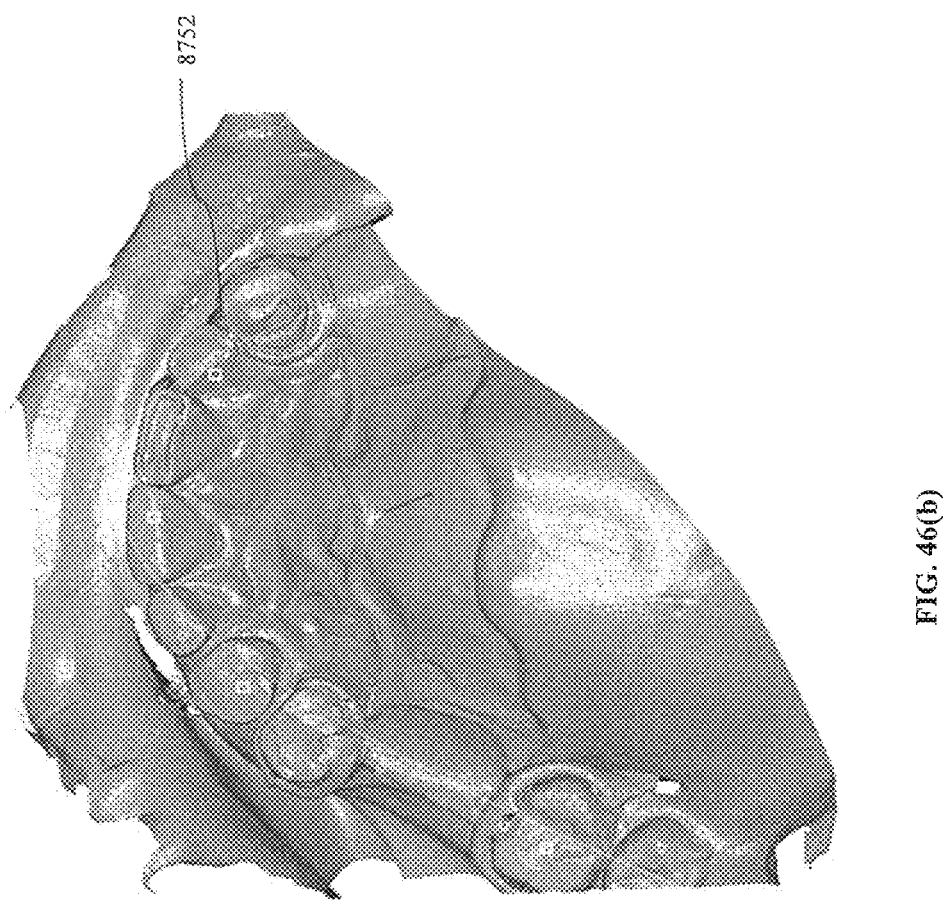
FIG. 46(b) is a 3D digital model example of a best fit parabola.

In some embodiments, the computer implemented method can join the one or more dental features by the best fit smooth curve such as a best fit analytical curve such as, for example, a parabola, an ellipse, or hyperbola. To determine the best fit parabola, the computer-implemented method determines the least-squares plane for all digital dental features. For example, in the case of cusps, the computer-implemented method projects the tooth cusps onto the plane. For example, as illustrated in FIG. 46(*a*), cusps 8502 (illustrated as black dots in the figure) are arranged in the least-squares plane. The computer-implemented method generates a first x-axis 8504 in a first direction in the plane and determines a first y-axis 8506 ninety degrees to the x-axis 8506 in the plane. The computer implemented method determines coefficients a, b, and c in the formula $y=ax^2+bx+c$ using the Quadratic Least Square Regression known in the art. For example, parabola 8508 can be determined by the computer-implemented method after determining coefficients a, b, and c. The computer-implemented method then determines the discrepancy between the parabola 8508 and the cusps 8502, for example. The computer-implemented method repeats the steps for a user-selectable number of x-axis directions. For example, the computer-implemented method can rotate the x-axis 8504 by an x-axis rotation to a new x-axis 8510 with corresponding y-axis 8512 to determine parabola 8514. In some embodiments, the number of x-axis directions can be a user-selectable and/or pre-defined value. In some embodiments, the number of x-axis directions can be 100, for example. The computer-implemented method can select the parabola with the smallest discrepancy where a is not more than 150 meter$^{-1}$, for example, to avoid very sharp parabolas. In some embodiments, the computer-implemented method optionally eliminates cusps located farther than a user-selectable and/or pre-defined maximum cusp distance, which can be any value. In some embodiments, the maximum cusp distance can be, for example, 5 mm. As illustrated in FIG. 46(*b*), the computer-implemented method can join tooth cusps by the best fit parabola 8752.

In some embodiments, the computer-implemented method can join the tooth cusp regions together by segments which together make up a polyline. In some embodiments, the computer-implemented method can join a maximal subset of found and filtered cusps by minimizing the summed angle between successive polyline segments. In some embodiments, the computer-implemented method assigns one or more penalty values based on how segments connect cusp-points. For example, in some embodiments, the computer-implemented method assigns a terminal cusp penalty for a terminal cusp-point in the polyline. In some embodiments, the terminal cusp penalty can be zero. In some embodiments, the computer-implemented method assigns an internal cusp penalty for an internal cusp-point included in the polyline equal to the angle the polyline makes at that point, for example. The computer-implemented method assigns a user-selectable cusp-exclusion penalty for a cusp-point not included in the polyline to be equal to a user-selectable penalty value. In some embodiments, the cusp-exclusion penalty can be 50 degrees, for example. A higher cusp-skipping penalty will tend to include more cusps in the polyline. A lower cusp-skipping penalty will tend to create more straight polyline with more cusps skipped. In some embodiments, the computer-implemented method determines a total polyline penalty by summing the terminal cusp penalty, the cusp-exclusion penalty, and the internal cusp penalty for the given polyline. In some embodiments, the computer-implemented method connects cusps with segments to form the polyline with a minimum total polyline penalty. In some embodiments, the computer-implemented method can use dynamic programming to determine the minimum total polyline penalty.

For example, in some embodiments the computer-implemented method generates an ordered list of candidate cusp points by constructing a smooth curve, projecting all cusps on the smooth curve, and determining an order of the cusps from the projection location on the smooth curve. In some embodiments, the smooth curve is a parabola. However, any smooth curve can be used.

In some embodiments, the computer-implemented method receives the ordered list of candidate cusp points and the cusp-exclusion penalty, P. The computer-implemented method generates a 2D grid with the dimensions: [0,the number of cusps−2) by [0,the number of cusps).

Each cell (i,j) of the grid represents the best polyline from i+3 cusps ending at cusp #j. The computer-implemented method stores 3 types of values in each cell (i,j) of the grid: total polyline penalty, which is the penalty of the best polyline from i+3 cusps ending at cusp #j; prevCusp, which is the index of the next to last cusp in the best polyline; and prevPrevCusp, which is the index of the cusp two cusps from the last cusp in the best polyline.

The computer-implemented method fills the cells (0,j) representing polylines from 3 cusps only. The computer-implemented method puts large penalties in cell(0,0) and cell(0,1), because they represent less than 3-cusp polylines. In some embodiments, a large penalty can be for example, a value larger than the total number of the cusp points multiplied by the cusp-exclusion penalty. The computer-implemented method for every cell (0,j) considers all cusps #f and #m, such that f<m<j, and determines the polyline (cusp #f to cusp #m to cusp #j) having the smallest angle. The penalty written in the grid by the computer-implemented method is equal to the smallest angle plus (j−2)*P.

Next, the computer-implemented fills the cells (i,j), where i>0 represents polylines with 4+ cusps. The computer-implemented method assigns large penalties in cells(i,0), because there cannot be a 3-cusp polyline ending at cusp #0. In some embodiments, a large penalty can be for example, any value larger than the total number of the total number of cusp points multiplied by the cusp-exclusion penalty. For every cell (i,j), the computer-implemented method considers all k cusps, such that k<j. The computer-implemented method considers the best polyline defined by cell(i−1,k), which ends at cusp #k, with the extension of cusp #j at the end. The penalty of this extended polyline is: cell(i−1,k)·penalty+angle(cell(i−1,k)·prevCusp, k, j)+(j−k−1)*P. The computer-implemented method finds the smallest penalty for all k, and put the data corresponding to it in cell(i,j).

Next, the computer-implemented method finds the minimal penalty in the grid as follows:

Step 1: Consider final skipped cusps as follows:
a. For all i and j, the total penalty is cell(i,j)·penalty+(the number of cusps−1−j)*P.
b. Find the (i,j) corresponding to minimal total penalty as defined in the previous step.

Step 2: Output the polyline from the endpoint to the beginning:
a. i and j are from Step 1(b).
b. Output cusp #j
c. Output cusp #cell(i,j)·prevCusp
d. If i==0 then output cusp #cell(i,j)·prevPrevCusp and stop
e. j=cell(i,j)·prevCusp
f. i=i−1
g. go to Step 2(b).

Figure 46C:
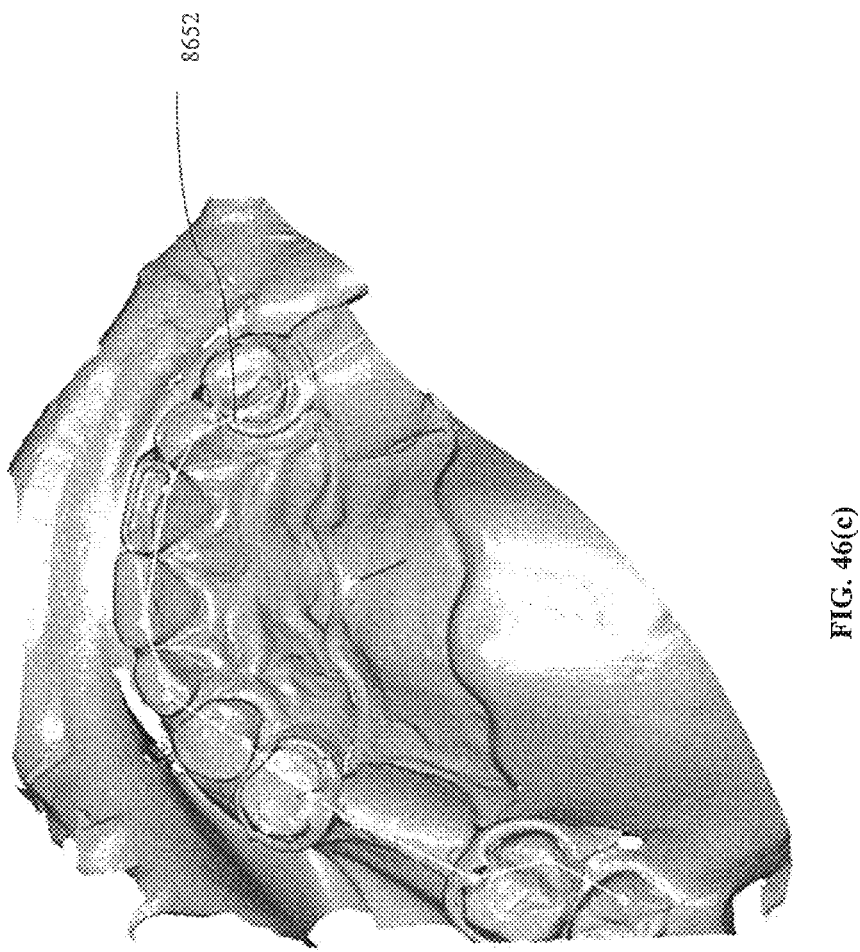
FIG. 46(c) is a 3D digital model example of a best fit polyline.

After a smooth curve or polyline is received, the cusp-points located farther from the curve or polyline than the predefined distance can be eliminated and methods I. and/or II. repeated for gaining better precision of the arch. As illustrated in FIG. 46(c), the computer-implemented method can join the dental features such as tooth cusps by a polyline 8652.

In some embodiments, the smooth curve can be an ellipse. One example of fitting ellipses is described in the article DIRECT LEAST SQUARES FITTING OF ELLIPSES by Andrew W. Fitzgibbon, Maurizo Pilu, and Robert B. Fisher at the Department of Artificial Intelligence, The University of Edinburgh on Jan. 4, 1996, the entirety of which is hereby incorporated by reference.

For example, in some embodiments, the computer-implemented method can determine ellipses as follows:

Given N points on the plane: $(p_x^i, p_y^i)$

The steps of ellipse fitting algorithm:

$$\text{Let } 6 \times 6 \text{ matrix } C = \begin{bmatrix} 0 & 0 & 2 & 0 & 0 & 0 \\ 0 & -1 & 0 & 0 & 0 & 0 \\ 2 & 0 & 0 & 0 & 0 & 0 \\ 0 & 0 & 0 & 0 & 0 & 0 \\ 0 & 0 & 0 & 0 & 0 & 0 \\ 0 & 0 & 0 & 0 & 0 & 0 \end{bmatrix}$$

Construct Nx6 matrix D, with every row defined as $$D_i = [p_x^i p_x^i\ p_x^i p_y^i\ p_y^i p_y^i\ p_x^i\ p_y^i\ 1]$$

Compute 6×6 matrix $S = D^T D$

Compute all 6 eigenvalues $\mu_j$ of the matrix $S^{-1}C$ and corresponding eigenvectors $s_j$ For each positive real eigenvalues compute a. $u_j = \dfrac{1}{\sqrt{s_j^T C s_j}}$ b. $v_j = u_j^2 s_j^T S s_j - \mu_j$ Find index j corresponding to the minimal value $|v_j|$ The best coefficients of the ellipse $ax^2+bxy+cy^2+dx+ey+f=0$ are $[a\ b\ c\ d\ e\ f] = u_j s_j^T$ In some embodiments, the computer-implemented method can determine one or more regions of interest from the joined one or more digital dental features. In some embodiments the one or more regions of interest can include tooth and gum regions, for example.

In some embodiments, the computer-implemented method can determine one or more regions of interest such as, for example, tooth and gum regions based on the joined digital dental features such as tooth cusps. The computer-implemented method receives a smooth curve or polyline and the digital dental impression and determines a tooth and gum region and an extraneous material region to remove. In some embodiments, determining one or more regions of interest includes starting at an initial cusp point on the smooth curve or polyline and growing the regions of interest such as teeth and gum regions until a cutoff value. In some embodiments, the cutoff value can be a user-selectable distance from the initial cusp point. In some embodiments, the cutoff value can be a feature of the digital dental impression, such as a lowest point along one or more paths on the digital surface with respect to an occlusion axis of the digital dental impression.

In some embodiments, the computer-implemented method can determine one or more regions of interest such as, for example, tooth and gum regions, by determining a first region having an initial point-set of either filtered cusp-points or points of the dental arch projected on the digital surface and finding all points on the digital surface that can be reached by a path along the digital surface from the initial set, with the upper limit of a user-selectable path length parameter that can be set to any value. In some embodiments, the user-selectable path length can be, for example, 10 mm. In some embodiments, the computer-implemented method can determine a first region using a multi-source variant of Dijkstra's algorithm. For example, the computer-implemented method can determine the first region as follows:

1. Mark all digital surface points as unvisited. Create a set of all the unvisited digital surface points called the unvisited set.

2. Assign to every digital surface point a tentative distance value: set the tentative distance value to zero for all digital surface points associated with initial cusp digital surface points and to infinity for all other digital surface points. Set any of the initial digital surface points as current.

3. For the current digital surface point, consider all unvisited neighbors and calculate each unvisited neighbor's tentative distance through the current digital surface point. Compare the newly calculated tentative distance to the current assigned value and assign the smaller one. For example, if the current digital surface point A is marked with a distance of 6, and the edge connecting it with a neighboring digital surface point B has length 2, then the distance to neighboring B through A will be 6+2=8. If digital surface point B was previously marked with a distance greater than 8 then change it to 8. Otherwise, keep the current value.

4. When all of the unvisited neighbors of the current digital surface point are considered, mark the current digital surface point as visited and remove it from the unvisited set. A visited digital surface point will never be checked again.

5. If the smallest tentative distance among the digital surface points in the unvisited set is more than a parameter then stop. In some embodiments, the parameter can be 10 mm, for example. Output the region of all visited digital surface points.

6. Otherwise, select the unvisited digital surface point that is marked with the smallest tentative distance, set it as the new "current digital surface point", and go back to step 3.

After determining the first region, the computer-implemented method determines a second region extending from the first region. In some embodiments, the computer implemented method can determine the second region using the same steps described for determining the first region. However, the initial digital surface points in the second region are the digital surface endpoints of the first region. The computer-implemented method determines the forest of shortest paths on the digital surface starting at the digital surface endpoints from region A and terminating at second region digital surface endpoints. The second region path length can also be limited by a user-selectable second region path length parameter. In some embodiments, the second region path length can be any distance, such as, for example, 10 mm. In some embodiments, the second region includes only digital surface points along the shortest path to a lowest point with respect to the occlusion axis on the digital surface. In some embodiments, the second region digital surface endpoints are the lowest point with respect to the occlusion axis.

Figure 47:
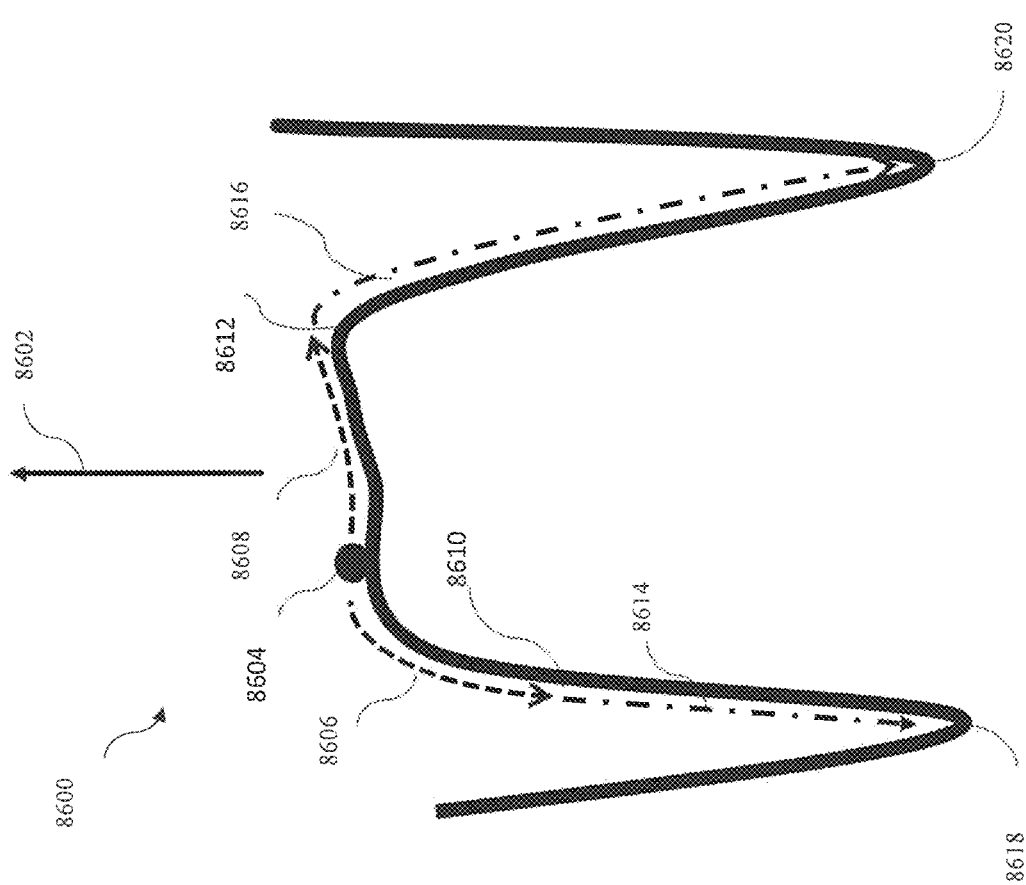
FIG. 47 is a 2D cross section of a 3D virtual single tooth example illustrating an example of determining regions of interest.

FIG. 47 illustrates an example of one embodiment of removing extraneous digital surface regions. FIG. 47 shows a cross section view of a digital surface impression with digital tooth 8600 having an occlusion direction 8602 and an initial cusp point 8604. In some embodiments, the initial cusp point 8604 is part of a group of initial cusp points connected together by smooth curve or polyline as described in the present disclosure. In some embodiments, the initial cusp point can be one or more digital surface points.

The computer-implemented method determines a first region of interest by generating first region paths 8606 and 8608 from the initial cusp point 8604 and extending along the digital surface until reaching the first region endpoints 8610 and 8612, respectively. In this example, the first region endpoints 8610 and 8612 are located at a cutoff value of a cutoff distance from the initial cusp point 8604. In some embodiments, this can be, for example, 10 mm.

Figure 48A:
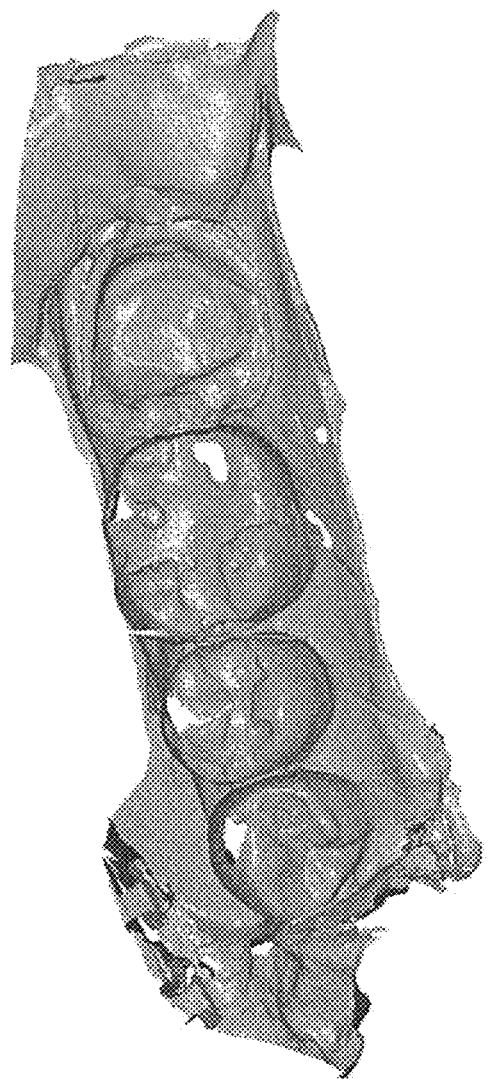
FIGS. 48(a) and 48(b) are a 3D digital model examples of example regions of interest.
Figure 48B:
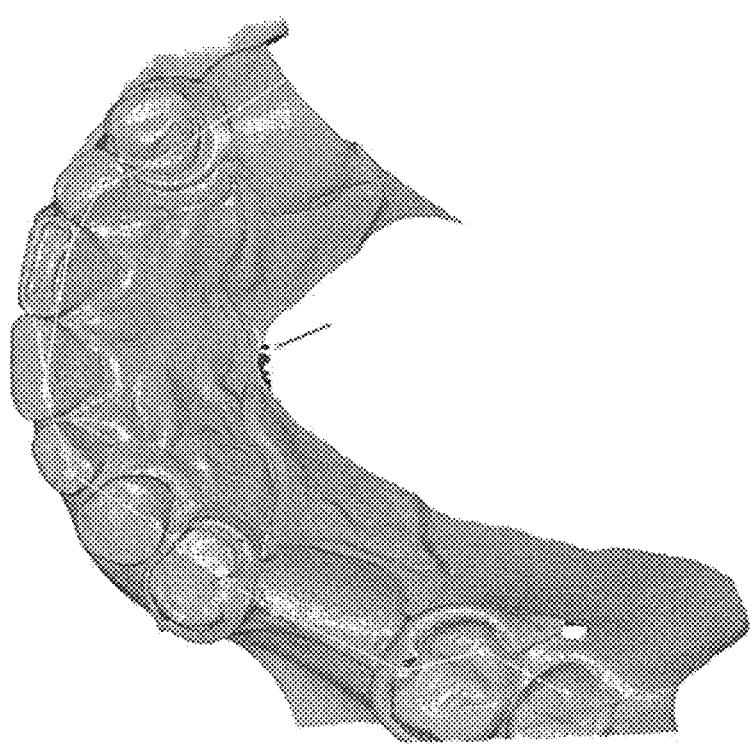

The computer-implemented method determines a second region of interest by generating second region paths 8614 and 8616 from the first region endpoints 8610 and 8612 and extending along the digital surface until reaching the second region endpoints 8618 and 8620, respectively. In this example, the second region endpoints 8618 and 8620 are located at a cutoff value corresponding to lowest points on the digital surface with respect to the occlusion axis. The computer-implemented method can delete all regions outside of the tooth and gum region from the digital dental impression by, for example, retaining only the first and second digital surface regions of interest which in some embodiments include only teeth and gum regions. The computer-implemented method in some embodiments thereby deletes or removes extraneous regions, retaining the teeth and gums. FIGS. 48(a) and 48(b) illustrate examples of teeth and gum areas with extraneous material removed.

EXAMPLES

Several examples of a computer-implemented method processing are described. These examples are for illustrative purposes.

FIG. 49 illustrates one example of a computer-implemented method of digitally processing a digital dental impression. In some embodiments, the computer-implemented method includes detecting one or more dental features in a digital dental impression at 8304, filtering the one or more dental features at 8306, digitally joining the one or more dental features at 8308, determining one or more regions of interest from the joined one or more digital dental features at 8310.

The computer-implemented method can include several optional features. For example, the computer-implemented method can optionally delete all regions outside of the one or more regions of interest from the digital dental impression at 8312. The one or more regions of interest can include a tooth region, for example. The one or more regions of interest can include a gum region, for example.

For example, one or more anatomical dental features can optionally be tooth cusps. The detecting the at least one tooth cusp can include identifying an occlusion axis, and finding surface points based on curvature. The detecting the at least one tooth cusp can include identifying a center of surface regions with several local maxima substantially in a direction of an occlusion direction. The filtering cusps can include filtering by an angle between a cusp-region average normal and an occlusion direction. The filtering cusps can include filtering by ratio of surface area in 3D to a visible 2D surface area from occlusion direction. A ratio below a minimum threshold ratio can be a non-tooth cusp region. A ratio above a maximum threshold ratio can be a non-tooth cusp region. Joining the tooth cusps can include constructing a best curve connecting the tooth cusps. The best curve can be a polyline. The best curve can be a smooth analytical curve. The best curve can include determining a constructive a best curve passing substantially close to a maximal subset of previously found and filtered cusps. The best curve can be an analytical smooth curve. The analytical smooth curve can be one from the group consisting of a parabola, ellipse, or hyperbola. The best curve can be a polyline joining a maximal subset of found and filtered cusps and minimizing summed angle between successive polyline segments. Finding teeth and gum region can include starting at an initial cusp point and growing teeth and gum region until a cutoff value. The cutoff value can be a lowest point along one or more paths on the digital surface with respect to an occlusion axis. The cutoff value can be a fixed distance from the cusp. Finding teeth and gum region can include starting at an initial cusp point and growing teeth and gum region from filtered tooth cusps. Finding teeth and gum region can include starting at an initial cusp point and growing teeth and gum region from arch curve.

Some embodiments include a non-transitory computer readable medium storing executable computer program instructions for digitally processing a digital dental impression the computer program instructions including instructions for: detecting one or more anatomical dental features in a digital dental impression, filtering the one or more anatomical dental features, digitally joining the one or more anatomical dental features, and determining one or more regions of interest from the joined anatomical dental features. In some embodiments, the steps can optionally include deleting all regions outside of the one or more regions of interest from the digital dental impression. In some embodiments, the one or more regions of interest can include a tooth region. In some embodiments, the one or more regions of interest can include a gum region.

Some embodiments include a digital impression processing system for creating a digital model from a CT scan, including: a processor, a computer-readable storage medium including instructions executable by the processor to perform steps including: detecting one or more anatomical dental features in a digital dental impression, filtering the one or more anatomical dental features, digitally joining the one or more anatomical dental features, and determining one or more regions of interest from the joined anatomical dental features. In some embodiments, the steps can optionally include deleting all regions outside of the one or more regions of interest from the digital dental impression. In some embodiments, the one or more regions of interest can include a tooth region. In some embodiments, the one or more regions of interest can include a gum region.

Figure 50:
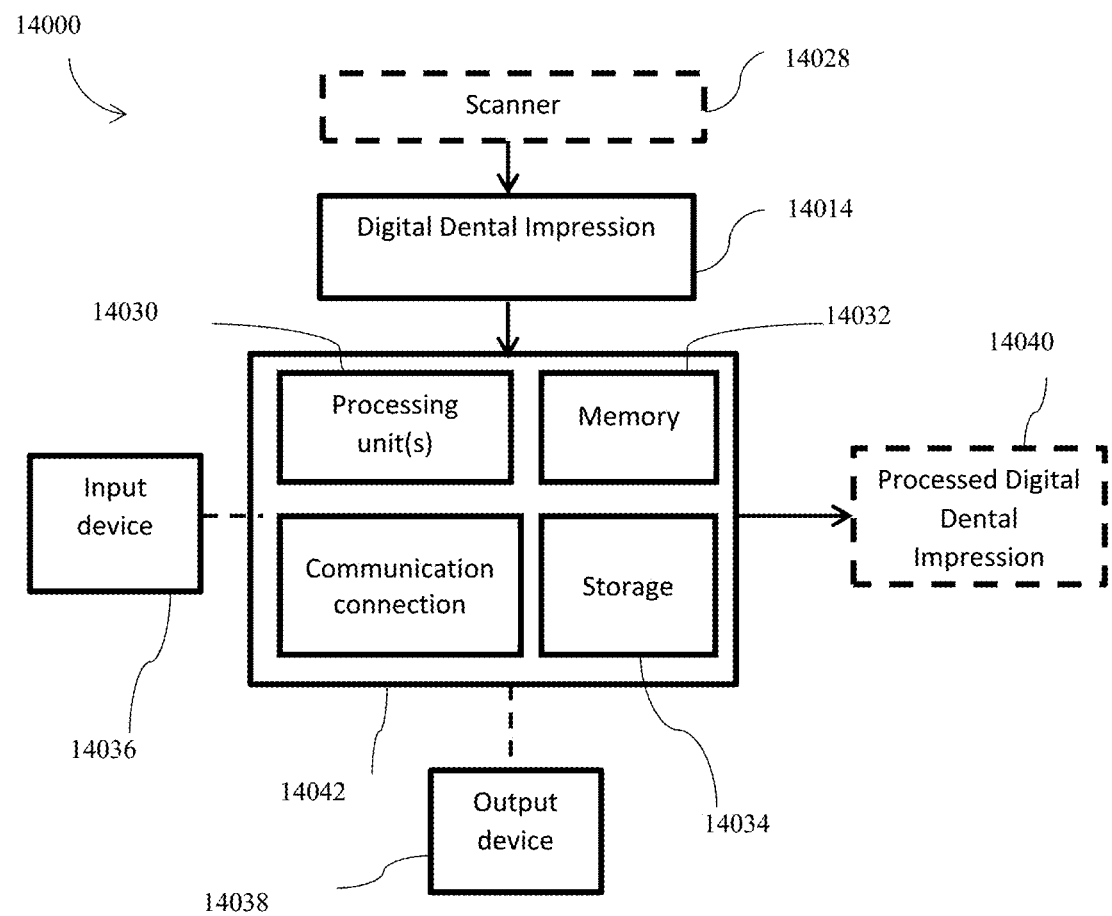
FIG. 50 is an example of a digital dental impression processing system.

FIG. 50 illustrates a digital dental impression processing system 14000 in some embodiments. The system 14000 can include a processor 14030, computer-readable storage medium 14034 having instructions executable by the processor to perform steps described in the present disclosure. The single digital dental impression 14014 can optionally be provided by an optional scanner 14028, for example. The optional scanner 14028 can be a CT scanner or an optical scanner, for example. The digital dental impression processing system 14000 can optionally provide one or more digital models with a processed digital dental impression 14040.

One or more of the features disclosed herein can be performed and/or attained automatically, without manual or user intervention. One or more of the features disclosed herein can be performed by a computer-implemented method. The features—including but not limited to any methods and systems—disclosed may be implemented in computing systems. For example, the computing environment 14042 used to perform these functions can be any of a variety of computing devices (e.g., desktop computer, laptop computer, server computer, tablet computer, gaming system, mobile device, programmable automation controller, video card, etc.) that can be incorporated into a computing system comprising one or more computing devices. In some embodiments, the computing system may be a cloud-based computing system.

For example, a computing environment 14042 may include one or more processing units 14030 and memory 14032. The processing units execute computer-executable instructions. A processing unit 14030 can be a central processing unit (CPU), a processor in an application-specific integrated circuit (ASIC), or any other type of processor. In some embodiments, the one or more processing units 14030 can execute multiple computer-executable instructions in parallel, for example. In a multi-processing system, multiple processing units execute computer-executable instructions to increase processing power. For example, a representative computing environment may include a central processing unit as well as a graphics processing unit or co-processing unit. The tangible memory 14032 may be volatile memory (e.g., registers, cache, RAM), nonvolatile memory (e.g., ROM, EEPROM, flash memory, etc.), or some combination of the two, accessible by the processing unit(s). The memory stores software implementing one or more innovations described herein, in the form of computer-executable instructions suitable for execution by the processing unit(s).

A computing system may have additional features. For example, in some embodiments, the computing environment includes storage 14034, one or more input devices 14036, one or more output devices 14038, and one or more communication connections 14037. An interconnection mechanism such as a bus, controller, or network, interconnects the components of the computing environment. Typically, operating system software provides an operating environment for other software executing in the computing environment, and coordinates activities of the components of the computing environment.

The tangible storage 14034 may be removable or non-removable, and includes magnetic or optical media such as magnetic disks, magnetic tapes or cassettes, CD-ROMs, DVDs, or any other medium that can be used to store information in a non-transitory way and can be accessed within the computing environment. The storage 14034 stores instructions for the software implementing one or more innovations described herein.

The input device(s) may be, for example: a touch input device, such as a keyboard, mouse, pen, or trackball; a voice input device; a scanning device; any of various sensors; another device that provides input to the computing environment; or combinations thereof. For video encoding, the input device(s) may be a camera, video card, TV tuner card, or similar device that accepts video input in analog or digital form, or a CD-ROM or CD-RW that reads video samples into the computing environment. The output device(s) may be a display, printer, speaker, CD-writer, or another device that provides output from the computing environment.

The communication connection(s) enable communication over a communication medium to another computing entity. The communication medium conveys information, such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

Any of the disclosed methods can be implemented as computer-executable instructions stored on one or more computer-readable storage media 14034 (e.g., one or more optical media discs, volatile memory components (such as DRAM or SRAM), or nonvolatile memory components (such as flash memory or hard drives)) and executed on a computer (e.g., any commercially available computer, including smart phones, other mobile devices that include computing hardware, or programmable automation controllers) (e.g., the computer-executable instructions cause one or more processors of a computer system to perform the method). The term computer-readable storage media does not include communication connections, such as signals and carrier waves. Any of the computer-executable instructions for implementing the disclosed techniques as well as any data created and used during implementation of the disclosed embodiments can be stored on one or more computer-readable storage media 14034. The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C++, Java, Perl, Python, JavaScript, Adobe Flash, or any other suitable programming language. Likewise, the disclosed technology is not limited to any particular computer or type of hardware. Certain details of suitable computers and hardware are well known and need not be set forth in detail in this disclosure.

It should also be well understood that any functionality described herein can be performed, at least in part, by one or more hardware logic components, instead of software. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

Furthermore, any of the software-based embodiments (comprising, for example, computer-executable instructions for causing a computer to perform any of the disclosed methods) can be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means.

In view of the many possible embodiments to which the principles of the disclosure may be applied, it should be recognized that the illustrated embodiments are only examples and should not be taken as limiting the scope of the disclosure. Rather, the scope of the invention is defined by all that comes within the scope and spirit of the following claims.

In some embodiments, a CT scanner is arranged to generate a digital dental impression of a physical dental impression.

One advantage of one or more features as described herein and/or claimed is an accurate digital dental model without extraneous data, for example. This can reduce or eliminate unnecessary data that interferes with a dental professional's ability to view, diagnose, and/or manipulate the digital dental model without limitations, thereby making the digital dental model more useful, for example. At least one other advantage of one or more features as described in the disclosure is accurately removing the extraneous digital material on an empirical basis, for example, thereby providing a more accurate digital dental model of regions of interest such as teeth and gums, for example. At least one other advantage of one or more features as described in this disclosure and/or claimed is a more accurate digital surface of a digital dental impression, for example. One advantage other of one or more features as described herein is more accuracy of one or more digital dental impression jaws by, for example, increased granularity in determining features of the digital model and/or removing non-anatomical features, for example.

What is claimed is:

1. A computer-implemented method of automatically detecting and removing extraneous material from a digital dental impression, comprising:
   detecting one or more dental features in a digital dental impression;
   filtering the one or more dental features;
   digitally joining the one or more dental features; and
   determining one or more regions of interest from the joined one or more digital dental features.

2. The method of claim 1, further comprising deleting all regions outside of the one or more regions of interest from the digital dental impression.

3. The method of claim 2, wherein determining one or more regions of interest from the joined one or more digital dental features comprises starting at an initial cusp point and growing teeth and gum region from an arch curve.

4. The method of claim 1, wherein the one or more regions of interest comprises a tooth region.

5. The method of claim 1, wherein the one or more regions of interest comprises a gum region.

6. The method of claim 1, wherein the one or more dental features comprises at least one tooth cusp.

7. The method of claim 6, wherein detecting the at least one tooth cusp comprises identifying an occlusion axis, and finding surface points based on curvature.

8. The method of claim 6, wherein detecting the at least one tooth cusp comprises identifying a center of surface regions with several local maxima substantially in a direction of an occlusion direction.

9. The method of claim 6, wherein filtering the at least one tooth cusp comprises filtering by an angle between a cusp-region average normal axis and an occlusion axis.

10. The method of claim 9, wherein a ratio below a user-selectable minimum threshold ratio indicates a non-tooth cusp region.

11. The method of claim 9, wherein a ratio above a maximum threshold ratio indicates a non-tooth cusp region.

12. The method of claim 6, wherein filtering the at least one tooth cusp comprises filtering by ratio of surface area in 3D to a visible 2D surface area from occlusion direction.

13. The computer-implemented method of claim 6, wherein joining tooth cusps comprises constructing a best curve connecting the tooth cusps.

14. The method of claim 13, wherein the best curve comprises a polyline.

15. The method of claim 13, wherein the best curve follows an arch curve.

16. The method of claim 13, wherein the best curve comprises determining a constructive a best curve passing substantially close to a maximal subset of previously found and filtered cusps.

17. The method of claim 16, wherein determining one or more regions of interest from the joined one or more digital dental features comprises starting at an initial cusp point and growing teeth and gum region from filtered tooth cusps.

18. The method of claim 13, wherein the best curve is an analytical smooth curve.

19. The method of claim 18, wherein the analytical smooth curve is one from the group consisting of a parabola, ellipse, or hyperbola.

20. The method of claim 13, wherein the best curve is a polyline joining a maximal subset of found and filtered cusps and a minimized summed angle between successive polyline segments.

21. The method of claim 1, wherein determining one or more regions of interest from the joined one or more digital dental features comprises starting at an initial cusp point and growing teeth and gum region until a cutoff value.

22. The method of claim 21, wherein the cutoff value is a lowest point along one or more paths on a digital surface with respect to an occlusion axis.

23. The computer-implemented method of claim 21, wherein the cutoff value is a distance from a cusp.

24. A non-transitory computer readable medium storing executable computer program instructions for digitally processing a digital dental impression, the computer program instructions comprising instructions for:

detecting one or more anatomical dental features in a digital dental impression;
   filtering the one or more anatomical dental features;
   digitally joining the one or more anatomical dental features; and
   determining one or more regions of interest from the joined one or more anatomical dental features.

25. The method of claim 24, further comprising deleting all regions outside of the one or more regions of interest from the digital dental impression.

26. The method of claim 24, wherein the one or more regions of interest comprises a tooth region.

27. The method of claim 24, wherein the one or more regions of interest comprises a gum region.

28. A digital impression processing system for creating a digital model from a CT scan, comprising:

a processor;
   a computer-readable storage medium comprising instructions executable by the processor to perform steps comprising:
   detecting one or more anatomical dental features in a digital dental impression;
   filtering the one or more anatomical dental features;
   digitally joining the one or more anatomical dental features; and
   determining one or more regions of interest from the joined one or more anatomical dental features.

29. The method of claim 28, further comprising deleting all regions outside of the one or more regions of interest from the digital dental impression.

30. The method of claim 28, wherein the one or more regions of interest comprises a tooth region.

31. The method of claim 28, wherein the one or more regions of interest comprises a gum region.

* * * * *